(12) United States Patent
Burbank et al.

(10) Patent No.: US 12,364,795 B2
(45) Date of Patent: Jul. 22, 2025

(54) FILTRATION SYSTEM FOR PREPARATION OF FLUIDS FOR MEDICAL APPLICATIONS

(71) Applicant: NxStage Medical, Inc., Lawrence, MA (US)

(72) Inventors: Jeffrey H. Burbank, Manchester, MA (US); James M. Brugger, Newburyport, MA (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 18/135,255

(22) Filed: Apr. 17, 2023

(65) Prior Publication Data
US 2023/0302209 A1 Sep. 28, 2023

Related U.S. Application Data

(60) Division of application No. 16/889,930, filed on Jun. 2, 2020, now Pat. No. 11,633,527, which is a division
(Continued)

(51) Int. Cl.
*A61J 1/05* (2006.01)
*A61J 1/14* (2023.01)
(Continued)

(52) U.S. Cl.
CPC ............. *A61M 1/1668* (2014.02); *A61J 1/05* (2013.01); *A61J 1/1468* (2015.05); *A61J 1/1475* (2013.01);
(Continued)

(58) Field of Classification Search
CPC .......... A61J 1/05; A61J 1/1468; A61J 1/1475; A61J 1/2003; A61M 1/14; A61M 1/1656;
(Continued)

(56) References Cited

U.S. PATENT DOCUMENTS 2,936,757 A 5/1960 Trace
2,995,334 A 8/1961 Henderson et al.
(Continued)

FOREIGN PATENT DOCUMENTS

DE 8305713 U1 12/1985
DE 19704564 A1 8/1998
(Continued)

OTHER PUBLICATIONS

"Risk Free Connection of Pre-Sterilized Single Use Fluid Path Assemblies to Stainless Steel SIP Systems with Lynx ST (Steam-to) Connectors." Millipore Corporation Catalogue, May 2003.
(Continued)

*Primary Examiner* — Benjamin L Lebron
(74) *Attorney, Agent, or Firm* — Potomac Law Group, PLLC

(57) ABSTRACT

A system for filling multiple sterile containers includes a filter with an inlet port and multiple outlet ports, the outlet ports being pre-attached to sterile containers by respective filling lines of each container. Each container has an interior and each of the respective filling lines are connected to a respective container interior. The respective filling lines are sealed to the outlet ports and the containers such that the container interiors are isolated from an external environment except the inlet port, via the filter, forming a combined interior volume which is sterile. A container that is connectable to an outlet port the system has a bladder, a first tube and a second tube connected to the bladder, and a sterilizing filter. The container, the first tube and the second tube, and the sterilizing filter are sterile before water is flowed through the sterilizing filter into the bladder.

13 Claims, 28 Drawing Sheets

Related U.S. Application Data of application No. 15/474,849, filed on Mar. 30, 2017, now Pat. No. 10,926,016, which is a division of application No. 13/861,172, filed on Apr. 11, 2013, now Pat. No. 9,636,444, which is a continuation of application No. 12/296,415, filed as application No. PCT/US2007/066251 on Apr. 9, 2007, now Pat. No. 8,469,331.

(60) Provisional application No. 60/744,496, filed on Apr. 7, 2006.

(51) Int. Cl.
| | |
|---|---|
| *A61J 1/20* | (2006.01) |
| *A61M 1/14* | (2006.01) |
| *A61M 1/16* | (2006.01) |
| *A61M 1/28* | (2006.01) |
| *A61M 1/34* | (2006.01) |
| *A61M 39/28* | (2006.01) |
| *B01D 61/14* | (2006.01) |
| *B01D 63/00* | (2006.01) |
| *B01L 3/00* | (2006.01) |
| *B65B 3/28* | (2006.01) |
| *B65B 3/30* | (2006.01) |
| *B65B 55/04* | (2006.01) |
| *C02F 1/44* | (2023.01) |
| *F16K 7/06* | (2006.01) |
| *F16L 55/00* | (2006.01) |
| *F16L 55/07* | (2006.01) |
| *A61M 39/10* | (2006.01) |
| *C02F 103/02* | (2006.01) |

(52) U.S. Cl.
CPC ............. *A61J 1/2003* (2015.05); *A61M 1/14* (2013.01); *A61M 1/1656* (2013.01); *A61M 1/167* (2014.02); *A61M 1/1672* (2014.02); *A61M 1/1674* (2014.02); *A61M 1/28* (2013.01); *A61M 1/3413* (2013.01); *A61M 1/342* (2013.01); *A61M 1/3462* (2013.01); *A61M 39/288* (2013.01); *B01D 61/145* (2013.01); *B01D 61/146* (2022.08); *B01D 63/00* (2013.01); *B01L 3/502* (2013.01); *B65B 3/28* (2013.01); *B65B 3/30* (2013.01); *B65B 55/04* (2013.01); *C02F 1/444* (2013.01); *F16K 7/068* (2013.01); *F16L 55/00* (2013.01); *F16L 55/07* (2013.01); *A61M 39/1011* (2013.01); *A61M 2205/273* (2013.01); *B01D 61/14* (2013.01); *B01L 2200/026* (2013.01); *B01L 2200/0605* (2013.01); *B01L 2200/0689* (2013.01); *B01L 2300/0681* (2013.01); *B01L 2300/0864* (2013.01); *C02F 2103/026* (2013.01); *Y10T 137/8593* (2015.04)

(58) Field of Classification Search
CPC .. A61M 1/1668; A61M 1/167; A61M 1/1672; A61M 1/1674; A61M 1/28; A61M 1/3413; A61M 1/342; A61M 1/3462; A61M 39/1011; A61M 39/288; A61M 2205/273; B01D 61/14; B01D 61/145; B01D 61/146; B01D 63/00; B01L 3/502; B01L 2200/026; B01L 2200/0605; B01L 2200/0689; B01L 2300/0681; B01L 2300/0864; B65B 3/28; B65B 3/30; B65B 55/04; C02F 1/444; C02F 2103/026; F16K 7/068; F16L 55/00; F16L 55/07
See application file for complete search history.

(56) References Cited

U.S. PATENT DOCUMENTS

| | | |
|---|---|---|
| 3,100,486 A | 8/1963 | Nehring |
| 3,103,335 A | 9/1963 | Martinez |
| 3,165,114 A | 1/1965 | Garrett |
| 3,467,095 A | 9/1969 | Ross |
| 3,646,935 A | 3/1972 | Holbrook |
| 3,647,397 A | 3/1972 | Coleman |
| 4,059,512 A | 11/1977 | Harris |
| 4,144,884 A | 3/1979 | Tersteegen et al. |
| 4,202,332 A | 5/1980 | Tersteegen et al. |
| 4,246,101 A | 1/1981 | Selby |
| 4,370,983 A | 2/1983 | Lichtenstein |
| 4,495,067 A | 1/1985 | Klein et al. |
| 4,560,382 A | 12/1985 | Isono |
| 4,596,550 A | 6/1986 | Troutner |
| 4,610,790 A | 9/1986 | Reti et al. |
| 4,623,450 A | 11/1986 | Vantard et al. |
| 4,626,240 A | 12/1986 | Edelman et al. |
| 4,661,246 A | 4/1987 | Ash |
| 4,711,715 A | 12/1987 | Polaschegg |
| 4,753,371 A | 6/1988 | Michielin et al. |
| 4,754,786 A | 7/1988 | Roberts |
| 4,784,495 A | 11/1988 | Jonsson et al. |
| 4,902,282 A | 2/1990 | Bellotti et al. |
| 5,102,399 A | 4/1992 | Chu |
| 5,259,954 A | 11/1993 | Taylor |
| 5,308,333 A | 5/1994 | Skakoon |
| 5,362,642 A | 11/1994 | Kern |
| 5,368,555 A | 11/1994 | Sussman et al. |
| 5,536,412 A | 7/1996 | Ash |
| 5,536,413 A | 7/1996 | Bormann et al. |
| 5,591,344 A | 1/1997 | Kenley et al. |
| 5,614,412 A * | 3/1997 | Smith ............... A61J 3/002 435/809 |
| 5,622,626 A | 4/1997 | Matkovich et al. |
| 5,645,734 A | 7/1997 | Kenley et al. |
| 5,690,831 A | 11/1997 | Kenley et al. |
| 5,702,597 A | 12/1997 | Chevallet et al. |
| 5,707,038 A | 1/1998 | Cocatre-Zilgien |
| 5,779,905 A | 7/1998 | Morandi et al. |
| 5,782,762 A | 7/1998 | Vining |
| 5,919,357 A | 7/1999 | Wilkins et al. |
| 5,972,225 A | 10/1999 | Karras et al. |
| 6,039,877 A | 3/2000 | Chevallet et al. |
| 6,044,691 A | 4/2000 | Kenley et al. |
| 6,132,616 A | 10/2000 | Twardowski et al. |
| 6,136,201 A | 10/2000 | Shah et al. |
| 6,146,536 A | 11/2000 | Twardowski |
| 6,187,207 B1 | 2/2001 | Brauer |
| 6,253,567 B1 | 7/2001 | Imanari et al. |
| 6,254,567 B1 | 7/2001 | Treu et al. |
| 6,280,634 B1 | 8/2001 | Shah et al. |
| 6,284,142 B1 | 9/2001 | Muller |
| 6,287,516 B1 | 9/2001 | Matson et al. |
| 6,331,252 B1 | 12/2001 | Sayyid et al. |
| 6,428,518 B1 | 8/2002 | Brengle et al. |
| 6,475,385 B1 | 11/2002 | Boyce et al. |
| 6,561,997 B1 | 5/2003 | Weitzel et al. |
| 6,572,576 B2 | 6/2003 | Brugger et al. |
| 6,579,253 B1 | 6/2003 | Burbank et al. |
| 6,582,385 B2 | 6/2003 | Burbank et al. |
| 6,589,482 B1 | 7/2003 | Burbank et al. |
| 6,595,943 B1 | 7/2003 | Burbank |
| 6,626,857 B1 | 9/2003 | Ohta et al. |
| 6,638,477 B1 | 10/2003 | Treu et al. |
| 6,638,478 B1 | 10/2003 | Treu et al. |
| 6,649,063 B2 | 11/2003 | Brugger et al. |
| 6,691,058 B2 | 2/2004 | Blakley |
| 6,743,193 B2 | 6/2004 | Brugger et al. |
| 6,830,553 B1 | 12/2004 | Burbank et al. |
| 6,852,090 B2 | 2/2005 | Burbank et al. |
| 6,855,122 B1 | 2/2005 | Ohta et al. |
| 6,955,655 B2 | 10/2005 | Burbank et al. |
| 6,962,575 B2 | 11/2005 | Tal |
| 7,214,312 B2 | 5/2007 | Brugger et al. |
| 7,226,538 B2 | 6/2007 | Brugger et al. |

(56) References Cited

U.S. PATENT DOCUMENTS

| | | |
|---|---|---|
| 7,473,238 B2 | 1/2009 | Brugger et al. |
| 7,544,300 B2 | 6/2009 | Brugger et al. |
| 2001/0016699 A1 | 8/2001 | Burbank et al. |
| 2001/0021817 A1 | 9/2001 | Brugger et al. |
| 2001/0039441 A1 | 11/2001 | Ash |
| 2001/0048909 A1 | 12/2001 | Taylor |
| 2002/0077580 A1 | 6/2002 | Tobe |
| 2002/0085952 A1 | 7/2002 | Ellingboe et al. |
| 2002/0104800 A1 | 8/2002 | Collins et al. |
| 2002/0167322 A1 | 11/2002 | He et al. |
| 2003/0010703 A1 | 1/2003 | Pippert et al. |
| 2003/0042201 A1 | 3/2003 | Sizelove et al. |
| 2003/0051767 A1 | 3/2003 | Coccaro et al. |
| 2003/0080140 A1 | 5/2003 | Neas et al. |
| 2003/0105435 A1 | 6/2003 | Taylor |
| 2003/0130606 A1 | 7/2003 | Tuck |
| 2003/0168389 A1 | 9/2003 | Astle et al. |
| 2003/0236481 A1 | 12/2003 | Burbank |
| 2004/0045881 A1 | 3/2004 | Collins et al. |
| 2004/0069709 A1 | 4/2004 | Brugger et al. |
| 2004/0082903 A1 | 4/2004 | Micheli |
| 2004/0089594 A1 | 5/2004 | Collins et al. |
| 2004/0186415 A1 | 9/2004 | Burbank et al. |
| 2004/0222139 A1 | 11/2004 | Brugger et al. |
| 2004/0232079 A1 | 11/2004 | Taylor et al. |
| 2005/0045548 A1 | 3/2005 | Brugger et al. |
| 2005/0103717 A1 | 5/2005 | Jha et al. |
| 2005/0171501 A1 | 8/2005 | Kelly |
| 2005/0209547 A1 | 9/2005 | Burbank et al. |
| 2007/0007208 A1 | 1/2007 | Brugger et al. |
| 2007/0038191 A1 | 2/2007 | Burbank et al. |
| 2007/0260168 A1 | 11/2007 | Brugger et al. |
| 2008/0053905 A9 | 3/2008 | Brugger et al. |
| 2008/0203023 A1 | 8/2008 | Burbank et al. |
| 2008/0210606 A1 | 9/2008 | Burbank |
| 2008/0230450 A1 | 9/2008 | Burbank et al. |

FOREIGN PATENT DOCUMENTS

| | | |
|---|---|---|
| GB | 2135598 A | 9/1984 |
| JP | 4941276 U | 11/1974 |
| JP | S57211362 A | 12/1982 |
| JP | 2003175101 A | 6/2003 |
| JP | 2004000583 A | 1/2004 |
| WO | 1996036370 A1 | 11/1996 |
| WO | 1999056696 A1 | 11/1999 |
| WO | 2002032476 A2 | 4/2002 |
| WO | 2002095675 A1 | 11/2002 |
| WO | 2003006100 A1 | 1/2003 |
| WO | 2003006139 A1 | 1/2003 |
| WO | 2003103533 A2 | 12/2003 |
| WO | 2004062710 A2 | 7/2004 |
| WO | 2004066121 A2 | 8/2004 |
| WO | 2004080282 A2 | 9/2004 |
| WO | 2004084972 A2 | 10/2004 |
| WO | 2005068043 A1 | 7/2005 |
| WO | 2006074429 A1 | 7/2006 |
| WO | 2007118235 A2 | 10/2007 |

OTHER PUBLICATIONS

International Preliminary Examination Report dated Oct. 8, 2008 for International Application No. PCT/US07/66251.
International Search Report dated Aug. 27, 2008 for International Application No. PCT/US07/66251.
Office Action issued May 24, 2012, in Japanese Patent Application No. 2009-504504.
Pall Corporation, "Selection Guide: Separation Products for Centrifugal and Tangential Flow Filtration", Retrieved from http://www.pall.com/main/laboratory/literature-library-details.page?id=70-46 on Jul. 7, 2015.
Shipe, B. "The Case for UV in Dechlorination Applications." Water Conditioning and Purification Magazine, Jan. 2003, 45(1): pp. 34-36.

* cited by examiner

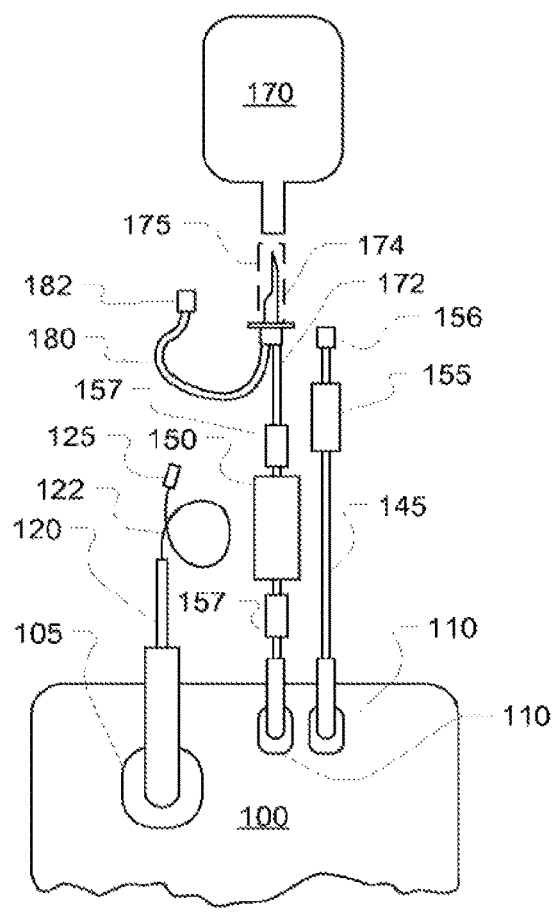
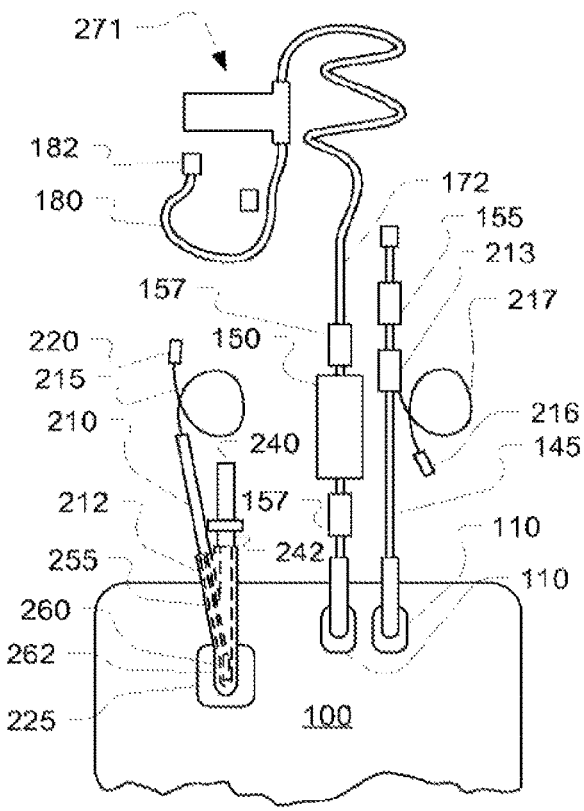
Fig. 9A
Fig. 9B
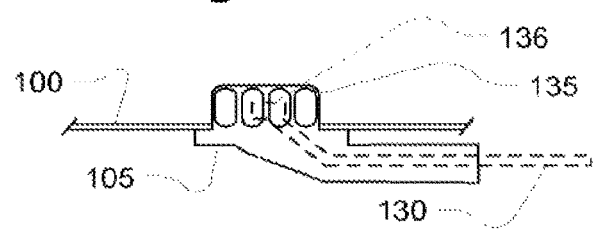
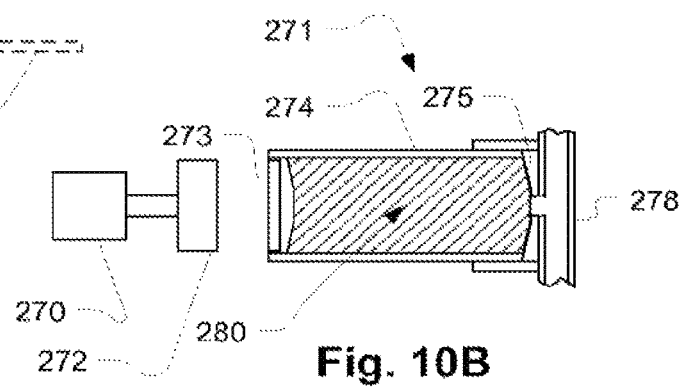
Fig. 10A
Fig. 10B

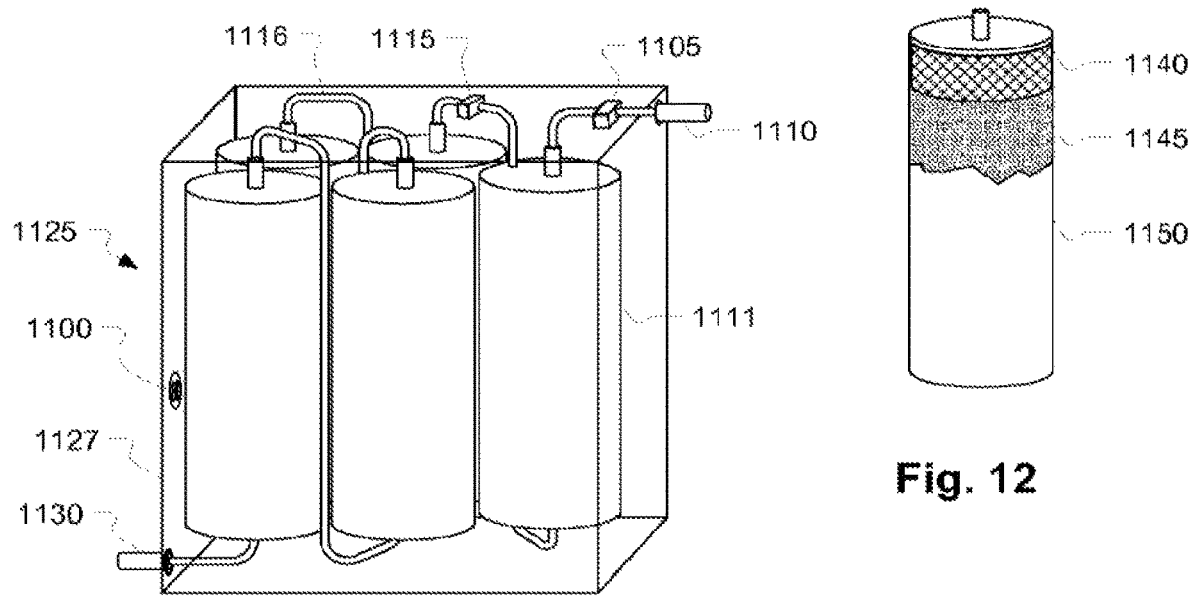
Fig. 11
Fig. 12
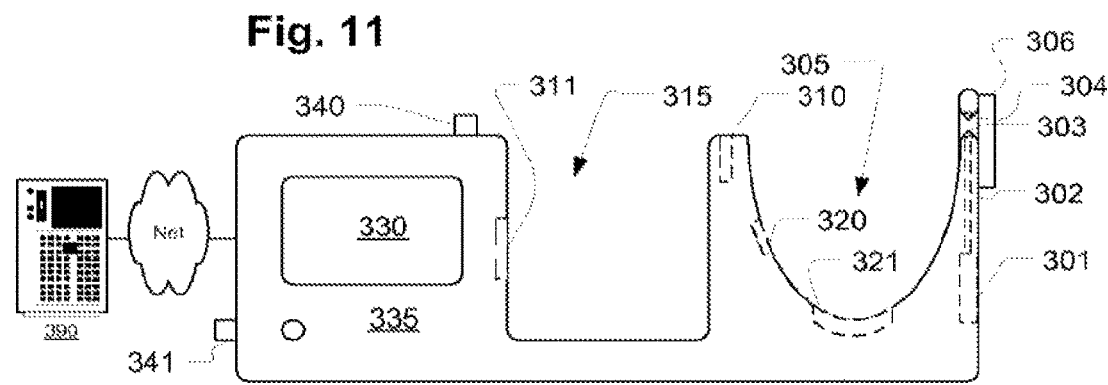
Fig. 13A
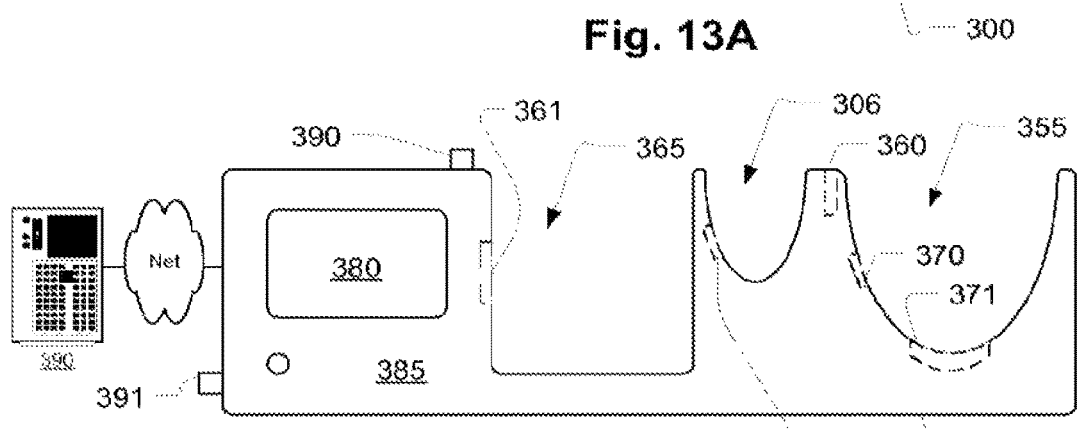
Fig. 13B

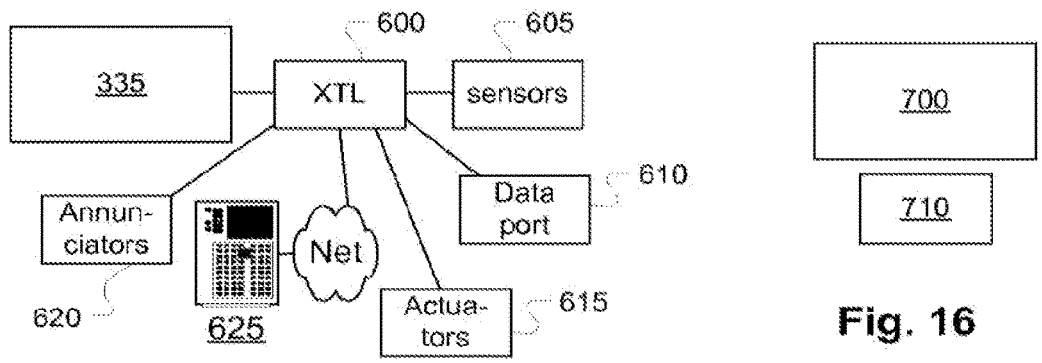
Fig. 14
Fig. 16
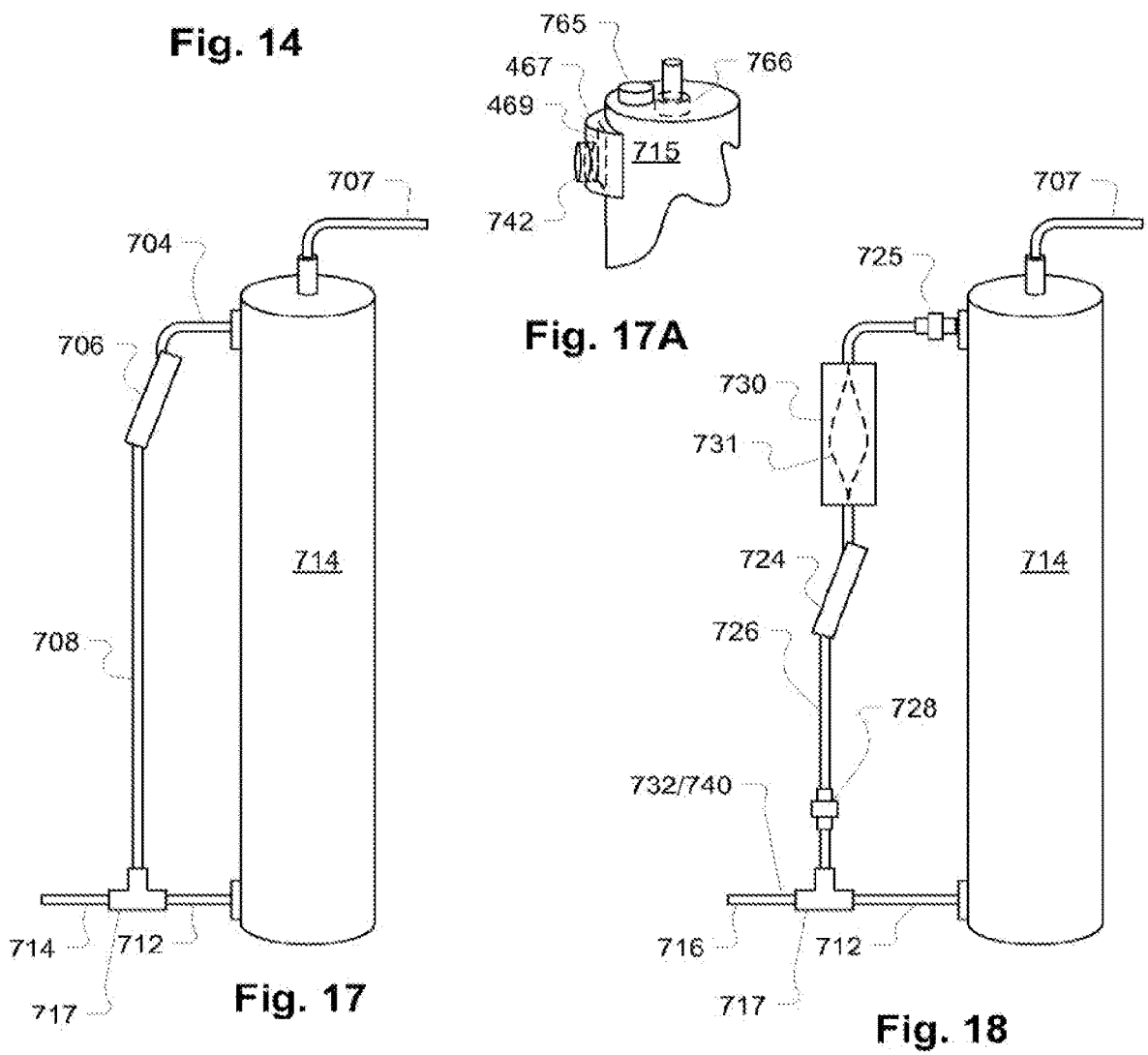
Fig. 17A
Fig. 17
Fig. 18

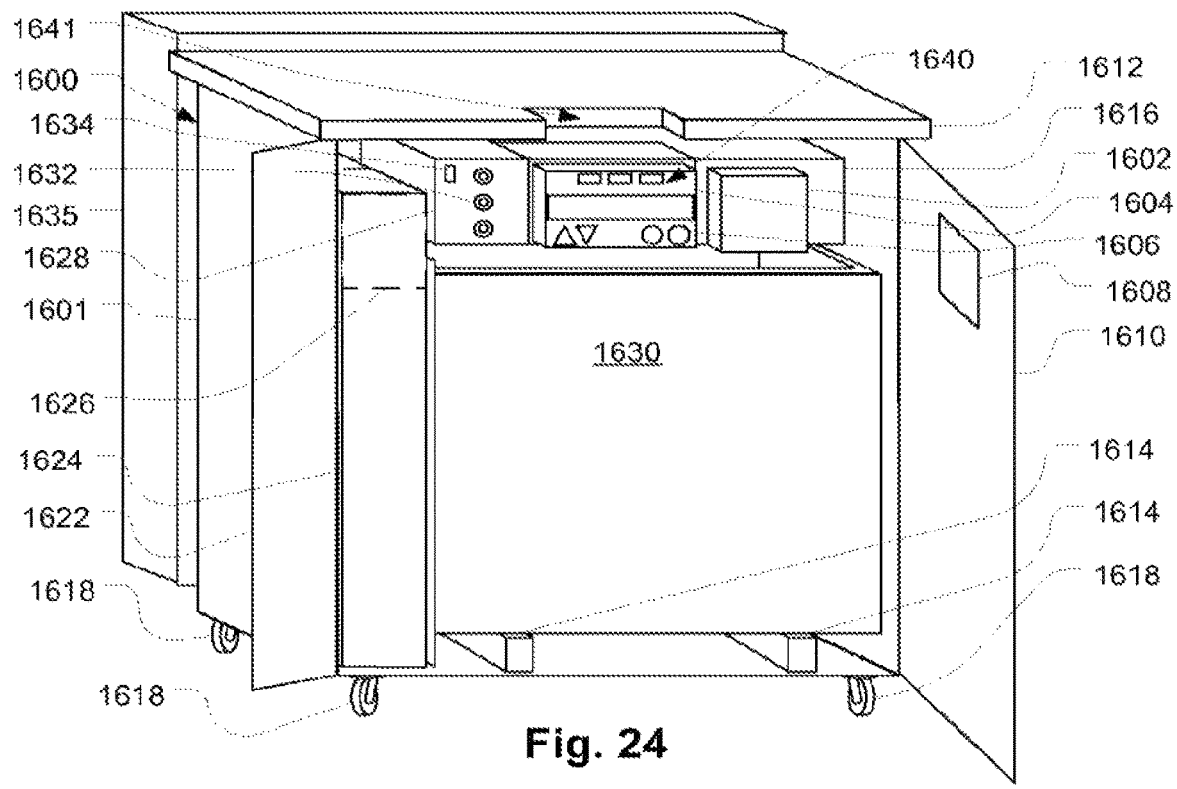
Fig. 24
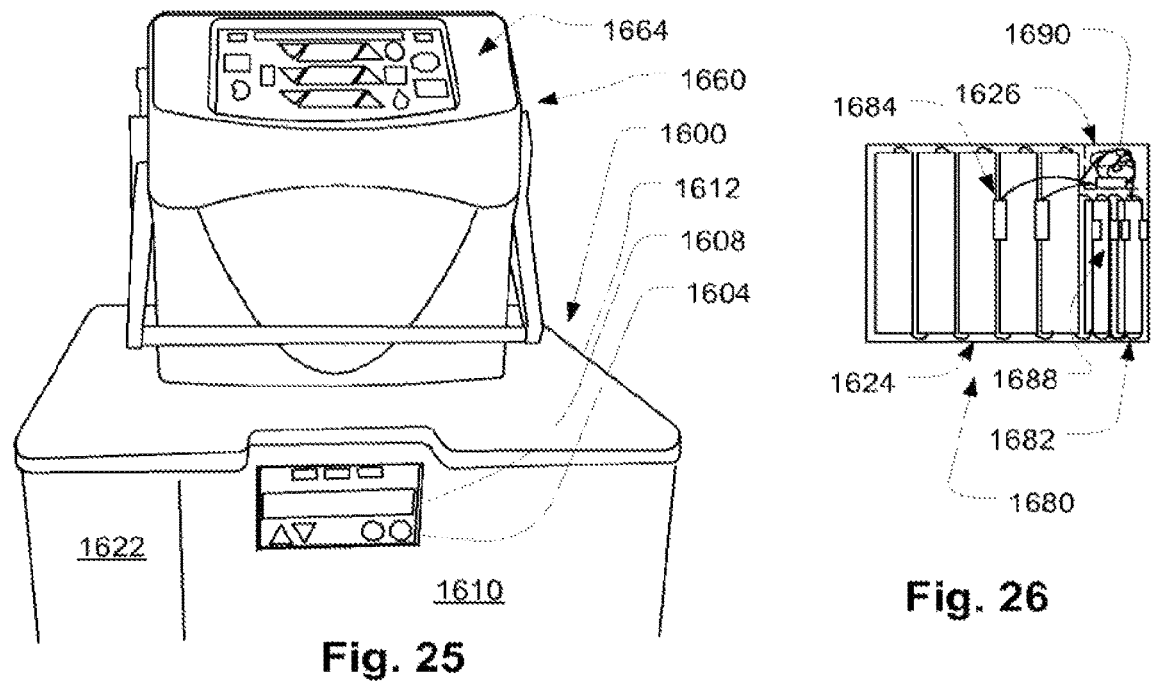
Fig. 25
Fig. 26

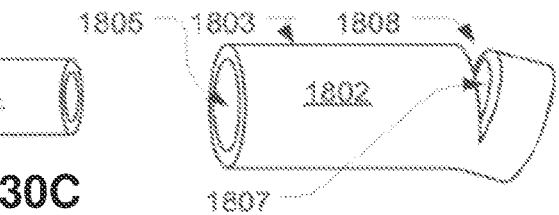
Fig. 30C
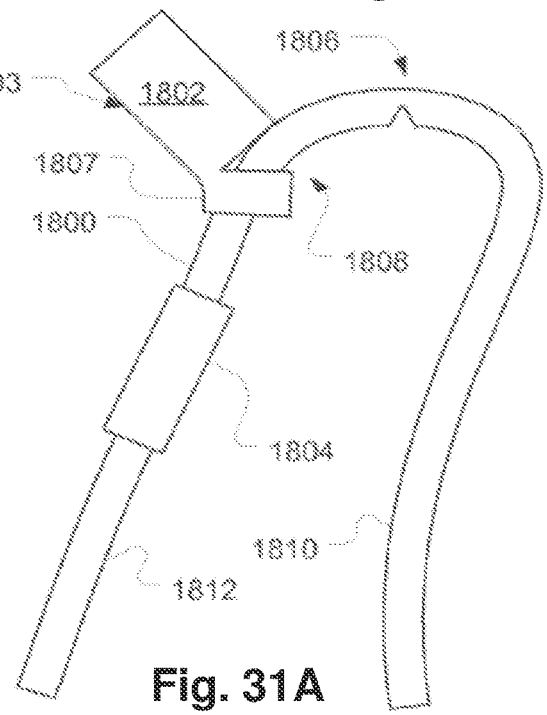
Fig. 30B
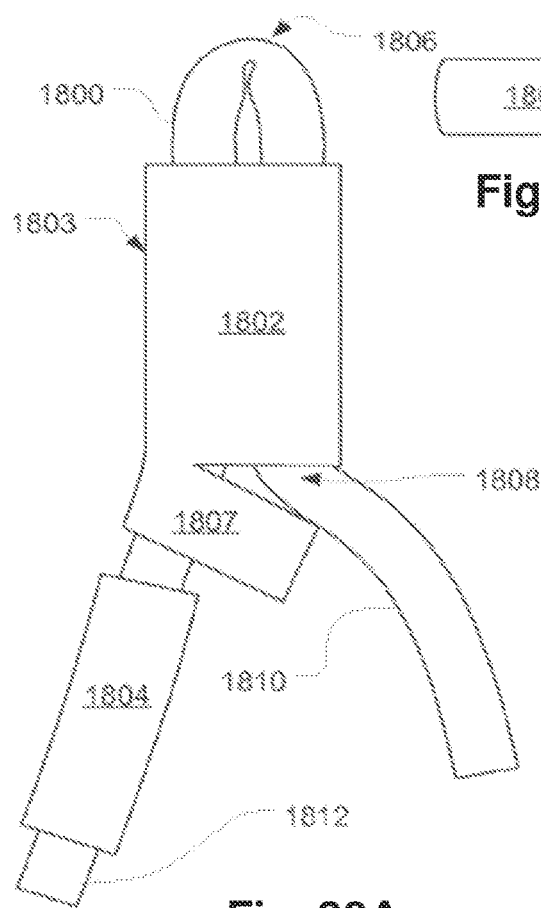
Fig. 30A
Fig. 31A
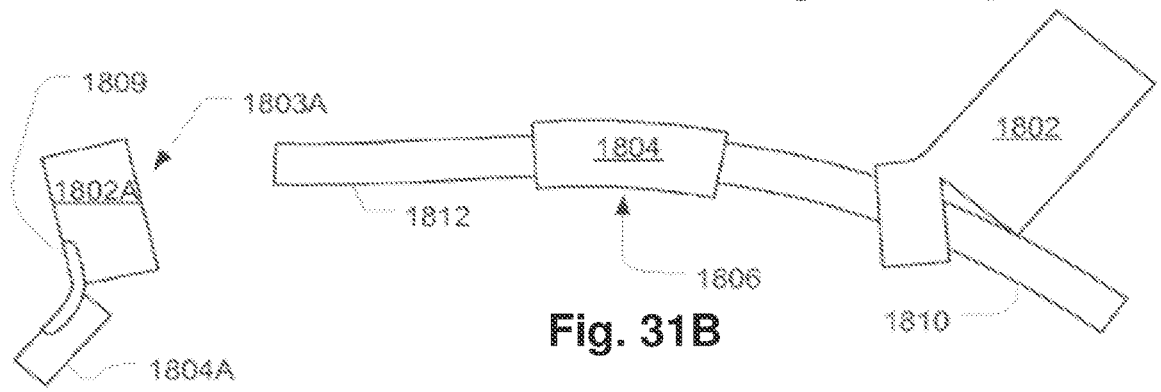
Fig. 31B
Fig. 32

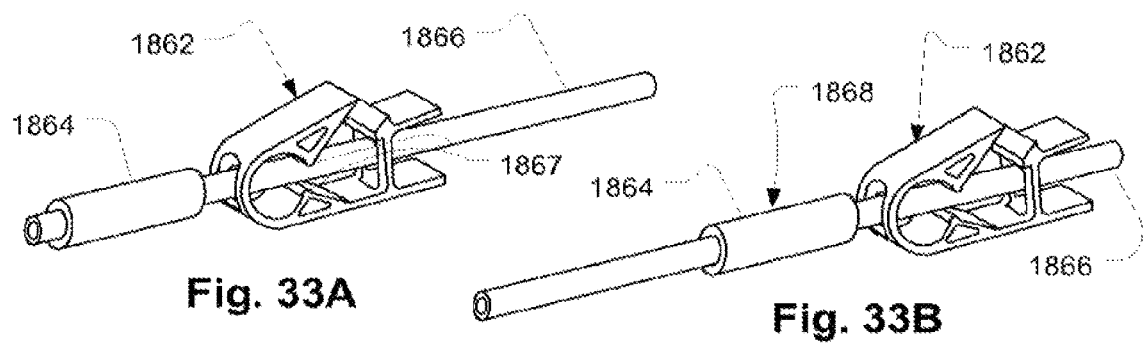
Fig. 33A  Fig. 33B
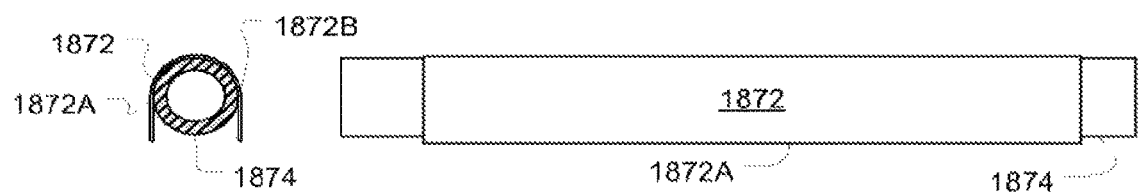
Fig. 34A  Fig. 34B
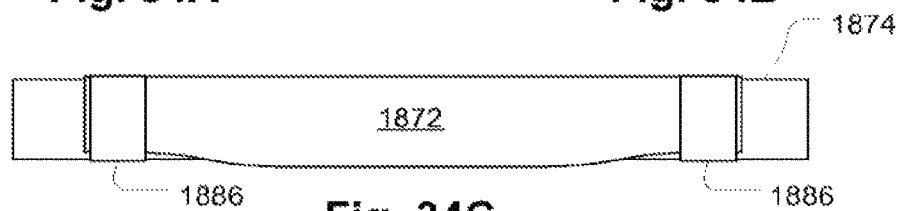
Fig. 34C
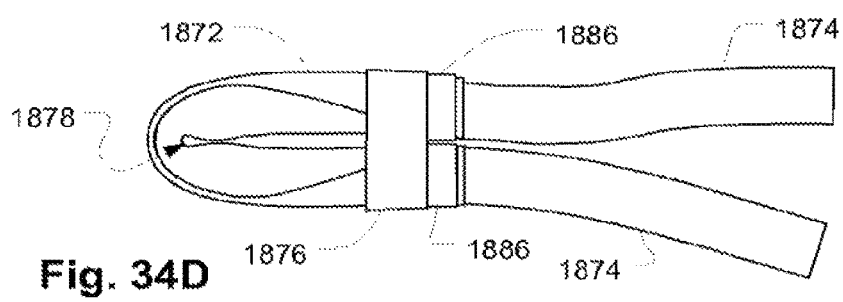 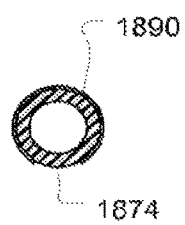
Fig. 34D  Fig. 34F
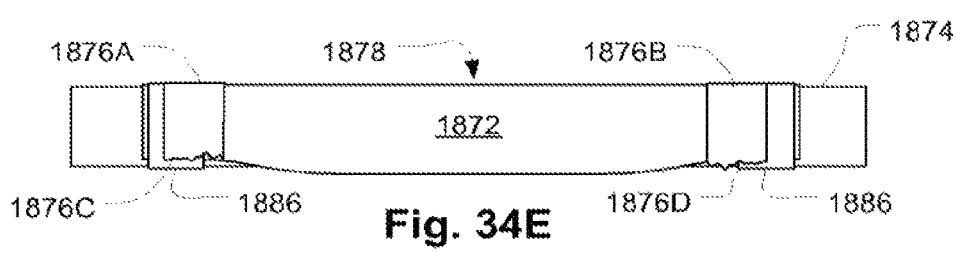
Fig. 34E

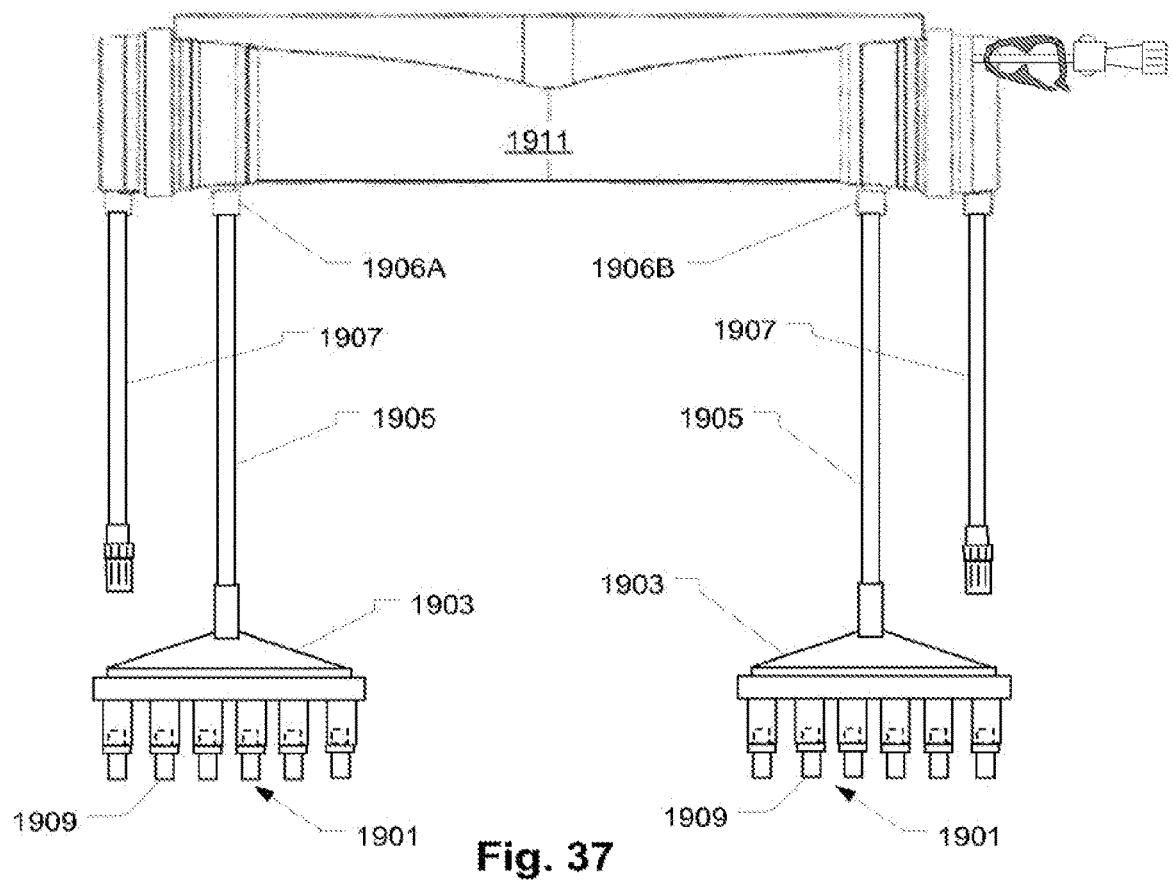
Fig. 37
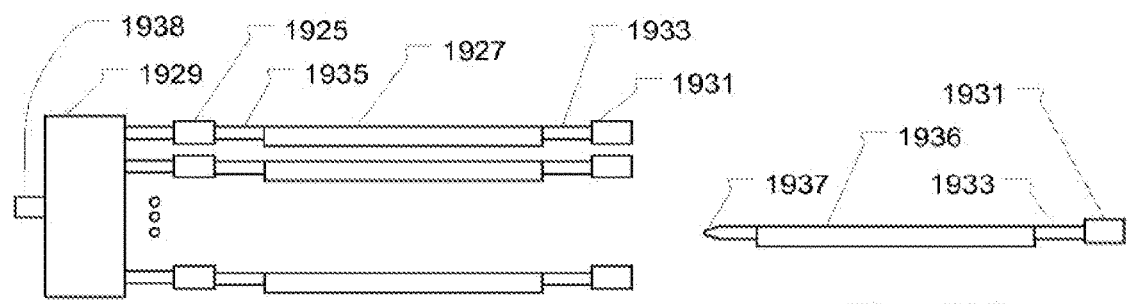
Fig. 38A
Fig. 38B

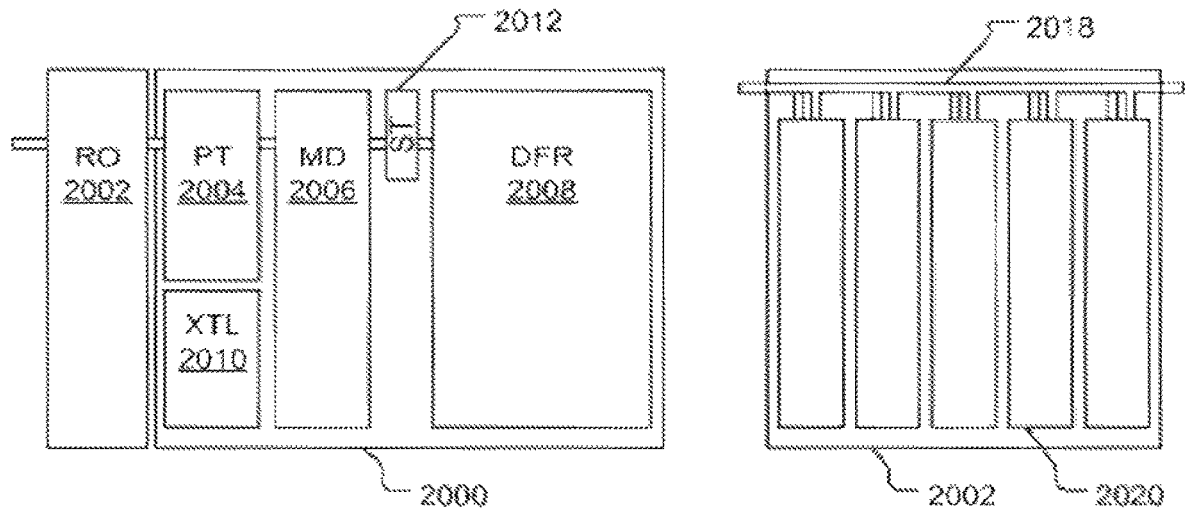
Fig. 43  Fig. 44
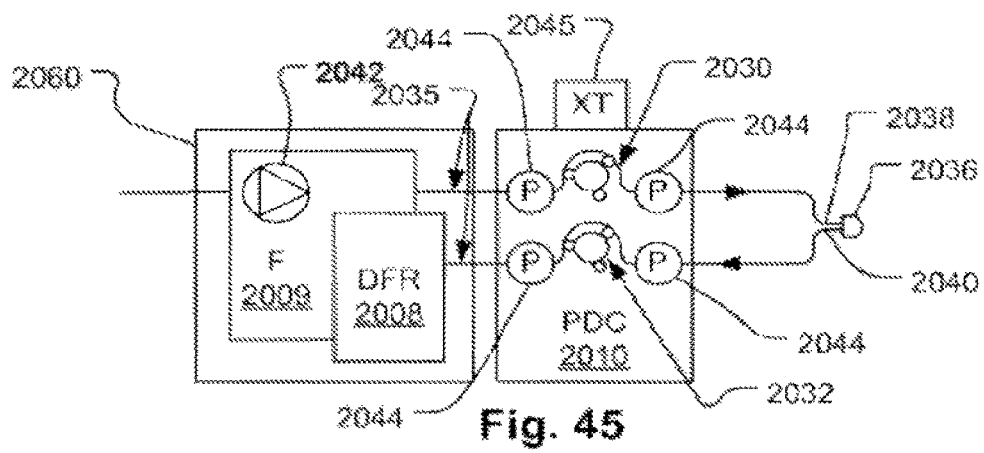
Fig. 45
Fig. 46

FILTRATION SYSTEM FOR PREPARATION OF FLUIDS FOR MEDICAL APPLICATIONS

CROSS REFERENCE TO RELATED APPLICATIONS

The present application is a is a divisional of U.S. application Ser. No. 16/889,930, filed Jun. 2, 2020, which is a divisional of U.S. application Ser. No. 15/474,849, filed Mar. 30, 2017, now issued as U.S. Pat. No. 10,926,016 on Feb. 23, 2021, which is a divisional of U.S. application Ser. No. 13/861,172, filed Apr. 11, 2013, now issued as U.S. Pat. No. 9,636,444 on May 2, 2017, which is a continuation of U.S. application Ser. No. 12/296,415, filed Oct. 7, 2008 (371(c) date of 28 Oct. 2008), now issued as U.S. Pat. No. 8,469,331 on Jun. 25, 2013, which is a U.S. national stage entry of International Application No. PCT/US2007/066251, filed Apr. 9, 2007, which the benefit of U.S. Provisional Application No. 60/744,496, titled "FILTRATION SYSTEM FOR PREPARATION OF FLUIDS FOR MEDICAL APPLICATIONS," filed 7 Apr. 2006, all of which are incorporated by reference herein in their entireties.

BACKGROUND OF THE INVENTION

Many medical applications require purified water and other fluids. for example, hemofiltration, tissue irrigation, and hemodiafiltration. Some prior art systems have focused on continuous purification processes that require a separate diafiltration/purification apparatus that must be periodically purged and verified to provide sufficient constant flow of sterile replacement fluid. (See Chavallet U.S. Pat. Nos. 6,039,877 and 5,702,597.) Such devices are necessarily complicated and require separate pumping systems for the purification process. In addition, the rate of supply of fluid for such systems is very high, requiring expensive filters to be used. The same high-rate problem exists for the generation of replacement fluid for hemofiltration, and therefore also requires expensive filtering apparatus.

Large and small scale inline systems are known for preparation of infusible fluids and for preparation of dialysate. The following prior art references discuss examples of such systems.
US Patent Publication No. 2004/0232079
US Patent Publication No. 2003/0105435
U.S. Pat. No. 5,645,734
U.S. Pat. No. 5,782,762
U.S. Pat. No. 6,136,201
PURELAB Maxima, Ultra-Pure Water Purification Systems (http://www.elgalabwater.com)
Shipe, Brad; "The Case for UV in Dechlorination Applications," Water Conditioning & Purification Magazine, January 2003, Vol. 45 No. 1.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIGS. 9A and 9B illustrate embodiments of a batch container.

FIG. 10A illustrates a fluid quality sensor such as a conductivity or resistivity sensor configuration for sensing fluid quality in a container.

FIG. 10B illustrates a medicament concentrate cartridge.

FIG. 11 illustrates a filter module in partial ghost perspective view.

FIG. 12 illustrates a filter cartridge with an expansion device.

FIGS. 13A and 13B illustrate fluid preparation devices for use with a replaceable filter module such as the one illustrated in FIG. 11.

FIG. 14 illustrates a control system to support features of various embodiments.

FIG. 16 illustrates a treatment environment for use of a control embodiment.

FIGS. 17, 17A, and 18 illustrate ultrafilter configurations that are tolerant of the evolution of air from within the ultrafilter.

FIGS. 24 and 25 illustrate various mechanical features including a housing for a treatment fluid preparation and storage device according to an embodiment of the invention.

FIG. 26 illustrates a long term disposable filter module for a treatment fluid preparation and storage device according to an embodiment of the invention.

FIG. 30A-30C show an embodiment of a tubing clamp device that may be used with a batch container.

FIGS. 31A and 31B show stages in the use of the embodiment of FIGS. 31A-30C.

FIG. 32 shows another a tubing clamp device that may be used with a batch container.

FIGS. 33A and 33B show another a tubing clamp device that may be used with a batch container.

FIG. 34A-34E show another a tubing clamp device that may be used with a batch container.

FIG. 34F shows a variation on the embodiment of FIGS. 34A-34E.

FIG. 37 shows an apparatus to allow multiple batch containers to be pre-filled with medicament concentrate.

FIGS. 38A and 38B illustrate the use of the embodiment of FIG. 37 and components of a substructure used for pre-filing multiple batch containers.

FIG. 43 shows a water purification device with a line pressure RO stage.

FIG. 44 shows an embodiment of a flat RO filter module.

FIG. 45 shows a water purification module/peritoneal dialysis treatment device configured for purification of water.

FIG. 46 shows the water purification module/peritoneal dialysis treatment device configured for treatment.

SUMMARY OF EMBODIMENTS

Figure 1A:
FIG. 1A illustrates a fluid preparation apparatus embodiments in a figurative way for discussing various features and arrangements of a medical fluid purification system.

According to an embodiment, a fluid line sealing device has a tube with a first member movable attached thereto. The first member holds the tube in a folded condition such that the tube is sealed. The first member is movable relative to the tube to permit the fold to be released, thereby unsealing the tube. A second member has an internal size and shape close to that of the tube and can slide over the tube. The second member is preferably slidably attached to the tube and adjacent the first member. In a particular embodiment, the tube has a folded portion, with sides on either side of the folded portion, and the first member has a portion shaped with a cylindrical interior. In this embodiment, at least the tube sides fit into the cylindrical interior. Preferably, the first member has a retaining portion that remains attached to the tube when the first member is moved relative to the tube to permit the fold to be released.

The second member reshapes the tube by forcing any distortions caused by the folding to be undone by the urging of the second member. For example, the tube may be cylindrical and the second member may have a cylindrical interior that is about the same size as the outside of the tube. In that case, the close fit of the second member undoes any creases caused by the folding. This increases the patency of the tube relative to what it would be if the crease remained.

According to another embodiment, a method of unsealing a fluid line includes straightening a folded tube to unseal it; and placing a member over a folded portion of the tube to increase the patency of a lumen of the tube.

Preferably, the method further includes holding a tube in a bent configuration so as to form a fold that seals the tube. After the bend is released, the member is placed over the tube to increase the patency of the tube. The holding preferably includes providing a removable holding member that maintains the tube in a folded state. The straightening preferably includes moving a retaining member that holds a tube in a folded state.

The retaining member preferably defines an annular portion that surrounds portions of the tube on either side of the folded portion. The retaining member preferably remains movably attached to the tube after the straightening.

In another embodiment, a method for unsealing a fluid line includes disengaging a sealing member that holds a tube in a sealed state and resiliently reshaping a portion of the tube deformed by the sealing member to increase the patency of a lumen of the tube. The method preferably further includes holding a tube in a bent configuration so as to form a fold that seals the tube. The resilient reshaping may be done by a closely conforming element which is shaped as the tube is ideally shaped and which has some flexibility so it can be moved over any creases in the tube caused by folding. The resiliency of the conforming element continuously urges the tube into the shape that has approximately the patency of an undistorted tube. For example, the conforming element can be a resilient plastic tube whose inner diameter is the same as the outer diameter of the tube. Preferably, the element is stiffer than the tube so that it can reshape the tube.

The straightening preferably includes moving the retaining member that holds a tube in a folded state. The retaining member may define an annular portion that surrounds portions of the tube on either side of the folded portion. The retaining member preferably remains movably attached to the tube after the straightening.

According to another embodiment, a tube-sealing device has at least one member and a tube in engagement therewith. The at least one member has one or more first surface and one or more second surface. The at least one member, in a first configuration, holds the at least one first surface against the tube to hold it in a folded state, thereby sealing the tube and creating a deformation of the tube that seals it. The tube is such that a partial deformation is retained by the tube due to stress relaxation over time. The at least one member, in a second configuration, urges the at least one second surface against the tube such that the partial deformation retained by the tube is at least partially removed.

According to another embodiment, a medicament fluid circuit has a container with an interior chamber. The container has a fluid filling port and a fluid extraction port, both connected to the interior chamber. The filling port has two sterilizing filters, each with a membrane. The sterilizing filters are connected in series such that their membranes are separated by a distance of at least 0.5 cm. A first of the sterilizing filters has a sealed inlet and the fluid extraction port is sealed. The fluid extraction port includes a line and the fluid extraction port line has a pyrogen filter connected thereto to filter contents passing through the fluid extraction port line. Preferably, the filling port has a filling line with a clamp pre-attached to it.

According to another embodiment, a medicament fluid circuit has a container with an interior chamber. The container has a fluid filling port, a fluid extraction port, and a pre-fill port all connected to the interior chamber. The pre-fill port has an inline ultrafilter. The fluid extraction port and the fluid filling ports are sealed by removable seals, which may include connectors. The container is preferably a flexible bag capable of holding at least 20 liters of fluid. The fluid filling port, fluid extraction port, and pre-fill port are preferably all pre-sealed. The ultrafilter pore size is preferably smaller than 0.1 micron.

According to another embodiment, a container has an interior chamber and inlet and outlet fluid lines connected to the interior chamber. At least one of the inlet and outlet fluid lines is connected to a flexible tube with a length of at least 10 cm. lying within the interior chamber. Preferably, the container has a volume of at least 10 liters. In a particular embodiment, only one of the inlet and outlet lines has the flexible tube attached thereto and the other does not. A pre-filling port is preferably connected to the container interior chamber. In another variation of the embodiment, a purified water inlet port is connected to the container interior chamber.

In a particular embodiment, a header is provided, the inlet and outlet lines being connected to the header. The header is preferably connected to at least two additional ports which permit the passage of fluid into and/or out of the container interior chamber. More preferably, the header is connected to at least three additional ports which permit the passage of fluid into and/or out of the container interior chamber.

According to another embodiment, an apparatus for filling multiple containers has a filter with an inlet port and multiple outlet ports. The outlet ports are pre-attached, by filling connections, to containers, each of which an interior and respective ports connected to the interior. All of the respective ports are sealed such that the container interiors are each isolated, except the filling connection, to the respective outlet port.

According to another embodiment, a method of filling multiple containers with concentrated medicament includes providing a filter with an inlet port and multiple outlet ports and attaching each of the outlet ports to a container which is otherwise sealed from the environment. After the attaching, the method further includes sterilizing the filter and the multiple containers. Preferably, the method further includes filling each of the containers by passing a medicament concentrate through the filter into the containers. Also, preferably, the method further includes breaking a connection between the filter and each of the containers while simultaneously sealing the connection to seal the container.

According to another embodiment, a medical fluid treatment device has a replaceable deionization filter. A reverse osmosis filter is connected between a raw water inlet and the replaceable deionization filter. The reverse osmosis filter is characterized by a rejection fraction of less than 95% operating at a pressure of less than 100 psi. Preferably, the replaceable deionization filter has a capacity of at least 400 liters. Preferably, the device further includes a support for a fluid container connected to receive fluid filtered by the replaceable deionization filter. Preferably, a metering pump is connected between the reverse osmosis filter and the deionization filter. In another embodiment, the reverse osmosis filter is characterized by a rejection fraction of less than 90% with a recovery rate of at least 30%. Preferably, the reverse osmosis filter has a capacity of 10,000 liters.

According to another embodiment, a water purification device has a pre-filter includes a sediment filter and an activated carbon filter. A reverse osmosis filter is connected to receive water filtered by the pre-filter. The reverse osmosis filter is characterized by a rejection fraction of less than 95% operating at a pressure of less than 100 psi. A deionization filter is connected to receive water filtered by the reverse osmosis filter.

In a variation of the above embodiment, two inline ultrafilters are connected to receive water filtered by the deionization filter. Preferably, the two are connected in series to help prevent grow-through contamination and provide redundancy protecting against failure of one of the membranes. The reverse osmosis filter is preferably characterized by a rejection fraction of less than 90% with a recovery rate of at least 30%.

According to another embodiment, a method of operating a peritoneal dialysis pump beings by providing a water purification device includes at least one component configured to indicate a quantity of water pumped into a container storing a quantity of fluid required for at least one peritoneal dialysis treatment. The method includes providing a pumping mechanism capable of pumping fluid to a patient and of pumping fluid from the patient, the pumping mechanism having a measurable or controllable pump flow rate. The method further includes connecting the water purification device to the pumping mechanism to convey water through the water purification device and the pumping mechanism into the container while measuring while storing data correlating information responsive to either a commanded flow rate or an indicated flow rate of the pumping mechanism with information responsive to indications of the quantity of water pumped provided by the water purification device.

In a variation of the foregoing method, the method further includes performing a peritoneal dialysis treatment using the data stored data correlating information responsive to either a commanded flow rate or an indicated flow rate of the pumping mechanism with information responsive to indications of the quantity of water pumped provided by the water purification device.

DETAILED DESCRIPTION

The present disclosure relates to apparatus, methods, devices, articles of manufacture, etc. for producing pure water and, in some embodiments, pure solutions. These may be used for the preparation of solutions for medical applications such as tissue irrigation, preparation of pharmaceutical, blood treatments such as hemofiltration, hemodialysis, hemodiafiltration and ultrafiltration, and other treatments.

As described in FIG. 1A, to supply suitable water that is substantially free of unwanted dissolved and undissolved materials, a combination of permanent and replaceable components may be provided at the treatment site. FIG. 1A is an overview of a framework that provides benefits, particularly in certain environments. One such environment is renal replacement therapy. Patients must be treated at least twice a week and often daily. On the other hand, excellent sterility design urges the use of pre-sterilized throw-away components to ensure against various modes of contamination which need not be enumerated. But replacing every component that must be contamination-free upon every use is profoundly expensive, particularly where treatments are done every day. Prior art approaches have addressed this problem by combining permanent components whose sterility is guaranteed by intensive sterilization procedures, some of which are backed up (made failsafe) by using additional disposable components that are used once and discarded. Alternatively, the disposable can be made more robust to avoid the on-site sterilization procedures. But this presents the problem of forcing the designer to use inexpensive, and therefore less desirable components in the disposable portions, or of simply imposing the burden of high cost on the medical treatment system.

Figure 1B:
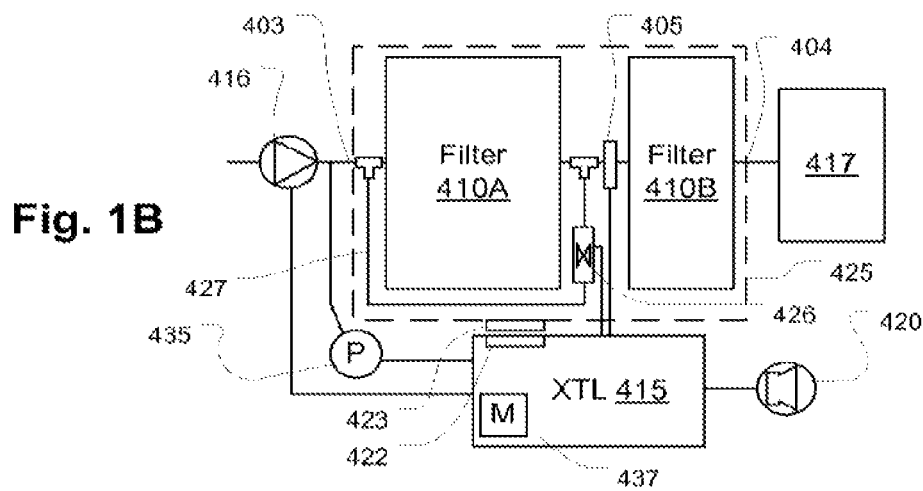
FIG. 1B illustrates a filter device with control elements that provide assurance of fluid quality and prevent breakthrough of contamination upon filter expiration.

FIG. 1A shows a new model that compromises on this point and is considered particularly applicable in the renal replacement therapy environment. A permanent module 920 has certain pretreatment components that may be used repeatedly without replacement and without sterilization and includes filtration and treatment steps that are not unduly inclined to aggravate, or susceptible to, contamination. Examples are illustrated in the further embodiments. This permanent module may be designed to receive variations of water quality. A semi-permanent module 922 provides more than one use, for example a month's worth of uses, but is disposable periodically or upon detection of incipient failure. The permanent module may contain a controller to enforce the proper use and handling of the semi-permanent module since safeguards must be enforced with regard to it. But with the semi-permanent modules, as discussed below in connection with particular embodiments, the procedures do not involve washing, cleansing, sterilization. The final stage includes final filtration and/or treatment steps provided in a single-use element 924. In the final stage, the least expensive components may be arranged to guard against sterility failures of the upstream components. As will be seen, the preferred embodiments described herein conform to this model. Variations of the model are possible including fragmenting the intermediate modules into ones used according to other schedules such as one module replaced monthly and another replaced weekly. An example of a semi-permanent element and a control system to safeguard against contamination are shown in FIG. 1B. Note that the embodiment of FIG. 1B may constitute an independent invention and need not be employed in a combination as discussed with reference to FIG. 1A, although this identified as a preferred configuration. Referring to FIG. 1B, a pump 416 feeds raw water into a filter module 425 via an input line 403. The filter module 425 contains first and second filters 410A and 410B. In an embodiment, the first and second filter stages 410A and 410B are deionizing filters. The first and second filter stages 410A and 410B may be accompanied by other types of filters (not shown here but discussed and illustrated elsewhere in the instant specification) in the filter module or externally thereto to perform a complete water treatment. Treated water is supplied to a batch container 417, which may or may not be present. In the illustrated configuration, water is treated for preparation of a medicament which may be included in concentrate form in the batch container 417 as a presterilized consumable unit.

Note that further embodiments of a container for storing a batch of treatment fluid are discussed above and below and all of these embodiments are considered to permit the use of concentrate stored and shipped within the batch container or separately in a different container. These are alternative embodiments.

Between the first and second filter stages 410A and 410B, a water quality sensor 405 is provided. In an embodiment, the water quality sensor 405 is a conductivity or resistivity probe that detects ionic species in the water after passing through the first stage filter 410A. In a preferred embodiment, the second stage 410B provides at least some redundancy in that the second stage 410B provides some of the filtration effect of the first stage 410A. In an alternative embodiment it provides all of the filtration of the first stage 410A and is thereby completely redundant. In such an arrangement, the first stage would expire (become depleted), allowing contaminants to break through, before the second stage expires. The contaminant breakthrough is detected by a controller 415 connected to the water quality sensor 405. The controller 415 also controls the pump 416. Upon expiration of the first stage 410A, the controller allows the preparation to continue until a certain amount of fluid is collected in batch container 417, preferably an amount required for a treatment. Once this threshold quantity is delivered, the controller will not allow the pump 416 to be started until the filter module 425 is exchanged with a fresh one. The second stage filter 410B, preferably, is sized to ensure that, by itself, it can purify at least a single batch of water, plus a safety margin without any contaminant breakthrough to the output line 404. In a preferred embodiment, the second stage filter 410B is a smaller size than the first 410A. In the preferred embodiment, the second stage filter 410B may be of a different type which may not be as able to handle high contamination loads as the first 410A. This may be acceptable because, although after breakthrough is detected, the emerging fluid is still substantially purified and the load input to the second stage filter 410B may remain low until a single batch of fluid is prepared.

In an alternative embodiment, the filter module 425 is provided with a permanently attached data carrier 423 such as radio frequency identification device (RFID), bar code (1- or 2-dimensional), contact-type identification device, etc. The data carrier 423 contains a unique identifier of the filter module. When a cartridge is connected to the pump, the controller 415 reads the data carrier 423 using a reader device 422 and stores the identifier in a memory 437. If the water quality sensor 405 indicates contaminant breakthrough, the controller permanently stores the identifier in an expired directory in the memory, which has a non-volatile portion for the directory. If a user attempts to connect a module 425 with an identifier stored in the directory, the controller will not operate the pump and will indicate the error condition by means of an annunciator 420 or equivalent device, such as an LCD display message.

Note that in an alternative device, the data carrier 423 is a programmable device with a writable memory. In this embodiment, the controller 415 programs the data carrier 423 with a flag indicating that the filter module 425 is expired. The controller 415 then prevents the initiation of a new batch.

FIG. 1B also illustrates an optional embodiment with a pressure transducer 435 that may be used to test for clogging of the first stage filter 410A. When the pump 416 head pressure reaches a particular maximum, in order to allow a batch preparation to be completed, the controller activates a normally-closed valve 426 to bypass the first filter stage 410A. Water flows through a bypass line 427 and through the second stage filter 410B. The expiration of the filter module 425 may then be enforced by the controller in either of the ways described above. The above embodiment may be used in filter modules 425 that contain filters that clog when depleted such as carbon filters or porous membrane filters. Not that the clogging and breakthrough devices described above may be combined or used exclusively in a given filter module embodiment. Note also that the head pressure may be sampled and stored over a period of time to determine if the pressure change profile is characteristic of a filter suffering normal usage. This would distinguish, for example, an accidental line blockage and prevent inappropriate use of the bypass line 427.

Figure 2A:
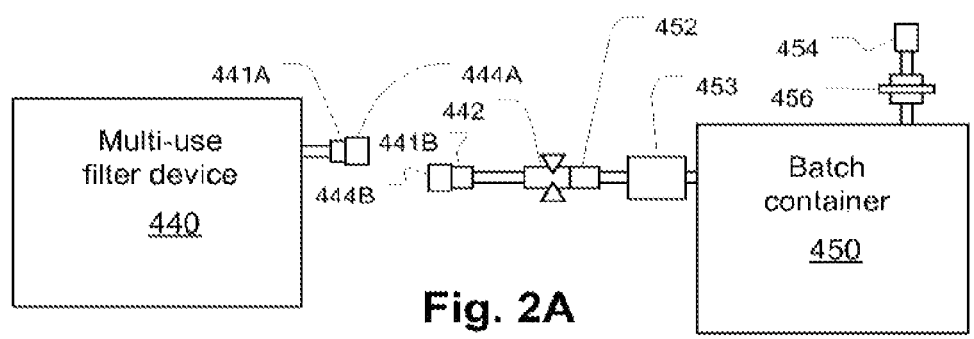
FIGS. 2A and 2B illustrate a filter and batch container with connector systems that ensure against contamination.
Figure 2B:
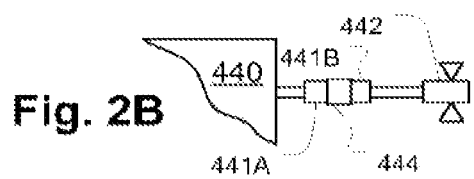

Referring to FIGS. 2A and 2B, a multi-use filter device 440 has an outlet port 441A with a cap 444A to avoid contamination. The outlet port 441A is connectable to a mating port 441B, which is also capped (cap 444B). The ports 441A and 441B may be, for example, locking luer connectors. A special clamping connector 442, which seals itself when disconnected from a mating connector 452 is connected to port 441B and a line connecting it to a batch container 450 which receives purified water from the multi-use filter device 440. A microporous filter 453 guards against the introduction of contaminants by touch contamination when connectors 441A and 441B are mated.

Figure 3:
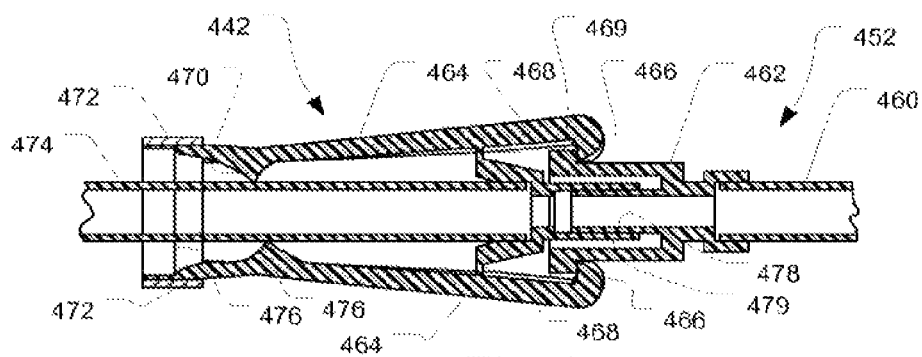
FIG. 3 illustrates a self-clamping connector.

The special clamping connector 442 may any suitable device that seals off, to prevent contamination. An embodiment of such a connector is shown in FIG. 3, although the sealing and disconnecting functions, to be described below, can be performed by separate mechanisms so this embodiment is not essential. An outlet tube 460 connectable to the filter 453 of FIG. 2A is permanently affixed to a male luer fitting 478 of a male connector 452 that is received by a female luer fitting 479 of a female connector 442. The female connector 442 has a pair of latch arms 464 that engage a ridge 469 of the male connector 452. The latch arms 464 pivot on living hinges 468 affixed to the female luer fitting 479. Pinching ridges 470 and 476 compress the tube 474 when a bendable retaining ring 472 is squeezed. At the same time, engaging ends 466 of the latch arms 464 retract from the ridge 469 releasing the male luer connector 452. The bendable retaining ring 472 retains its deformed shape once it is pinched so that the tube 474 remains pinched and thereby sealed when the connectors 442 and 452 are disconnected. The bendable retaining ring 472 may be made of ductile metal, for example. The retaining ring 472 may be replaced by another suitable device such as a ratchet mechanism.

Returning to FIGS. 2A and 2B, when the multi-use filter device 440 is first used, its outlet connector 441A is sealed with a cap 444A as is the inlet connector 442 (with cap 444B) of the batch container 450. The batch container 450 may be sealed and sterilized with the special fitting 442 and its mating connector 452, which may correspond to elements 442 and 452 in FIG. 3, connected in a completely sealed and pre-sterilized state. Other ports such as a sampling port 454 may also be sealed and, if only used as outlets, protected from intrusion of fluid by means of a check valve 456 and/or another membrane filter 453 (not shown separately). The first time the batch container 450 is connected to the multi-use filter device, the caps 444A and 444B are removed and the connectors 441A and 441B mated. After filtered water is collected in the batch container 450, the special clamping connector 442 is disconnected and left connected to the multi-use filter device 440 to keep it sealed and free from contamination as shown in FIG. 2B. The second time the multi-use filter device 440 is used, the special clamping connector 442 is removed by means of the connector pair 441A and 441B and discarded while a new batch container's 450 connector 441B is mated to the pre-existing multi-use filter device's 440 outlet connector 441A. The connector 441B carries a new special clamping connector 442 and the same process can be repeated.

Figure 4:
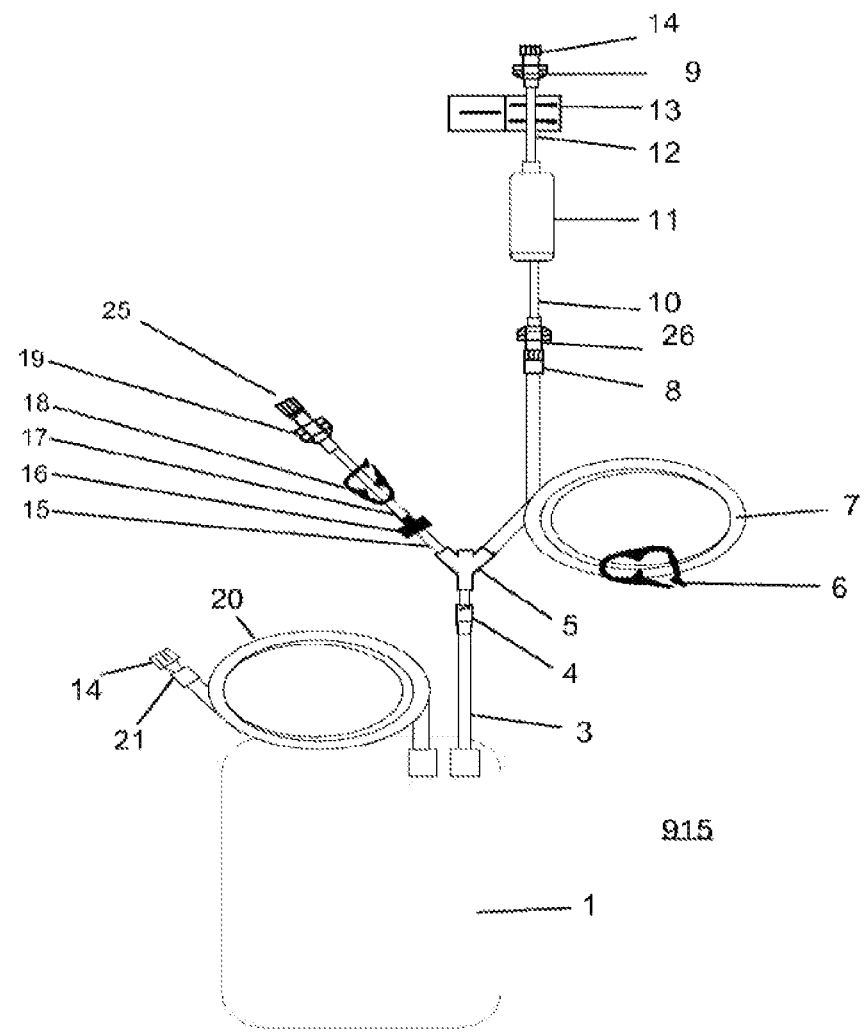
FIG. 4 illustrates a batch container tubing set.

FIG. 4 shows an embodiment of a batch container, for example one that may be used with the foregoing embodiments, but in particular, with the above embodiments. The batch container 1 has a batch container, proper, 1, a break-off female luer lock connector 4, a y-connector, 5, a pinch clamp 6, a male luer 8, a female luer 26, a sterile filter (e.g., 0.22 micron pore or pyrogen filter) 11, a non reopenable tubing clamp 13, a non-breathing cap 14 on a female luer 9. Line 15 has an in-line check valve 16, a pinch clamp 18, a break-off male luer cap 25 and female luer 19, and a female luer 21. Various tubing branches 3, 7, 10, 12, 15, 17, and 20 connect these elements. The batch container 1 is delivered to a patient treatment setting as a sealed sterile container with all terminals sealed. The batch container 1 may contain, as delivered, a concentrate solution sufficient to create a treatment batch of fluid, such as dialysate or replacement fluid, when water is added. Concentrate may be added by means of the luer connector 21. In the tubing set delivered to the treatment site, the tubing branch 20 may be sealed and cut after the concentrate is added. Water is added at the treatment site through connection to a water source via luer 9. The water is preferably metered to provide a predefined quantity. The sterile filters should be sufficient to protect against contamination by pyrogens before water is added to the batch container 1. A sample of diluted treatment fluid may be drawn through the luer 19 before treatment. The check valve 16 prevents any contamination due to backflow from the sampling procedure. After water is added to the treatment fluid container 1, the luer 9 is disconnected from the male luer 8 and the male luer connector connected to the blood treatment system. Luer connectors are shown by way of example as are other features and these are not essential to all embodiments.

Figure 5:
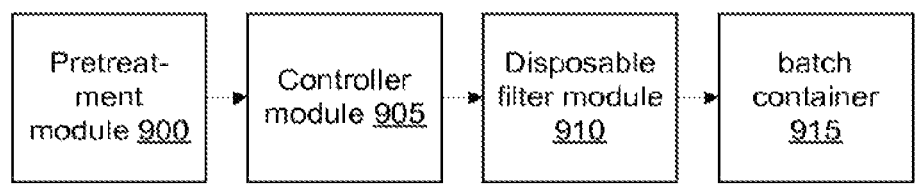
FIG. 5 illustrates a fluid preparation apparatus embodiment in a figurative way for discussing various features and arrangements of a water purification system.

FIG. 5 illustrates another arrangement of a particular embodiment whose description follows. A pretreatment module 900 provides primary filtration from a raw water supply, for example tap water and feeds prefiltered water to a controller module 905 which provides various control functions, a pump, pressure detection and control, and permanent filtering capabilities which are not shown separately here. Water is metered by the control module into a consumable disposable module 910 which may provide deionization, adsorption filtration, microporous filtering, chemical pretreatment, etc. and any other types of filtering that may require replacement of components. The purified water is finally conveyed to the batch container circuit 915 discussed with reference to FIG. 4.

Figure 6:
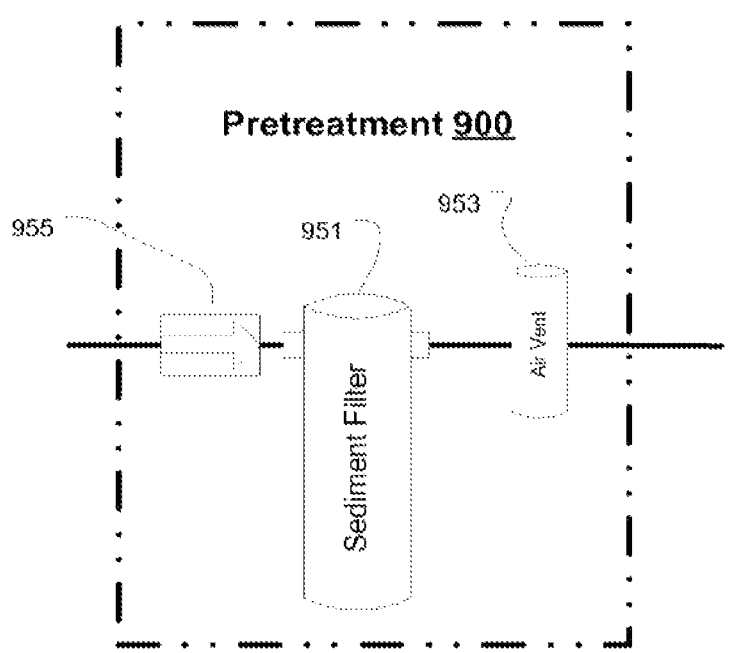
FIGS. 6, 7, and 8A illustrate portions of an embodiment of a fluid preparation apparatus.

Referring to FIG. 6, pretreatment module 900 is shown in more detail. A check valve 955 prevents backflow. An air vent 953 removes air from the primary supply and a sediment filter 951 (which may be replaceable) provides substantial filtering of solids.

Figure 7:
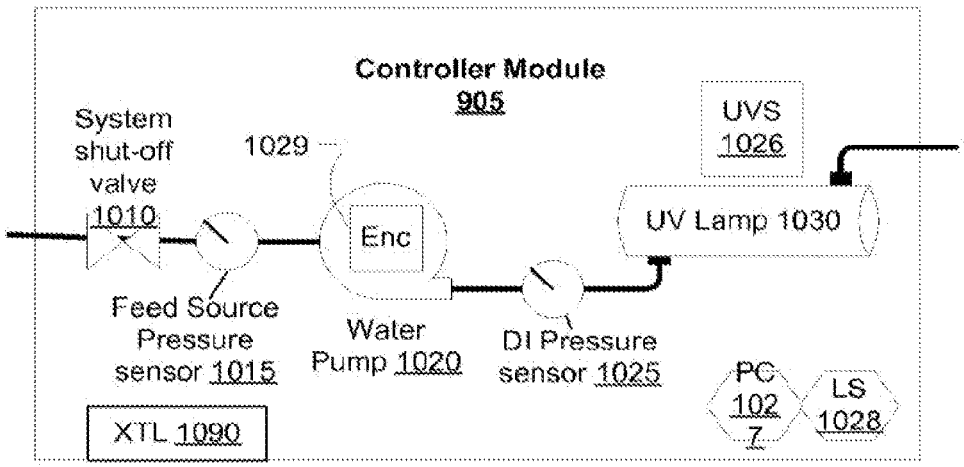

Referring to FIG. 7, the control module 905 is shown in greater detail. A shutoff valve 1010 is provided for safety. Pressure indicators 1015 and 1025 may be provided for monitoring the respective pressures in and out of a pump 1020. Feedback regulation may be provided to ensure that consistent metering is provided if the pump is relied upon for measuring the total quantity of water supplied to the batch container 1. A high intensity ultraviolet (UV) lamp 1030 provides a both sterilization mechanism and a mechanism for removing chlorine and chloramines. Preferably, the UV lamp 1030 is of such intensity and wavelength as to provide disintegration of chloramines. In a preferred embodiment, the lamp is characterized by a 245 nm wavelength and an output power of 750 mJ/cm$^2$ up to 1500 mJ/cm$^2$ which is sufficient to remove chloramines. By oxidizing chloramines and subsequently, as described below, filtering using a deionizing filter, chloramines can be removed.

Note that pressure indicators 1015 and 1025 may be pressure transducers that feed control signals to a control device such as discussed with reference to FIG. 1B and to be discussed with reference to FIGS. 13A and 13B. The operation of pump 1020 may be controlled in dependence on pressure indications from such transducers. For example, if a high head pressure is indicated, an alarm may be indicated and the pump shut down. This may indicate a problem with a connected filter. Also, the pump may be operated for a short interval and a pressure decay profile recorded and compared with an expected decay profile. If the profile does not match, it could be used to indicate a leak (such as in a filter or line) or a clog in the system. If the upstream pressure goes low, it could mean that the water supply is turned off or some other fault. Each of these events may be indicated by means of an annunciator or display (e.g., see 330 and 380 at FIGS. 13A and 13B and attending discussion) and/or by switching off the pump to avoid damage to the system and to notify the operator to take corrective action.

Figure 8A:
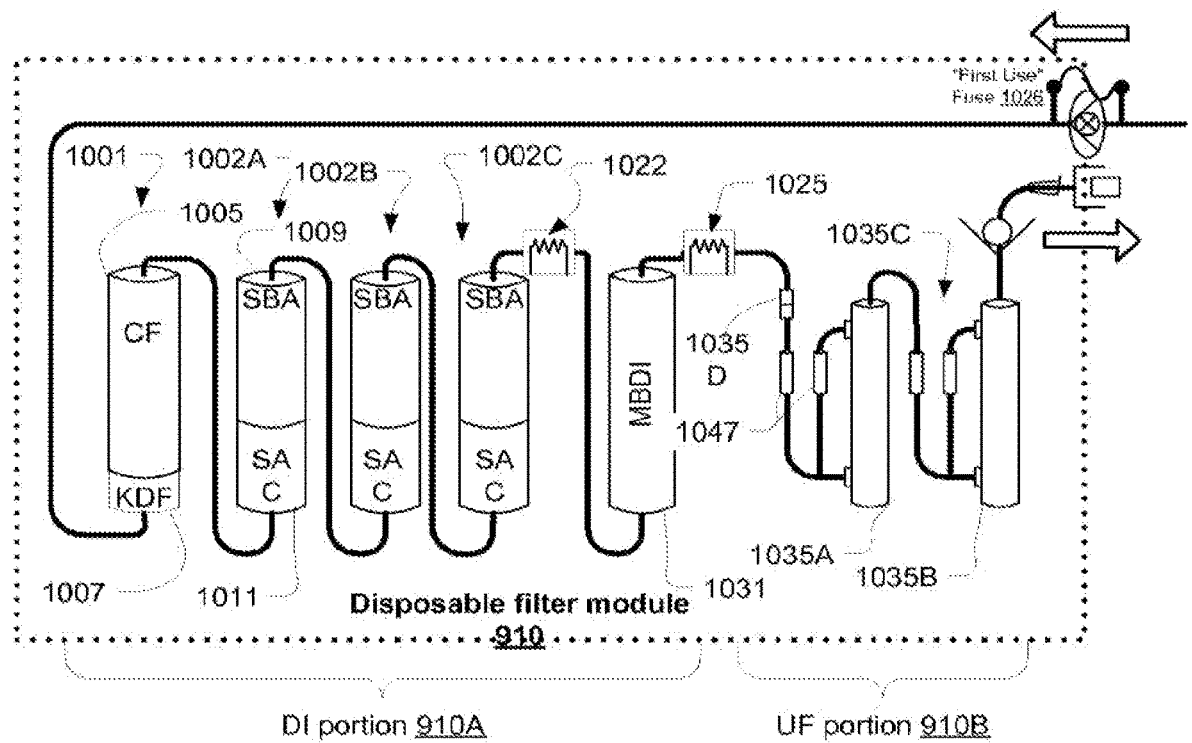

Referring to FIG. 8A, the replaceable (disposable or remanufacturable) filter module 910 contains a first stage filter 1007 copper-zinc alloy which is used to subject the water to a reduction/oxidation process to remove ions. This removes ions through a chemical reaction. An embodiment is KDF 85 media where about one pound is used for a flow rate of 150 ml./min water flow rate. A activated carbon filter 1005 follows which is a well-known adsorption type filter. Next three stages of strong acid cation (SAC) 1011 and strong base anion (SBA) 1009 filters follow in series. The SAC/SBA filter cartridges 1011/1009 are not mixed beds as typically used in water filtration applications. They separate the cation and anion stages as illustrated because it has been determined to be much more effective at removing colloidal aluminum from the treated water. Note that the order of the SCA and SBA beds is not limited to what is shown and that they can be housed in a single canister or multiple canisters. Also note that other components can be sequenced differently as well as should be clear from this disclosure. For example, it should be clear that the pump 1020 can be used in a pushing arrangement to draw water through the UV lamp and the particulars of the arrangement are not limiting to the inventions disclosed. Also note that the resistivity probe 1022 can be included within a single deionizing filter between previous and following deionization stages and employed to similar effect. In such an embodiment, a deionizing filter would have leads or contacts to connect the probe to an external measurement device or controller.

Note that instead of using layered beds in a single cartridge as described, separate cartridges each containing one of a SBA and SAC filter bed may be used. Also, each cartridge could contain more than one layer of each to provide similar results.

The resistivity probe 1022 detects ion concentration by contact testing of the resistivity of the water. A signal is generated to indicate that this will be the last allowed batch before the system will require the replacement of the replaceable module 910. Control may be provided as in the embodiment of FIG. 1B, discussed above. The second filter in the present embodiment, which backs up the first stage suffering from breakthrough, is a mixed bed deionization filter 1031. This ensures that the current batch can be completed. A second, final safeguard resistivity or conductivity test is provided with an audible alarm at 1025 as a back up safety measure. If the value it detects is above a certain level, the pump 1020 may be shut off and an alarm sounded. This may come into play if the resistivity probe 1022 fails, or if the safeguards discussed with reference to FIG. 1B are breached. TP (for "transducer protector") is a hydrophobic membrane air vent which allows air in ultrafilters 1035A and 1035B to be purged. The ultrafilters 1035A and 1035B may be a microtubular filter such as used for dialysis. An air vent may also be provided as shown at 1047. The air vent may, for example, have a 1.2 micron hydrophilic membrane that blocks air. There is a hydrophobic membrane port which allows air to vent from the filter. These are available as off the shelf components. Any suitable air elimination device may be used and these features are non-limiting of the described embodiments. Also, the second stage MBDI type filter 1031 can be a layered deionization filter such as 1002C with the same benefits as described in terms of providing protection against breakthrough. Also, the final resistivity sensor 1025 can be located as shown or moved to another location downstream of the final deionization stage, such as after or between the ultrafilters 1035A and 1035B, and the configuration shown is not limiting of the invention.

Filter module 910 preferably constitutes a multiple-use component which is replaced after multiple batches of purified water have been generated and consumed over an interval of time. As stated elsewhere, the period of time may be on the order of a month and the number of batches may cover 3-7 treatments per week over that interval. In the filter module 910, the deionization (DI) portion 910A is isolated from the sterile output by the ultrafilter portion 910B, thereby avoiding one of the problems and risks associated with conventional filters, namely, sterilization of filter media in-place. The module 910 is preferably delivered as a sealed unit with the ultrafilter portion 910B completely sterilized, including a bridging line 1035B running between the two ultrafilters 1035A and 1035B.

Since the ultrafilter portion 910B employs ultrafilters 1035A and 1035B which sterilize any fluid passing through them, the DI portion 910A does not need to be sterilized to ensure that the water output from the filter module 910 is sterile and infusible with suitably low rates of pyrogens. Again, by providing that the media of the filters 1035A and 1035B are separated by a physical distance predetermined to prevent grow-through over the expected usage interval of the filter module 910, any contamination from the DI portion 910A growing through the media of the first filter 1035A could not reach the output of the filter module 910 by growing to, and through, the second filter 1035B. The benefit of providing a multi-use filter module with the protection of such a sterile filter portion is not limited to DI filtration. For example, the multi-use disposable filter module 910 could have a reverse osmosis portion, instead of the DI portion 910A, which is similarly isolated from the sterile outlet by ultrafilters 1035A and 1035B.

The ultrafilters 1035A and 1035B may be pre-connected and sealed as a unit before sterilizing. A connection between the DI portion 910A and the ultrafilter portion 910B can thereafter be made using a connector 1035D. Since the DI portion 910A remains dry until the first use, the filter module 910 can be preassembled with the connector 1035D mated. If another type of filter, which may need to be wet, is used in place of, or in addition to, the DI portion 910A and is located similarly upstream of this portion, then the connector 1035D can be left unmated until the filter module 910 is initially used. Thereafter, the ultrafilter portion 910B can provide protection for the contemplated use interval of the filter module 910.

Note, it should be clear that resistivity probe 1022 may be used in a configuration such as that of FIG. 1B, with the resistivity probe 1022 corresponding to sensor 405 such that filter module 910 corresponds to filter module 425.

A simple device for enforcing against re-use or use of an expired device is to employ a fuse that the system burns out when a component is first used. For example, the disposable filter module 910 described with reference to FIG. 8A may be fitted with a fuse 1026 that is burned out when first connected to the controller module. The condition of the fuse can be detected if the same module is later connected to the controller and the controller may the prevent its re-use. In a broad sense, such a fuse embodiment may be considered a type of data carrier whose state is changed to indicate a first use. The same device may be used when the module is determined to have been expired, for example if a contaminant break-through is detected by resistivity sensor 1022. Thereafter, the disposable filter module 910 may be prevented by the controller from being used after an attempt to reconnect by burning out a fuse or updating a data carrier to indicate the break-through ("expired") status.

Note that two separately-housed ultrafilters 1035A and 1035B are serially interconnected. The separate housings ensure against failure mechanisms such as grow-through of pathogens, adjacent simultaneous or shared seal failure. For example, prior art reference US Patent Publication No. 2004/0105435, cited in the Background section, shows a filter cartridge with two microporous membranes in adjacent layers of a filter cartridge housing. These may share a seal mechanism or adjacent seals such that failure of the seal of one necessarily involves failure of the seal of the other. Also once a grow through problem occurs in one, the adjacency may cause the problem to creep directly into the adjacent membrane. These problems are prevented by the illustrated arrangement of separate redundant ultrafilters.

Figure 8B:
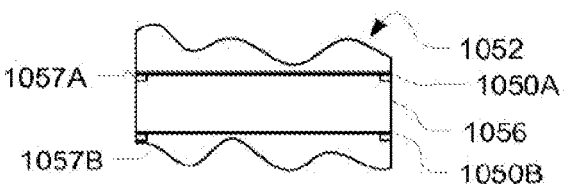
FIG. 8B illustrates a portion of a filter module in which two redundant ultrafiltration membranes are commonly housed.

Note that the benefit of separately housed filters may be substantially provided in a single housing by substantially separating two ultrafilter layers. Referring to FIG. 8B, for example, a multilayer filter with various types of filter elements housed in a common cartridge 1052 contains two ultrafilter layers 1050A and 1050B. The two ultrafilter layers 1050A and 1050B, separate membranes, are kept apart my an intermediate layer 1056, which may be a spacer or another filter medium. Separate seals 1057A and 1057B, which are also spaced apart, are provided.

Note the final conductivity/resistivity sensor/alarm 1025 may control the pump, as noted. A controller 1090 may be connectable to the disposable filter module 910 and configured to stop the pump 1020. The trigger resistivity safety level to cut-off the pump 1020 may be 1 megohm, but may be raised to 2 megohm to allow the use of required temperature compensated resistivity probes (an FDA & AAMI requirement) This does allow use of low cost in-line resistivity probes in the disposable filter module 910.

Preferably, the filter module 910 as well as the modules of other embodiments are of such a flow rate that upward flow of fluids is possible. Generally, prior art deionization beds suffer from the problem of floating or loosening resin particles which may have been disturbed during handling. The separation and floating of the particles breaks up the beds and renders the filters less effective. To avoid this, generally, filter systems are configured to direct flow downwardly through the beds to help keep and compress the resin particles. But if flow rates are kept low, as may be done in the present system, water may be flowed in an upward direction which helps to eliminate air from stream. Air is a notorious problem in the preparation of medicaments such as dialysate. The precise flow rates needed to allow upward flow will vary according to the characteristics of the system. One way to allow faster flow rates without being hampered by break away resin particles is to provide a bed compressor of resilient porous material to compress the bed. Referring momentarily to FIG. 12, in a filter cartridge 1150, a resilient compression layer 1140 urges the filtration material 1145 in a downward direction. The resilient compression layer may be any suitable polymeric or rubberlike material that is compatible with the application.

The following is an example procedure for using the devices discussed with reference to FIG. 4.

1. Remove the dialysate concentrate tubing set 915 and remove the cap 14 from the tubing line 7 that contains the filter 11. (The 0.22 micron filter 11 provides additional protection from inadvertent contamination.)
2. Connect the outlet line 404 to the concentrate bag luer connection 9.
3. Break the frangible luer connector 4 which connector is configured to form a permanent seal on the side facing the Y-junction 5 when disconnected.
4. Add predetermined quantity of water into the concentrate bag using the purification plant through tubing branch 7 through luer connector 9.
5. Optionally a user can write on the bag label the date and time water was first added to the concentrate bag, to assist in ensuring that it is used within a period of time. An automated scheme may be employed as well.
6. Shake the batch container 1 well to mix.
7. Confirm solution conductivity prior to use. Remove the break-off cap 1 and draw sample from this branch 15. After removing the sample, clamp the line using the pinch clamp 17 provided.
8. (The following is normative according to a preferred embodiment and not limiting of the invention) Conductivity must be in the range 13.0 to 14.4 mS/cm. Nominal conductivity for the dialysate solution is 13.7 mS/cm at 25° C. If conductivity does not meet this specification do not use it. Verify that the results are accurate. If conductivity is high additional water may be added to bring it within specification. If conductivity is low then the solution must be discarded.
9. Using the non re-opening clamp 13 provided, clamp the line that is connected to the water purification plant.
10. The clamp 6 is, next, clamped on the line that is connected to the dialysate bag 1.
11. Disconnect the water source at the luer connection 26.
12. Connect the bag of dialysate solution to the dialysis circuit at the connection 8. This leaves the filter 11 and permanent clamp 13 in place to protect the water supply source.
13. Unclamp the line going to the dialysate bag using clamp 6, and initiate treatment after verifying that dialysate will be used within 24 hours from when water was added.

Referring to FIGS. 9A and 10A, a batch container 100 has a fluid quality sensor 136 of a probe 120, such as a contact-type conductivity sensor. The latter may simply be two metallic surfaces separated by a known distance and of a given area that has been calibrated. A cage 135 in a support 105 sealed to the wall 130 of the batch container 100 which may be a polymer bag as typically used in the medical industry. The cage 135 prevents an opposing wall (not shown separately) from preventing fluid from circulating around and through the cage and in contact with the probe such that a reading of the probe 120 is improved. The probe 120 extends from the support 105 and has a lead 122 with a signal connector 125 that can be connected to a controller (discussed later). The probe 120 is an independent element and can be used with any of the embodiments so its description here in combination with other features is not intended to be limiting. Note that it may be preferable that the probe assembly be permanently sealed to the batch container to prevent the possibility that contaminants can enter the batch container 100 interior.

At 110, a fitting connecting a sample or feed line 145 is shown. The latter may be used, with a connector 156, connect a sampling syringe to draw out a sample of a medicament or infusate. A check valve may be provided at 155 to prevent ingress of contaminants. A clamp (not shown separately) may be provided as well to guard against contamination. In an alternative embodiment, line 145 may be configured for injecting a soluble concentrate into the batch container 100 before the container 100 is sealed and sterilized as a unit (for example, by gamma ray sterilization). When a prescribed quantity of purified water is added to the batch container, the diluted concentrate may form a medicament or infusate such as replacement fluid for hemofiltration or a dialysate for hemodialysis. Line 145 may also represent a draw line that may be connected to a treatment machine. In the latter case, a sterile filter (at 155), such as a microporous membrane of 0.2μ may be provided to guard against touch contamination. Additionally, a clamp may be provided as at 155.

In the embodiment of FIG. 9A, purified water may be added to the batch container by another instance of a line similar to 145. Alternatively, if concentrate or other medical solute or medication is contained in a separate container, such may be added to the batch container 100 by means of a double lumen spike 174. (Details of a suitable dual lumen spike can be found in US Patent Publication No. 2004/0222139, which is hereby incorporated by reference as if set for in its entirety herein). A spikable bag 170 contains, for example, medical fluid concentrate such as concentrated dialysate. Purified water is pumped through connector 182 of line 180 and passed into the bag (after spiking) by the dual lumen spike 174. The fluid circulates in the bag carrying its contents back through the dual lumen spike 174 through line 172, through a filter 150 into the batch container. The dual lumen spike may be sealed by means of a removable cap 175 so that the batch container and fluid lines can be sealed and sterilized and later delivered as a unit without contamination. Clamps 157 may be provided to seal the batch container 100. A special clamping connector 452 may be provided and used as discussed with reference to FIG. 3 in line 180. If concentrate is present in the batch container 100 rather than using a spiking bag 170, the concentrate may be used to obtain a data point for a calibration line fit for measuring fluid conductivity.

Referring to FIG. 9B, instead of providing a conductivity or resistivity sensor in the batch container 100, a dual lumen takeoff 255 with a common lumen (Y-configuration) 260 housing a water quality sensor 262 of a probe 210 with corresponding signal connector 220 and lead 215. A syringe port 240 and check valve 242 are connected inline to the other branch of the Y-junction. When a syringe (not shown) is attached and fluid drawn into it, fluid from the batch container passes over the water quality sensor to allow its quality to be measured. In other respects the elements of FIG. 9B are the same (and identically numbered) as those in FIG. 9A.

Referring to FIG. 11, a replaceable multiple use filter module 1125 as may be used in the various embodiments described herein has an inlet port 1130 and an outlet port 1110. A physical arrangement of filter cartridges 1111 is shown which provides for a compact module 1125 that is advantageous for packaging and assembling to a chassis (as discussed relative to FIGS. 13A and 13B). Tubing 1116 runs from the top of each cartridge 1111 to the bottom to provide upward flow as discussed earlier. A signal port 1100 for reading fluid quality sensors 1115 and 1105 is provided in a housing. 1127. Signal port 1100 may have a lead wire and connector installed to it or one may be provided separately. Alternatively, signal port 1100 may be a wireless port powered by a battery. Signal port 1100 may include a data carrier as discussed with reference to FIG. 1B or a data carrier may be provided separately or without the signal port if a fluid quality sensor is not provided.

A data carrier may include software and instructions for using the filter module 1125. These may be read by a permanent component of a filtering system as described in connection with FIGS. 13A and 13B. A base unit 335 may be configured substantially as described with reference to FIG. 5 with the base unit 335 housing the components of the permanent pretreatment module 900 and controller module 905. The base unit may contain a display 330, such as an LCD display. Instead of, or in addition to, a display, the base unit (and other embodiments described herein) may have a voice generator or other type of output device. An inlet port 341 may be provided for receiving raw water to be filtered and an outlet port 340 for attachment to a filter module (which may be multi- or single-use) which is received in a locating station 315. The latter may have a reader 311 to read a data carrier or to connect with a fluid quality probe such as one or more conductivity sensors described above. A further locating station may be provided such as 305 for a batch container. This may have a data carrier reader 320 and/or various other components (at 321) such as a heater, a mixer, such as a moving field generator for magnetohydrodynamic mixing of the contents of an installed batch container. The base unit 335 may have a port 310 for connection to a fluid quality probe of the batch container. This may provide a calibration input as well as a final measurement of fluid quality. The embodiment of FIG. 13B additionally provides a locating station for a concentrate container such as 170 described with reference to FIG. 9A. The base unit 335 may further be fitted with a controller containing a computer with a connection to the Internet or other network connecting the base unit with a server 390.

In an embodiment, features indicated at 301-306 may be added to allow the base unit 335 to control when and whether an outlet line of a batch container should be opened and clamped. A batch container is fitted in the station 305 and an outlet line of the batch container fitted between clamping portions 303 and 304. A detector 306 verifies that the line has been fitted in place. When the system is run, an actuator 302 and motor 301 may be activated to clamp the line during fluid purification and as the batch container is filled. After the batch is filled, the clamp may remain closed until a treatment operation, which may be run while the batch container remains in place, is begun. At treatment time, the clamp mechanism 303 and 304 can enforce the expiration time of the batch of fluid. For example, a timer can be started within the controller of the base unit or, equivalently, a time/date stamp stored and the clamp only released if the batch of fluid is used for treatment within a certain period of time. For this purpose a treatment machine and the base unit 335 may be combined into a single device under common control or the two may be linked by a data link to operate cooperatively to achieve such a result. The flow chart of FIG. 15 describes the control steps involved.

Referring now to FIGS. 9A and 10B, instead of a concentrate container in the form a spikable bag 170 as illustrated in connection with FIGS. 9A and 9B, a cartridge 271 as illustrated in FIG. 10B may be used. Here, concentrate 280 is within a sealed cylinder 274 with a piston 273 and a burstable seal membrane 275. The cartridge may be fitted in the base unit 335 (FIGS. 13A and 13B) which may contain a linear drive 270 and plunger 272 to push the piston 273 thereby bursting the seal membrane 275 and inject contents into a T-junction 278 in the path of purified water sent into the batch container 100. Note that the cartridge 271 may be provided as part of the sterile batch container fluid circuit shown in FIG. 9B.

Figure 15:
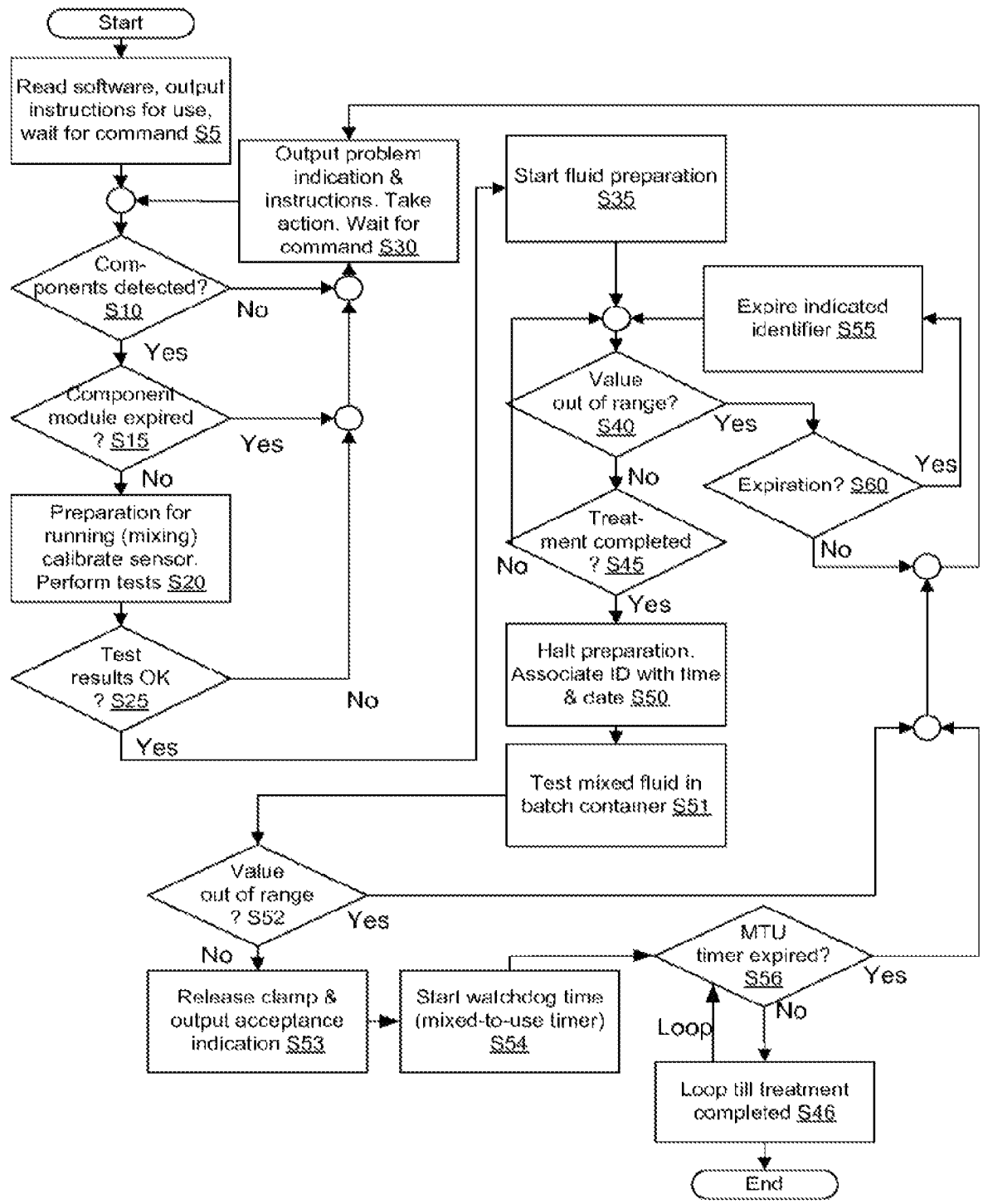
FIG. 15 is a flow chart for discussing various control options of the various embodiments discussed herein.

Referring to FIGS. 14 and 15, the base unit 335 (FIG. 13A) and corresponding parts of other embodiments described herein, may contain a programmable controller including an embedded computer 600 with memory, non-volatile storage, communication elements, etc. Various sensors 605 such as discussed in connection with various embodiments may be connected to provide input to the controller executing a program stored in memory. The latter may stored in firmware or obtained from a data carrier via a data port 610 as described previously. In addition, a network or Internet connection to a server 625 may be provided to obtain and transmit data such as software, instructions for use, expired identification codes, etc. Actuators 615 such as valve clamps, pumps, and annunciators 620 such as alarms may be provided as well.

A sample program for operating the various embodiments described herein is shown in FIG. 15. The process may begin with firmware until software loaded at a later stage takes over. Software may be read from a data port or data store and instructions for using the system output at step S5 whereupon the system waits for user input. The instructions may indicate to press hard or soft key to continue at which point steps S10 and S15 are executed to determine if a no-go condition exists. If a necessary component (S10) has not been connected, step S30 will be executed and the system may output an appropriate message to instruct the user to take corrective action and wait for response. Similarly, if in step S15, it is determined that a component is expired, such as a batch bag that has been previously used or a filter module has been used and previously indicated as having suffered breakthrough, step S30 will be executed. At step S20, various system tests may be performed such as a pressure profile test or quality test. Tests may also include determining if the conductivity indicated by a connected conductivity probe is within specified limits. In step S25 it is determined if all tests have been passed and control passes to step S35 where fluid preparation is begun. If not, step S30 is performed and appropriate output is generated on a display such as 330. If a value goes out of range at step S40, control passes to step S60 to determine if an expiration event has occurred, for example, breakthrough of contaminants in a filter module. Note that Filter modules may be "stamped" (speaking figuratively) with a permitted time of use after a first use when presumably the seal was first broken. This may be enforced in the same manner as discussed with reference to attempted reuse of a filter module after breakthrough was detected. Thus, step such an event may be detected at step S60 as well.

At step S55 depending on the type of data carrier (e.g., programmable or just carrying a unique ID), the expired or spent unit is indicated as expired so that reuse can be prevented. For example, in S55 the data carrier may be programmed with a token to indicate that the attached filter module is expired or a server may be sent a message to indicate that its unique ID should be added to a list of expired IDs. Any suitable device may be used to "expire" a unit. Since expiring a unit may still allow a batch to be prepared, control returns to S40. Completion of the treatment may be determined at step S45 by measuring the total mass pumped or by other means. For example, if the embodiment provides a conductivity probe in the batch container, step S45 may depend on the measured conductivity of the batch contents. Once completion is determined, the system may be halted at step S50 and the batch bag "stamped" with a time and date. Note that further instructions may be output at this point.

In one embodiment, the water purification and treatment may be done from a single apparatus and under common control. The steps following step S50 illustrate this. Assuming purified fluid has been added to a batch container of some description such as those described in the current specification or some other, the contents of the container may be mixed, if a solute is involved, and the contents checked in some way in step S51. For example, the conductivity of a mixed batch or the resistivity of a pure batch can be checked determine its conformity with treatment specifications. In step S52, if a value is out of range, control passes to step S30, but if not, the batch may be utilized at any time up to an expiration time/date (MTU time, or Mixed Till Use-time). In step S53, an outlet clamp that prevents fluid from being drawn from the batch container is released to allow a treatment to be performed with the fluid product. At the same time, an acceptance message can be output to the user on a display. At this time, in S54, a time stamp is stored or a timer started to keep track of the expiration of the batch of fluid. If the expiration is not observed, which is tested at step S56 by checking to see if the timer has expired, the clamp will close in step S30 (under the general step indicated as "take action") and an appropriate message output. The system will then wait until treatment is completed while, optionally, continuously checking the MTU timer in steps S46 and S56.

Note that many of the described mechanical and control features are novel and inventive alone, as subcombinations with other features and their description in combination in the above embodiments is not intended to be interpreted as limiting of the inventions disclosed herein. Referring to FIG. 16, when a treatment machine 700 attempts to use a batch container 710 tagged with an expiration date at step S50, it can determine if the date has passed and prevent use of an expired batch container thereafter. This may be implemented with contact or wireless data reading devices, a programmed smart card type device or via an Internet server as described with reference to the mechanism for enforcing non-reuse of filter modules.

Referring to FIG. 17, air may evolve from fluid as it passes through an ultrafilter 714. Preferably, the ultrafilter 714 has a high membrane surface and in such filters, the potential for air evolution may be fairly high. To avoid problems with bubbles forming in the filter, the embodiment of FIG. 8A shows transducer protectors TP, which are hydrophobic air vents. But the lines leading to them can fill with water and render them useless for air purging. A refinement of the configuration of FIG. 8A, which may be used in any water treatment plant as a final protective stage, is to provide an ultrafilter 714 (which may be a standard dialyzer capped at the lower blood port) with an inlet 712 and outlet 704 on one side of the membrane connected by a return line 704 flowing through an air filter/vent 706, through further line 708 into a T-junction 717 and back into the inlet line 712. Ultrafiltered fluid is drawn out through line 707. Again, the filter/vent 706 may be a 1.2 micron air vent with a 0.3 micron hydrophilic membrane that blocks air and a hydrophobic membrane port which allows air to vent from the filter. These are available as off the shelf components. The water column defined by line 708 is denser than the corresponding column within the housing of ultrafilter 714 so that a return flow will exist through the branch 704, 706, 708. The reason for the lower density is due to the evolution of air in the ultrafilter 714.

An alternative design that integrates air vent configurations into the housing of the ultrafilter 714 is shown in FIG. 17A. For the outlet (filtrate) side of the media, an air vent, e.g., a hydrophobic membrane type air vent 765 may be integrated into the outlet of an ultrafilter 715 and an air filter such as a hydrophilic air filter membrane 766 integrated into the outlet. Any bubbles coming out of fluid collect at the top of the filtrate side (in a header space of a microtubular membrane type filter) and be vented by the hydrophobic air vent 765. On the inlet side of the ultrafilter 715 (the side of the filter media that has not yet been ultrafiltered), air collecting in the inlet side will leave by an air vent 467, for example one using a hydrophobic membrane 469. A check valve 742 may be provided to prevent siphoning and/or reduce risk of contamination.

Referring to FIG. 18, to address any problem with inadequate flow through the return branch of the FIG. 17 embodiment, a resilient channel element 730 such as an inline bladder 731 may be included with check valves 725 and 728. When the system pumps fluid, the resilient channel element 730 stores fluid under pressure and releases it in pumping fashion when the system stops pumping. Again, an air filter/vent 724 allows air to escape and purged from the return line 726. The return flow problem can also be dealt with by replacing the T-junction 717 with a Venturi device configured to create a suction in line 708 by using an accelerated fluid flow through the line 716,712.

One of the drivers for the features discussed above is a need to provide pure water irrespective of input water quality. The above embodiments are not reliant upon water quality and are designed to reliably produce pure water or solutions regardless of input water quality. Various embodiments are also designed to reduce the costs associated with lower volume (10-60 liters) preparation of medical and other pure solutions and to maintain simplicity through the combination of semi-permanent and single-use modules which combine to eliminate the complexities, costs and safety issues associated with maintenance, sterilization, and operation of many other prior art systems.

In the following sections, systems are described which is configured to prepare batches of medical fluid, such as dialysate for dialysis or replacement fluid for hemofiltration. The systems according to exemplary embodiments produce and store a single batch that contains enough fluid for multiple treatments. In a preferred embodiment, the fluid is prepared such that it has a very low rate of endotoxins and contains solutes that are compatible with storage for multiple days, such as lactate-based or bicarbonate based dialysate. The embodiment purifies water, dilutes a lactate based dialysate concentrate to form a batch, for example of 80 liter volume. The batch is stored for a specified period of time and used for frequent low-volume treatments, for example, three daily treatments. The system provides safety systems that enforce adherence to storage term constraints, purity, fluid and quality. In addition, the system strikes a unique balance between the risks long-term storage of medicaments while keeping available for immediate use, treatment frequency, volume of fluid, portability of the storage unit, and other factors to provide an overall positive impact on patient lifestyle and well-being. The features, in combination, include:

1. Frequent treatment with moderate clearance (e.g., daily) may be selected as a treatment regimen according to one preferred embodiment although this is not required;
2. Preparation of treatment fluid every several days (e.g., every three days);
3. Storage at a temperature that allows immediate fluid withdraw for treatment purposes between fluid preparation steps;
4. 1 and 2 can be accomplished with fluid volumes of 80 liters or so, for example. Such a quantity, which may also correspond to other treatment types, is a convenient quantity for a portable unit such as one that can used at a residence. Note that this volume is just an example and it is not intended as a requirement. Much more or much less could be prepared and stored based on basic system, treatment, risk, and other specifications that may vary in different applications and contexts.
5. A consequence of 2 is that the task of preparing fluid can be done at times other than treatment times (i.e., out of synch with treatments) thereby permitting a patient's schedule to be more flexible and also reducing the length of time spent performing the treatments because the preparation does not have to be done as part of any of the treatments.
6. Enabling the generating purified fluid at a patient's residence or other convenient treatment site avoids storage requirements.
7. Employing water purification based on deionization (DI) and storage at usable temperatures, combined with the high treatment-frequency and moderate clearance can reduce the demands on utility infrastructure, namely water and electrical, because the high power rates for fluid heating and high water rates associated with reverse osmosis are avoided. In other kinds of systems, high power rates are often required for sanitization of the water treatment system. DI and ultrafiltration provides a prolonged use disposable that does not require sanitization. Water usage is reduced through the use of deionization vs. RO, since this DI does not have a "waste stream".
8. The batch size permits a unitary design and, with compact packaging, may be made no higher than a household side table or no higher than about a meter and preferably no higher than about 75 cm, or the height of a typical table. In a preferred embodiment, the height is about that of a lamp or end table or about 65 cm.
9. An attractive enclosure that hides components permits an unintimidating and attractive appearance to be maintained if the treatment site is a residence.
10. The small size permits the enclosure to be made mobile and so the enclosure may be fitted with wheels.
11. A tabletop may be provided on the enclosure to allow different types of treatment equipment to be supported by it. Preferably, in keeping with the appearance objectives, the tabletop is not interrupted by protrusions such as poles, displays, and other fixtures.
12. 11, along with appropriate mechanical design features the allow the unit to output the stored fluid at a pressure similar to the normal medical fluid bags used for typical medical treatments, may permit convenient switching from a peritoneal dialysis (PD) cycler unit, until a patient's peritoneum cannot handle PD to extracorporeal blood processing simply be replacing the PD cycler with an extracorporeal device.
13. The size range for the batch container and an appropriate support mechanism and leak detection may enable the use of a disposable container to simplify preparation of the batch.
14. Filtration using deionization beds, particularly with a large safety margin, can be expensive so a long term multi-use disposable component may provide a cost balance point while also making it convenient for users because of the need to replace, for example, only once every month or even less frequently. In a preferred embodiment, the module is replaced once every 1-3 months.

15. Multi-day, multi-treatment storage, is enabled by using a lactate based treatment fluid and a pre-sterilized, disposable container with a preconnected sterile filter that treats all fluid entering the sterile, disposable storage container.

Figure 19A:
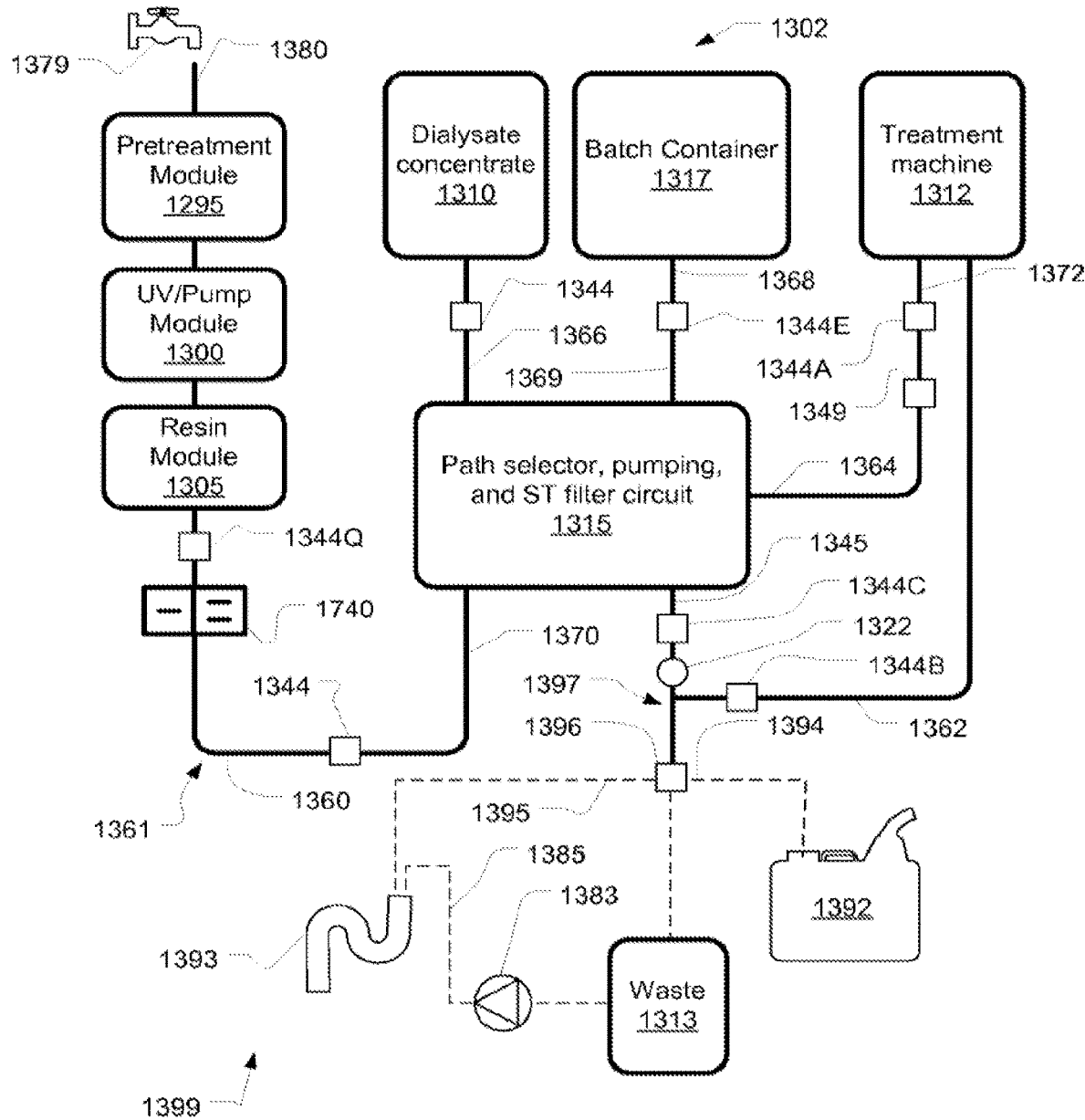
FIG. 19A is a flow diagram of a treatment fluid preparation and storage device according to an embodiment of the invention.

Referring to FIG. 19A, a preferred configuration of such a fluid preparation and storage 1302 system is shown. A pretreatment module 195 receives water from a source, such as a sink faucet 1379, and a UV/pump module 1300 may provide a semi-permanent pre-filtration process as described with reference to FIGS. 6 and 7. The water quantity requirements are preferably such that ordinary household supplies are adequate—as will be observed, the preferred embodiments described permit this. The connection to a sink faucet may be by way of a common connector that replaces the aerators of many household faucets. A long term filter (LTF) module, for example, 1305 provides water purification for multiple multi-treatment batches, for example, a capacity sufficient for daily treatments over a period of 12 weeks may be provided. This period is just an example. The module may be specified for longer or shorter intervals and may be configured to provide greater or less capacity depending on design requirements and preferences. In a preferred embodiment, the LTF module 1305 includes KDF, segregated SAC/SCA bed deionization (DI), and mixed bed and ultrafiltration as described with reference to FIGS. 2A and 8A. The LTF module, as also described above, may be in the form of a completely disposable module which only requires a small number of connections to replace. Various connectors are shown at 1344.

A disposable circuit 1303 includes a batch bag 1317, and various fluid circuit elements. Beginning with the connector 1344 for connecting to the LTF module 1305, a dongle 1361 has of a tubing segment 1360 with respective connectors 1344 and a non-reopening clamp which is pre-installed and continuous with a feed line 1370. The dongle 1360 may be as described with reference to FIGS. 2A and/or 3, for example. The disposable circuit also includes a path selector, pumping, and short term filter portion 1315. An embodiment of the latter is described with reference to FIG. 23, infra. The latter contains a short term filter (not shown here) that is used once for each batch of treatment fluid prepared. A line 1366 may be provided for connection to containers of medicament concentrate 1310. Another line 1368 may connect a pre-connected and sealed batch container 1317 for storing sufficient medicament for multiple treatments to a line 1369 via a connector 1344E. Note that the connector 1344E may or may not be provided between the batch container 1317 and the path selector, pumping, and ST filter circuit 1315 since they may be supplied as a single presterilized disposable.

A source line 1364 may be provided to provide water to a treatment device 1312 such as a hemofiltration machine or peritoneal dialysis cycler. The treatment machine 1312 may include a fluid circuit (not shown separately) which includes a connector 1344A for a source line 1372 and a drain line 1362 with a connector 1344B. There may be connector to mating connectors on a panel (not shown here) of the fluid preparation and storage system 1303. Connectors 1334B and 1344C of the fluid preparation and storage system 1303 may connect at a Y-junction 1397 to provide a single common drain connection 1396 which may be connected to a sewage service 1393 or to a spent-fluid container 1392. In yet another embodiment, the fluid preparation and storage system 1303 may provide a disposable waste container 1313, waste line 1385, and a pump 1383 to collect and discharge waste fluid after each treatment or when a new batch is prepared (the procedure for which will be described shortly). The collection of waste in a container is not required in the fluid preparation and storage system 1303 but in some cases it may be preferred, such as when long term connection to a drain 1393 is not convenient or when a patient wishes to move the treatment location frequently. A fluid quality sensor 1322 such as a conductivity sensor, opacity sensor, bubble detector; is provided in a discharge line 1345 to allow the treatment fluid to be tested for quality by sending a sample through the discharge line 1345. The fluid quality sensor 1322 may be rinsed in a further step by pumping purified water through the discharge line 1345.

A final pyrogen-trapping filter 1349, preferably with a small pore size of 1.2 micron or similar, may be used in the line 1364. Such a location and pore size combination may help to prevent the treatment machine from being used if an accidental bacteria bloom occurred. The small size and fine porosity makes this filter 1549 very susceptible to clogging by even a small amount of contaminant. Therefore, the treatment machine, or a component on the supply side, is preferably fitted with a high or low pressure alarm to detect such clogging and shut down and alarm on such a clogging condition. The combination of the pressure sensor and the small size filter with fine porosity forms a detector of low levels of contamination.

A pump and one or more actuators in operative association with the path selector, pumping, and short term filter portion 1315 may be provided in various configurations to move fluid between selected lines among lines 1366, 1369, 1370, 1345, and 1364. An example of a pump and actuators is discussed below with reference to FIG. 23. Referring to FIGS. 19B to 19J, by moving fluid between selected lines among lines 1366, 1369, 1370, 1345, and 1364 the between selected lines among lines 1366, 1369, 1370, 1345, and 1364 may perform various operations as follows.

Figure 19B:
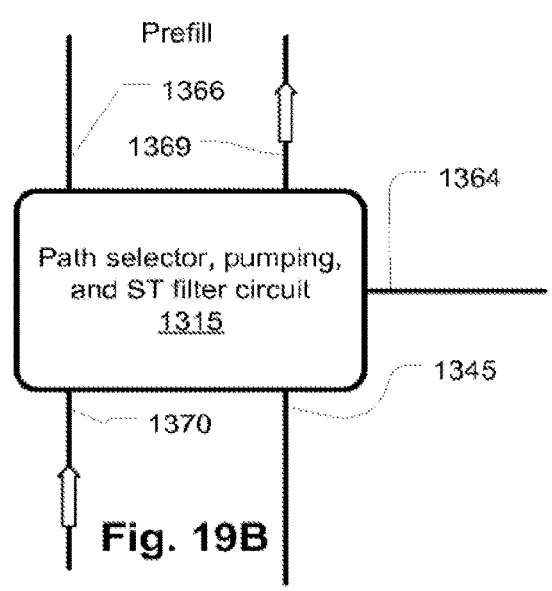
FIGS. 19B through 19H and 19J illustrate operating modes of a flow circuit component and control component of a treatment fluid preparation and storage device according to an embodiment of the invention.

1. As illustrated in FIG. 19B, the path selector, pumping, and ST filter circuit 1315 may provide for prefilling the batch container 1317 with purified water by pumping filtered water from feed line 1370 to line 1369 of the path selector, pumping, and ST filter circuit 1315. The pumping may be performed by the metering pump of the pretreatment pumping module 1295 and/or by means of a pump in the path selector, pumping, and ST filter circuit 1315 portion. The transfer of a predetermined quantity may be established by weighing the batch container, by summing the quantity transferred by the metering pump 1029 (FIG. 7), by an optical or mechanical level detector in operative association with the batch container 1317, etc. The quantity in the batch container 1317 may ensure that concentrate is well-mixed in the completed batch and may avoid the need for mixing of the diluted treatment fluid within the batch.

Figure 19C:
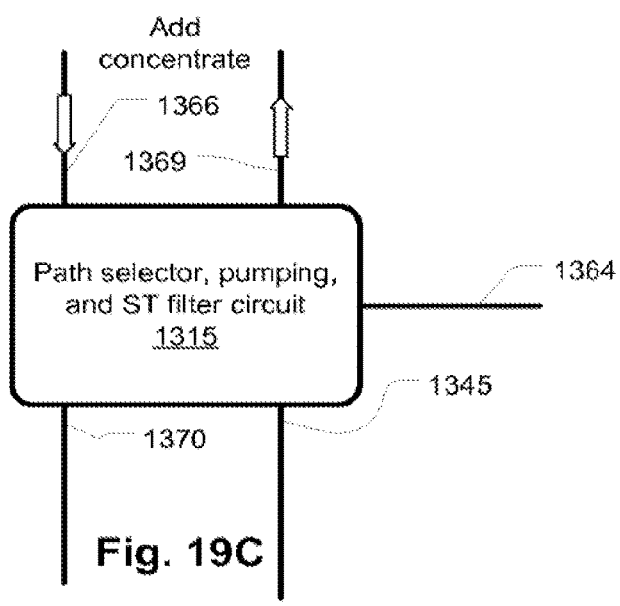

2. As illustrated in FIG. 19C, the path selector, pumping, and ST filter circuit 1315 may provide for the transfer of fluid between lines 1366 and 1369 to transfer concentrate from the concentrate container 1310 to the batch container 1317. The concentrate may be pumped or siphoned.

Figure 19D:
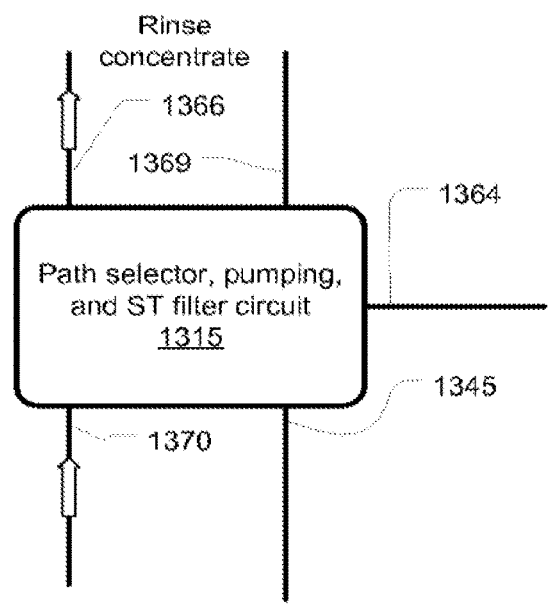
Figure 19E:
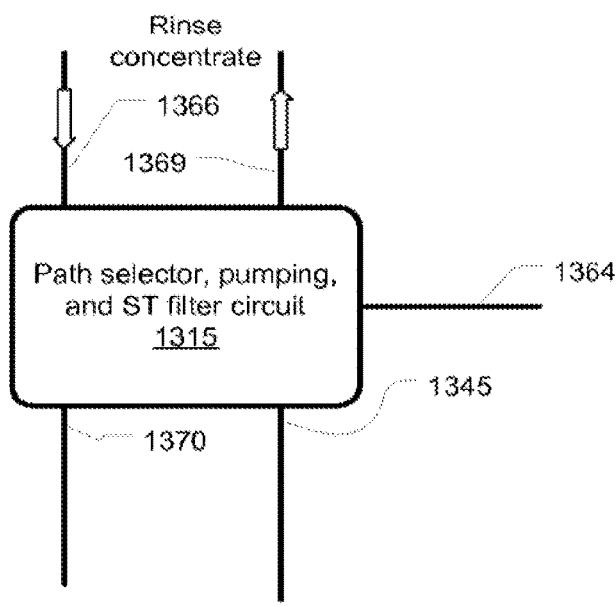

3. As illustrated in FIGS. 19D and 19E, the path selector, pumping, and ST filter circuit 1315 may provide for repeated cycles of diluting the concentrate in the concentrate container 1310 and transferring rinsed concentrate to the batch container 1317. This may be done by transferring fresh purified water to rinse the concentrate container 1310 by flowing water from line 1370 to line 1366 (FIG. 19D) followed by transferring diluted concentrate from line 1366 to line 1369. These steps may be performed repeatedly until a specified number of cycles of dilution and transfer are completed. The number of cycles may be determined experimentally as sufficient to ensure a repeatable quantity of concentrate is transferred or a certain maximum quantity of concentrate remains in the concentrate container 1310. Preferably, the concentrate is provided in a rigid container that may be effectively rinsed by the above process. Other types of container may be used, however, such as hangable medical fluid bags, solute cartridges, etc. Also, preferably the concentrate is one that permits long term storage as a prepared treatment fluid for dialysis. Note also that instead of a single component concentrate, a multi-component acid component can be mixed with a dry bicarbonate component and used with the present system, particularly if used for acute care and the storage term is limited suitably or other means, such as mixing of the batch, are employed to avoid precipitation which may attend the use of mixed bicarbonate-based treatment fluid. Other alternatives are possible and are not excluded from the scope of invention.

Figure 19F:
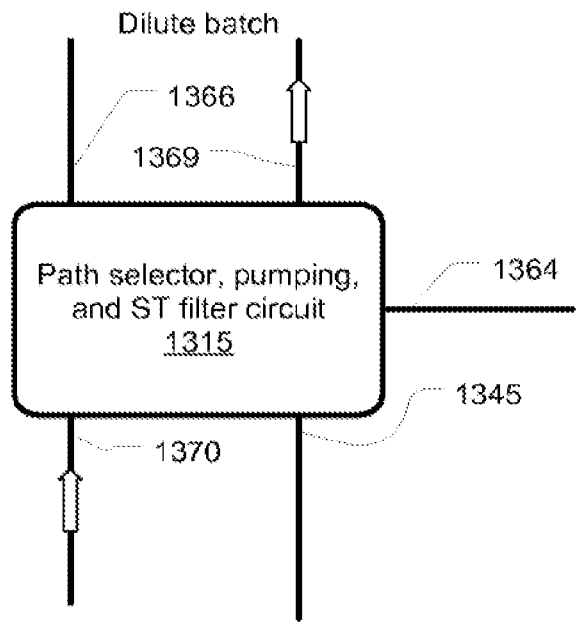
Figure 19G:
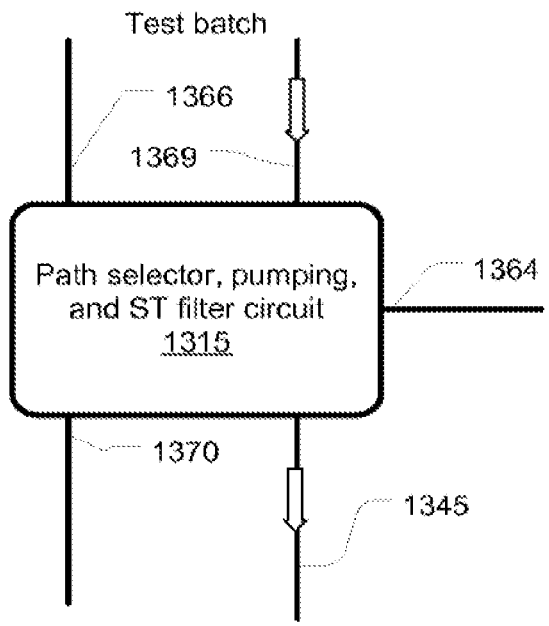
Figure 19H:
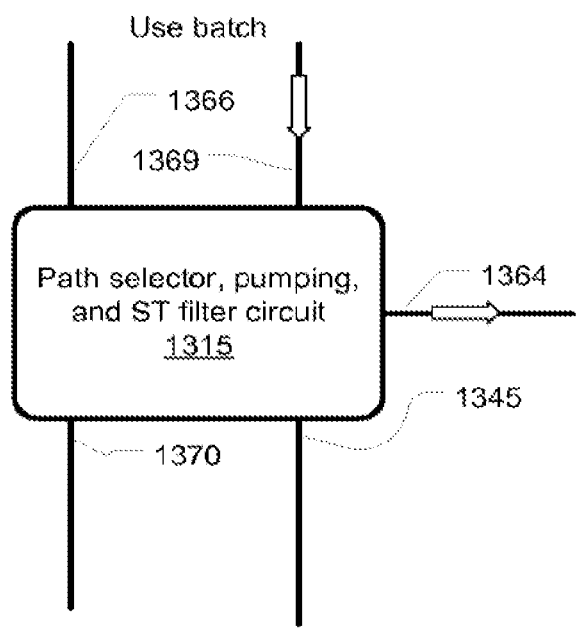
Figure 19J:
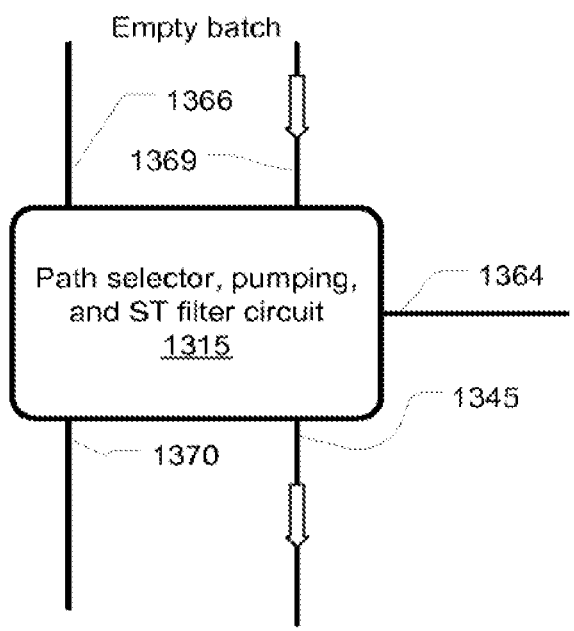

4. As illustrated in FIG. 19F, the path selector, pumping, and ST filter circuit 1315 may provide for the transfer of fluid between lines 1370 and 1369 to transfer purified water to the batch container 1317 and complete the dilution of the batch.
5. As illustrated in FIG. 19G, the path selector, pumping, and ST filter circuit 1315 may provide for the transfer of fluid between lines 1369 and 1345 to transfer fluid from the batch contain 1317 to the quality sensor 1322 to test the quality, for example, the conductivity of the completed batch.
6. As illustrated in FIG. 19G, the path selector, pumping, and ST filter circuit 1315 may provide for the transfer of fluid between lines 1369 and 1364 to make the fluid in the batch container 1317 available to a treatment device such as treatment machine 1312.
7. As illustrated in FIG. 19J, the path selector, pumping, and ST filter circuit 1315 may provide for the transfer of fluid between lines 1369 and 1345 to transfer fluid from the batch contain 1317 to the drain 1397 junction to empty the batch container 1317. This may be done if the batch expires before being used or the entire contents of the batch are not required or for other reasons. In an alternative embodiment, the steps of 19B, 19C, 19D, 19E, and 19F may be omitted by providing concentrate in the batch container 1317. Another means of transferring the required solute, such as dry solute, may also be provided according to various mechanisms in the prior art which do not require rinsing, such as an inline medicament cartridge (See, for example, Jonsson, et al.: U.S. Pat. No. 4,784, 495).

Figure 20A:
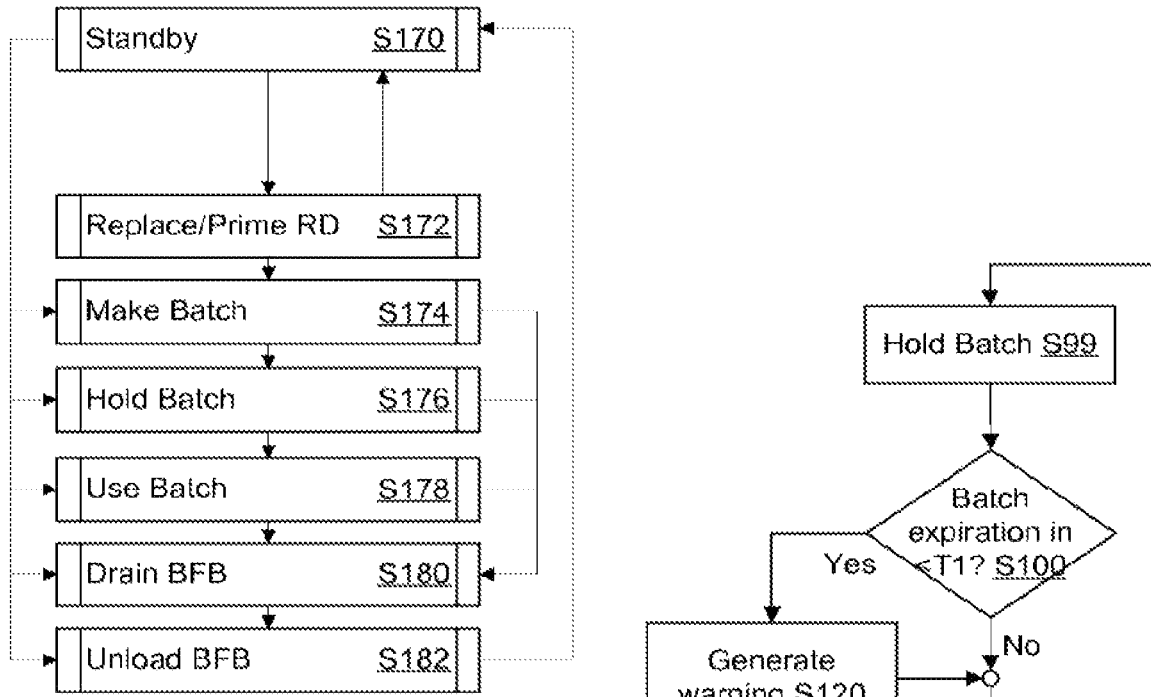
FIGS. 20A and 20B are flow charts illustrating operations of a treatment fluid preparation and storage device according to an embodiment of the invention.

As mentioned, the system 1399 of FIG. 19A may provide batch preparation and storage as well as monitoring functions and support for treatment systems. In an embodiment, in overview, the functions that may be provided are shown in the state diagram of FIG. 20A. From a standby state, the system may initialize the LTF module 1305 (S172) by priming it and testing its performance. The latter step may involve the replacement of the LTF module 1305 and in a preferred embodiment would be done on a schedule ranging from monthly to four times per year depending on the precise capacity of the LTF module 1305. The system may perform the functions of creating a batch S174 and holding a batch while maintaining its temperature S176. The system may make the batch available for use by providing the fluid at a predefined pressure S178. Further functions of draining the batch container 1317 in step S180 and unloading the batch container 1317 by disconnecting in step S182 are also provided.

Figure 20B:
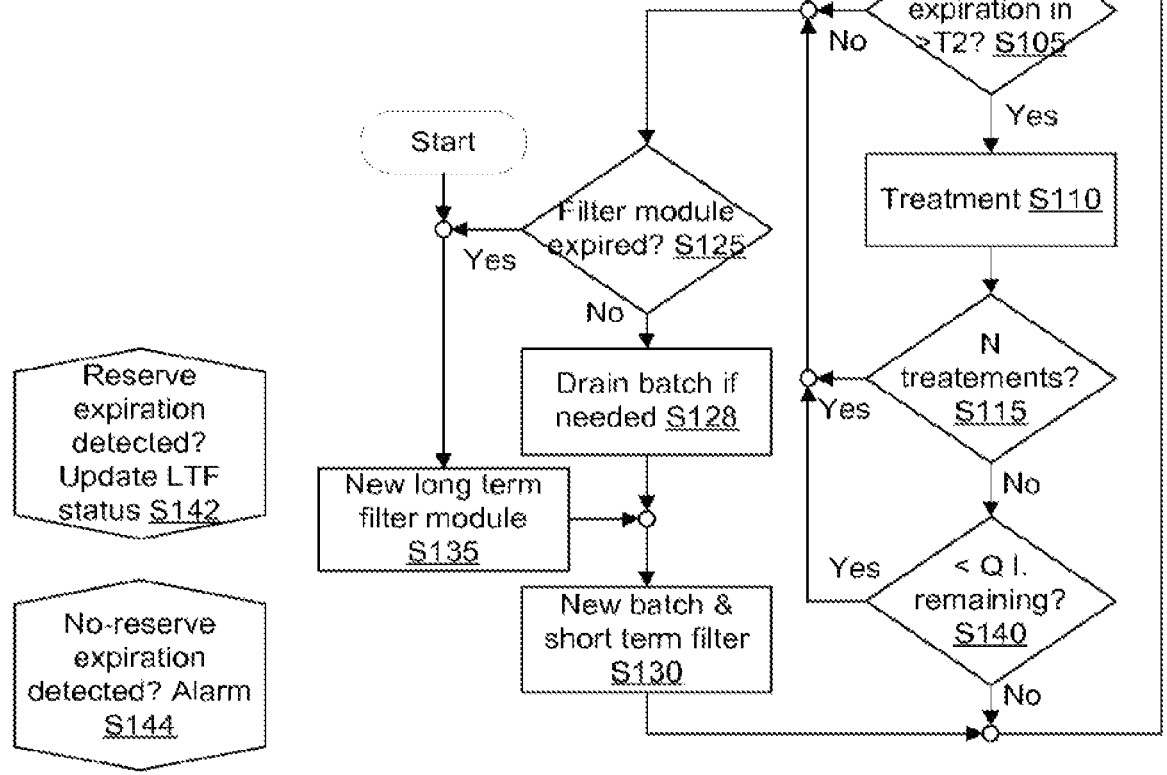

FIG. 20B shows a typical flow attending normal usage of various the embodiments of a batch preparation and storage system according to various exemplary embodiments described herein. Initially, assuming the system 1399 has been fitted with the components of the permanent portions such as a pretreatment module 1295 and UV/pump module and all controls are in working order, the typical routine provide a new LTF module 1305 at step S135. Then a new batch container 1317 and STF circuit 1315 may be installed and filled at step S130. The batch may be held until required at step S99. Heating may be performed during both steps S130 and S99. Periodically, or when a user attempts to use a batch, at step S100, the system (e.g., 1399) may determine if the batch is near a point of becoming unusable. This may be established by testing or by determining if it the current time since the batch was created is near a protocol limit (e.g., >T1-N hours) and if so a warning may be generated S120. The amount of time that establishes whether a warning may be generated may be determined based on the duration of a treatment, plus a safety margin. In an exemplary embodiment, the warning interval is 8 hours so that if a batch normally is considered to be expired 72 hours after creation, the warning would be given 64 hours after creation. The warning allows the user of the system to use an existing batch rather than allowing it to expire and then being required to make a new one before being treated.

The warning generated at step S120 may correspond to a conventional annunciator such as a bell or it may be an automated web server that generates an email, IM message, cellular SMS, cellular voice message, pager alert, or any other suitable message rendering service. The lead time before which the alert will be generated may made a user-selectable period.

In step S105, it is determined if the batch retention period has expired, requiring a new batch to be generated. If the batch has expired, or if there is insufficient time before expiration to make normal use of a batch, a warning message to that effect may be generated as indicated by the dotted lines. The message may or may not be provided. If the batch has expired, or if there is insufficient time before expiration to make normal use of a batch, control step S125 is performed. If not, a treatment may be performed S110. If the batch is depleted S140 or a treatment count on a stored batch is reached S115 (these may be alternatives in a given embodiment or both tests may be done), control proceeds to step S125.

At step S125, the system may determine if the LTF module has expired as indicated by a test or by an elapsed time period or both. If the LTF has expired, control returns to step S135 and if not, it is determined if the batch container needs to be drained. If so, the batch container is drained and removed and, in either case, control then proceeds to step S130.

At any point in the control flow, various system tests may be performed. One of the more important is the testing of the quality of water purification performed by the LTF module. In step S142, which may be performed, essentially, at all times, if the LTF module is determined to be near expiration, as discussed with regard to the resistivity probe 1022 in FIG. 8A. In such a case a status (stored as a semaphore in a memory of a controller, for example) of the LTF module may be updated to prevent its use after a current batch is completed. This status may be interrogated in step S125 and used to determine if the LTF module is expired. Step S142 represents both the continuous test of the LTF module condition as well as the step of updating the status if the condition warrants. Also at any point, a breakthrough of contaminants in the LTF module, for example sensor 1025 (FIG. 8A) may indicate the instant expiration of the LTF module at step S144. In that case, step 144 includes the initiation of safeguard procedures such as shutting down of pumps and/or the generation of alarms. Again, alarms may be of any sort, including wireless or web-based messages to users, service providers, treatment supervisors, etc.

Figure 21A:
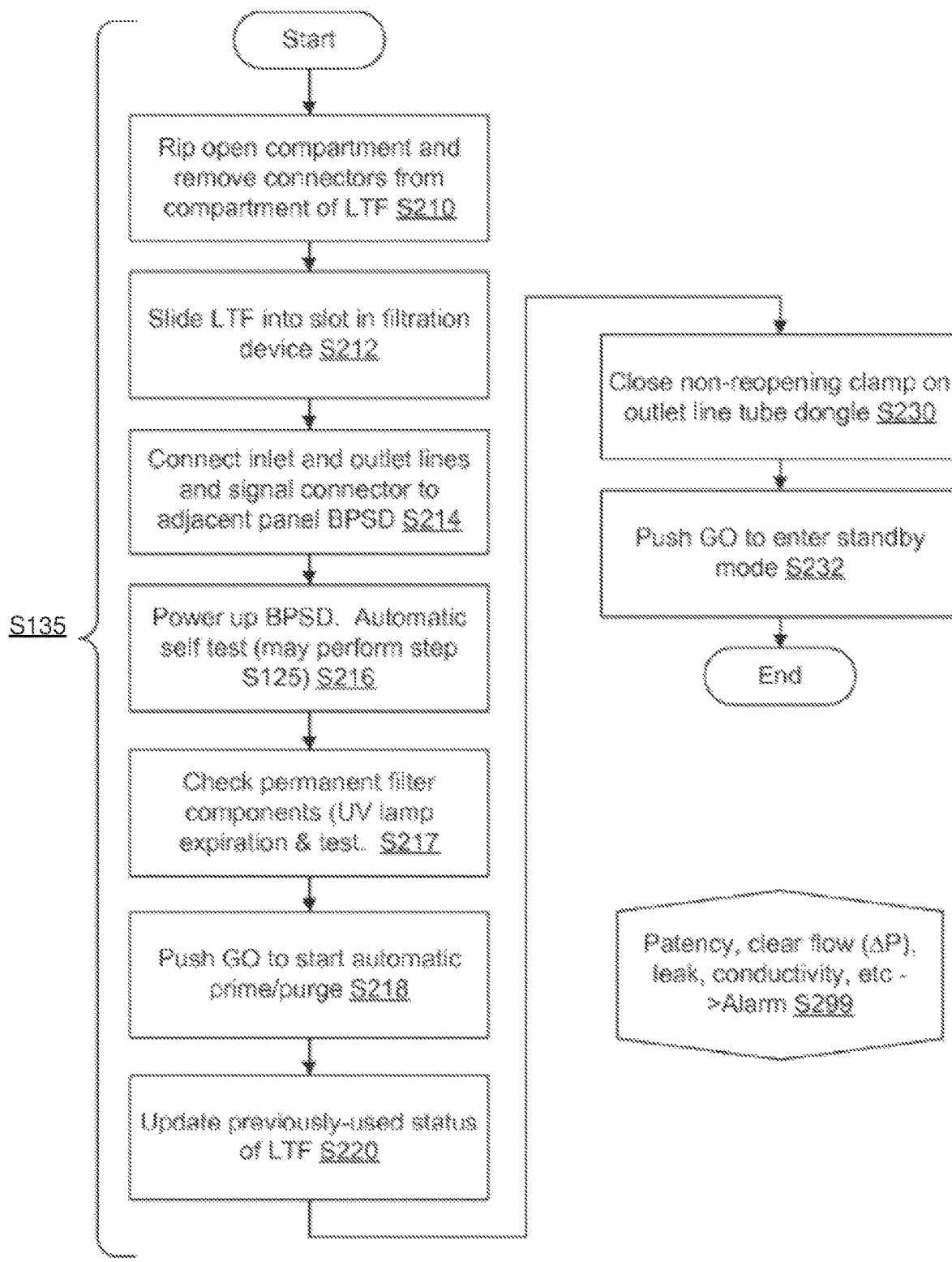
FIGS. 21A to 21C illustrate details of the operation of FIGS. 20A and 20B.

Step S135 may include the steps shown in FIG. 21A. The LTF module may be housed in a cardboard container provided with an openable compartment where all connectors, including electrical and tubing connectors, are collected and fed out. In step S210, the compartment, for example in a housing of cardboard, may be ripped open and connectors removed. The LTF module may then be put in place, at step S212, in the filtration and storage device (e.g., 1399) and connections for inlet and outlet lines and electrical connections, which may be provided on a unitary filtration and storage device as described later (FIGS. 24 and 27) may be made at step S214. The filtration and storage device (abbreviated in the drawings as BPSD for "Batch Preparation and Storage Device") may be powered up at which point at step S217, a controller may perform a sequence of self-tests including testing the UV lamp (if present), expiration (LTF module is previously used or unauthorized as discussed above), and other tests. At step S218, a user may press an actuator ("GO" button) of a user interface to start an automatic prime and purge sequence which may involve flushing the LTF module sufficiently to remove any residual agents used in manufacture of components and the clearing of any air as well as priming. The latter may be done automatically At step S230, after the system as finished with the prime/purge sequence of step S218, a non-reopening clamp on a dongle (similar to 1361, FIG. 19A) pre-attached to the LTF module and left in place until a new batch bag and short term filter circuit is connected as described further below. Then user may press the actuator ("GO" button) of the user interface to enter the standby mode S232.

During the above procedures, the system may at any point (indicated by step S299), for example after fluid connections are completed, perform pressure test to determine if there are any leaks. In this case, a pump may be run (e.g., 1029, FIG. 7) to create a pressure and then the pressure monitored for an interval to see if the relief rate corresponds to one previously determined to indicate a leak. Similarly pressure may be measured during the purge step of S218 to ensure no blockages are present as indicated by a high back pressure or an overly low backpressure which may indicate a faulty seal or filter medium. If any out of bounds conditions are found, step S299 includes the generation of a corresponding indication or alarm.

Figure 21B:
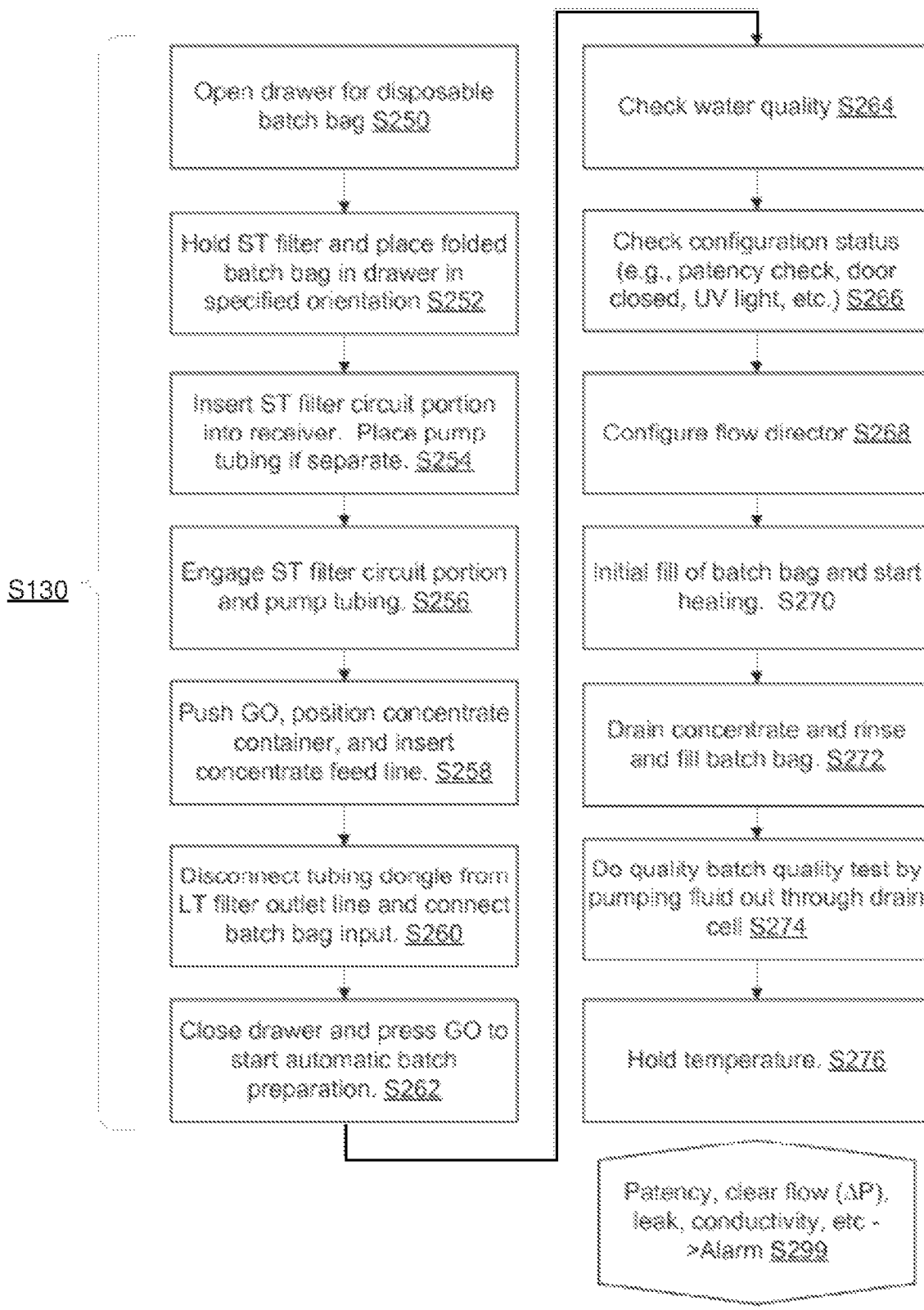

FIG. 21B shows details of step S130 of FIG. 20B. As discussed further below, the batch container 1317 may be provided as part of a disposable component with preconnected tubing, short term filter, sensors, seals, clamps, etc. The container itself may take the form of a large bag which may be shipped in a folded condition such that if laid properly in a container and filled, will unfold and expand in a predictable manner. Also, as discussed below, a support container for a large bag may take the form of a rectilinear box 1630 on drawer glides 1614 (FIG. 24). So the first step in installing the container and tubing set disposable may be to open such a drawer and to lay the bag at the bottom in a specified orientation with the tubing and connector portions fed to an accessible location. The tubes may be temporarily wrapped together around an easy to identify component such as the ST filter 1510 (FIG. 23) so that if the user holds that part, the tubes are secured from tangling and positioned in a predictable manner. See steps S250 and S252.

An alignment and retainment mechanism may be provided to secure the tubing and ST filter, for example one is described below with reference to FIG. 23. One or more steps within step S254 may provide for the alignment of the circuit with actuators, pumps, sensors, etc. and then, in step S256, these may be engaged such as by clamping or securing one or more actuator components. Examples of the mechanical aspects are discussed below. Once the circuit is secured, the user may place the system in a mode for connecting the concentrate container. This step may set any valves in position to prevent premature siphoning before the system is prepared for the transfer of concentrate to the batch container. This is done in step S258. The tubing dongle that protects the outlet of the LTF module is then removed in step S260 and the outlet from the LFT module is connected to a connector for the ST filter and batch container circuit. This connection corresponds to, for example, FIG. 19A reference numeral 1344Q. The circuit 1303 may contain a new dongle with a non-reopenable clamp 1740 which may be used later to protect the LTF module after the batch container and ST filter circuit 1303 unit is removed.

Next, at step S262, the user may invoke a batch preparation procedure, according to the current user interface by pressing GO. The procedure may begin by checking water quality S264 using the resistivity sensor 1322 (FIG. 19A) by pushing a test sample out the waste junction 1397. The system may then, at step S266, perform pressure test to determine if there are any leaks. In this case, a pump may be run (e.g., 1029, FIG. 7) to create a pressure and then the pressure monitored for an interval to see if the relief rate corresponds to one previously determined to indicate a leak. Also checked are high back pressure or overly low backpressure which may indicate a faulty seal or filter medium. The condition of a UV light source, if present may also be checked by means of a light sensor. This step S266 may be performed at other points as well.

Figure 23:
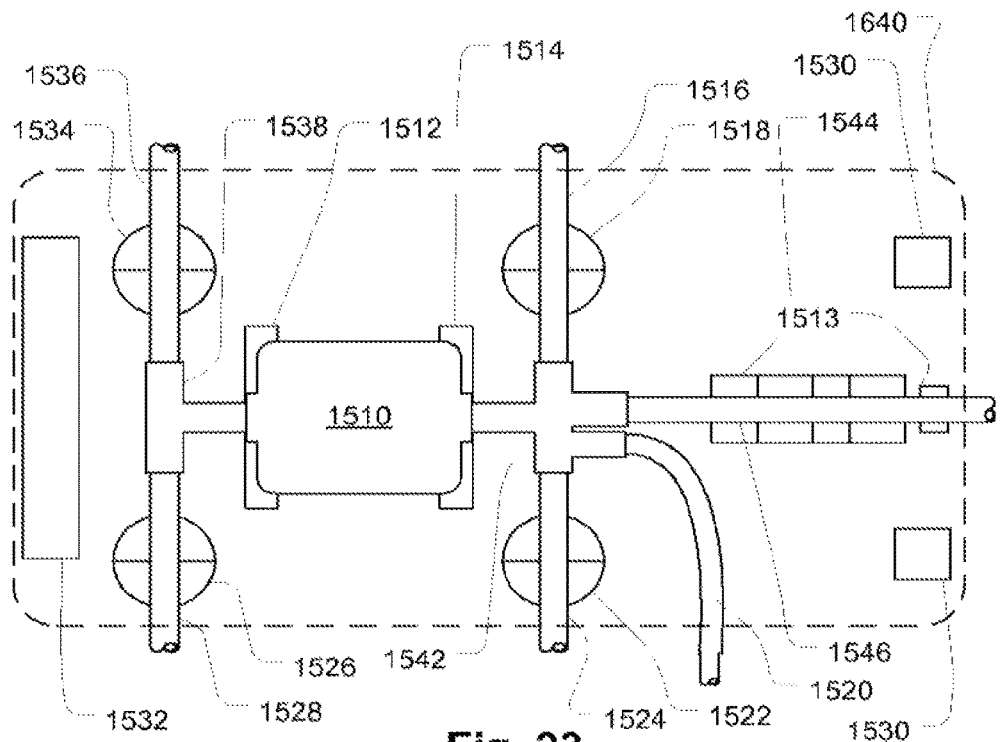
FIG. 23 is a diagram of a flow director.

The flow director (not shown here, but described with reference to FIG. 23, is then configured as described with reference to FIGS. 19B through 19J in steps beginning at step S268 to provide the functions of adding concentrate to the batch container and diluting to the correct degree. Step S270 corresponds to adding the initial quantity of water before the transfer of concentrate described above with reference to FIG. 19B. Step S272 corresponds to the transfer of concentrate to the batch container described with reference to FIG. 19C and the rinsing sequences described with reference to FIGS. 19D and 19E as well as the final completion of the dilution process described with reference to FIG. 19F. Step S274 corresponds to the fluid quality test, which may include a conductivity test, described with reference to FIG. 19G. The completed batch is warmed and held at a temperature compatible with use beginning at step S276. As above the various out of bound conditions may be tested and confirmed at various points during the process of FIG. 21B as indicated by step S299.

Figure 21C:
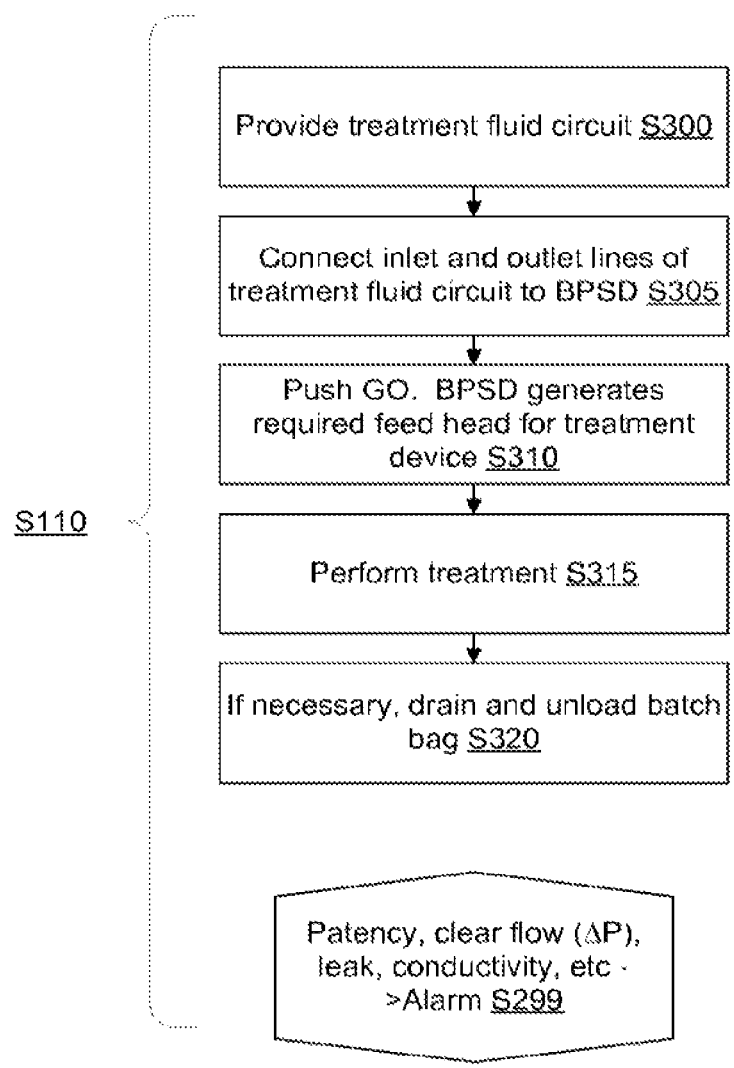

Referring now to FIG. 21C, details for step S110 are indicated which correspond to the process of using a batch of treatment fluid. At step S300, a treatment circuit and/or device is provided. Fresh and spent fluid lines may be connected as required by the particular device in step S305.

In the FIG. 27 embodiment described below (for example—true of other embodiments as well), the fresh fluid and waste fluid connections are provided so the connections may be made between the batch preparation and storage device and the treatment device. In step S310, the user may press GO or otherwise place the batch preparation and storage device in a treatment mode in which the system may run a pump to generate a head pressure equivalent to common gravity fed lines that use a hung medicament bag. The batch preparation and storage device may make the fluid available for treatment in other ways as well, for example by simply configuring valves, for example by configuring as described with reference to FIG. 19H. The treatment may be performed using the system as indicated at step S315 and then, if needed, the batch may be drained or the system placed in standby mode where the batch temperature is maintained until the next treatment (step S320). As above the various out of bound conditions may be tested and confirmed at various points during the process of FIG. 21B as indicated by step S299.

Figure 22:
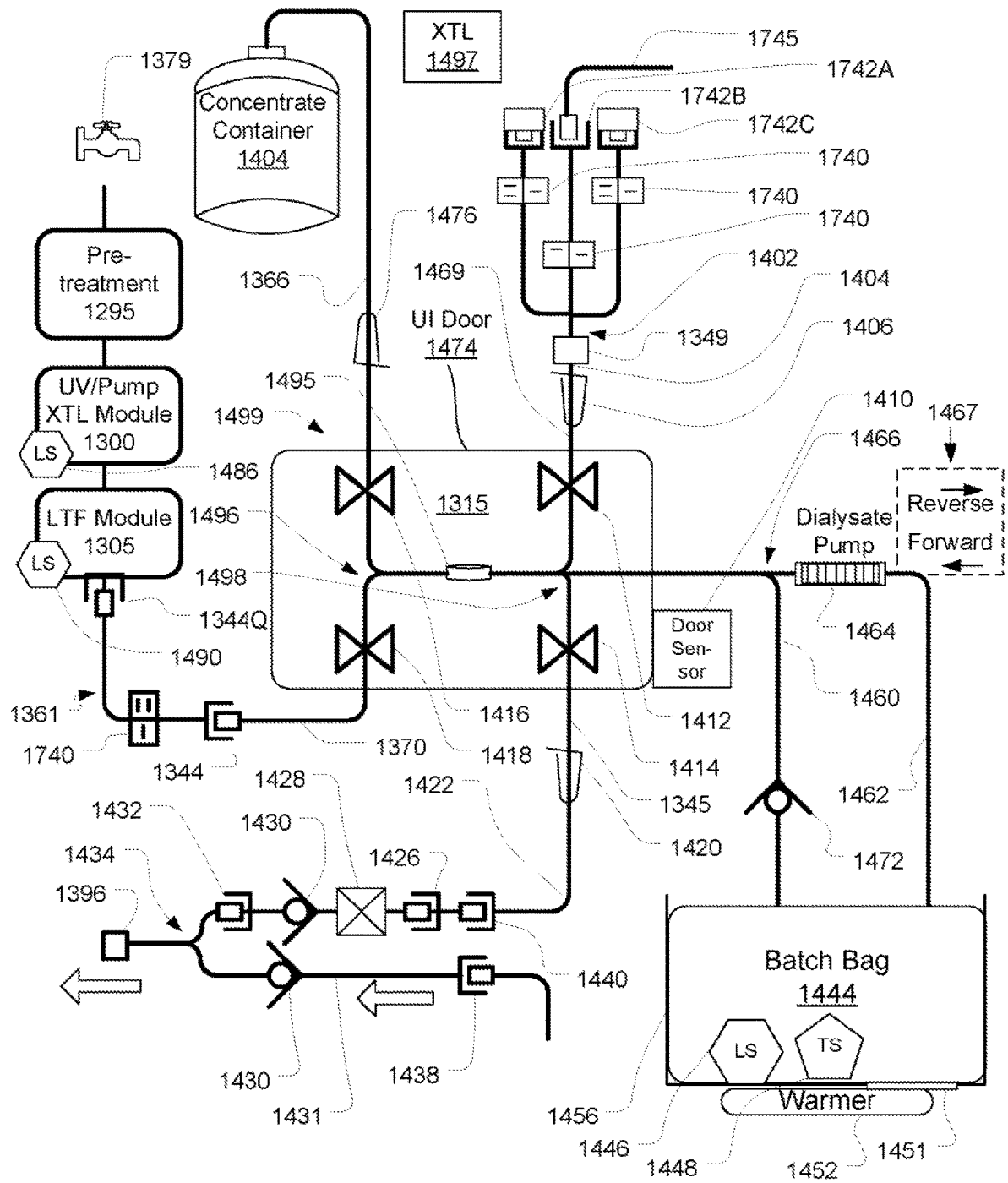
FIG. 22 is a circuit diagram illustrating features of a treatment fluid preparation and storage device according to an embodiment of the invention.

FIG. 22 is a more detailed description of a batch preparation and treatment system which is consistent with the embodiment of FIG. 19A. A pretreatment module 1295 receives water from a source, such as a sink faucet 1379, and a UV/pump module 1300 may provide a semi-permanent pre-filtration process as described with reference to FIGS. 6 and 7. The water quantity requirements are preferably such that ordinary household supplies are adequate—as will be observed, the preferred embodiments described permit this. The connection to a sink faucet may be by way of a common connector (not specifically shown) that replaces the aerators of many household faucets. A long term filter (LTF) module, for example, 1305 provides water purification for multiple multi-treatment batches, for example sufficient for daily treatments for 30 days. In a preferred embodiment, the LTF module 1305 includes KDF, segregated SAC/SCA bed deionization (DI), and mixed bed and ultrafiltration as described with reference to FIGS. 2A and 8A. The LTF module, as also described above, may be in the form of a completely disposable module which only requires a small number of connections to replace. Various connectors are omitted from FIG. 22 because their description is not necessary. Like numerals (in FIGS. 19A and 22) specify similar components so their description is not duplicated here.

A particular example of a path selector, pumping and ST filter circuit 1315 is indicated at 1499. Four valves 1416, 1418, 1414, and 1412 and a pump 1464 are independently controlled by a controller 1497 to provide the selectable paths described with reference to FIGS. 19B through 19J. The valves are preferably pinch valves that press on medical tubing to open and close. Note that fluid may be prevented from being pumped into the batch container (in the present embodiment a batch bag 1444) by a check valve that has a lower limit requirement before it opens (a "cracking pressure"). So, for example, when water is pumped into the concentrate container 1404, it is not necessarily pumped into the batch bag 1444. The dialysate pump 1464 may also prevent water from being pumped into the batch bag 1444 as well. The following list shows the valve configuration and pump configuration for the modes of FIGS. 19B through 19J. The forward and reverse pump directions are indicated at 1467 and symbolized by "F" and "R" in the table below. The state of the pump 1464 being off, and thereby acting as a closed valve, is indicated by "X." The valve configurations are indicated by "C" for closed and "O" for open.

TABLE 1

Flow director configurations

| Figure number | 1418 | 1416 | 1412 | 1414 | Pump |
|---|---|---|---|---|---|
| 19B | O | C | C | C | R |
| 19C | C | O | C | C | R |
| 19D | O | O | C | C | X |
| 19E | C | O | C | C | R |
| 19F | O | C | C | C | R |
| 19G | C | C | C | O | F |
| 19H | C | C | O | C | F |
| 19J | C | C | C | O | F |

Fluid warmer 1452 may be thermostatically controlled using a temperature sensor 1448. A leak sensor may be provided at a location in the support 1456 for detecting any leaks from the batch bag 1444. A weight scale 1451 may be used as an alternative further means of determining the quantity of fluid transferred to the batch bag 1444. The batch bag may be supplied with concentrate already in it so that the above steps relating to transfer of concentrate from a separate container may be omitted.

The valve assembly may be as shown in FIG. 23, with a pinch actuators 1534, 1518, 1522, and 1526, compressing tubing branches 1536, 1516, 1524, and 1528, respectively against an anvil plate attached to a door (not shown in FIG. 23) that closes over the assembly. The door is hinged 1532 and latches 1530 such that the tubing branches 1536, 1516, 1524, and 1528 are compressed when the pinch actuators 1534, 1518, 1522, and 1532 are activated (moving toward the viewer from the perspective the drawing page). A pump tubing segment 1546 is held against the rollers of a peristaltic pump actuator 1544 by a pump race segment attached to the door. Tubes 1536, 1516, 1524, 1528, 1546, and 1520 in FIG. 23 correspond to lines 1366, 1469, 1345, 1370, 1462, and 1460, respectively, in FIG. 22.

Leak sensors 1486 and 1490 may be provided to detect leaks around or within the corresponding modules 1300 and 1305. A common waste junctions 1434 has connectors 1432 and 1438 for receiving fluid from the batch preparation and storage device and from the treatment device (not shown here, but the corresponding connection is 1344B in FIG. 19A). The conductivity sensor 1428 corresponds to the sensor 1322 in FIG. 19A. check valves 1430 are provided for each branch 1422 and 1431. Extra connectors may be provided for convenient replacement of components as shown.

A branching connector junction 1402 provides multiple connections for the fluid inlet of a treatment device (not shown here). To help ensure against touch contamination, each connector 1742A, 1742B, and 1742C is sealed before use. Each connector is, in turn, unsealed and connected to the inlet line 1745 of the treatment device (as is connector 1742B in the figure) while the other connectors remain sealed (as are connectors 1742A and 1742C). When a treatment is completed, a non-reopening clamp 1740 of the previously used connector (1742B) may be closed and the treatment device inlet line 1745 may be disconnected. This prevents any incursion of contaminants back into the fluid circuit or batch bag 1444. Alternatively, a check valves may be used in a single branch, but the positive seal provided by this multi-branch connector junctions 1402 is preferred.

To provide a stable and predictable source fluid pressure, similar to that provided by a fluid bag hung above a treatment device, in a situation where the batch container is below the treatment machine as it is in the preferred embodiment (See FIG. 25), a recycling loop 1462 and 1460 is provided. When the pump 1464 pumps in the forward direction, any resistance forces fluid backward through the check valve 1472, which is characterized by the above-identified cracking pressure. An exemplary pressure is 3.5 psi. Thus, during treatment, the pump 1464 runs continuously feeding fluid back into the container while the line 1469 remains substantially at 3.6 psi. If the line 1369 ascends a substantial distance, the pressure may be lowered and the final pressure "seen" by the treatment device may be provided at any desired value.

FIG. 23 illustrates an embodiment of the user interface/door 1640 which may provide a surface against which the valve actuators 1534, 1518, 1522, and 1526 operate and may position a pump race against the rollers of peristaltic pump 1544. A convenient mechanism for positioning the four tube portions 1536, 1516, 1524, 1528, 1546, the short term filter 1510 provides a rigid casing that supports junctions 1538 and 1542. The casing of the short term filter 1510 may be positioned and engaged in a holder, for example as indicated by brackets 1512 and 1514, to align the entire assembly. A support 1513 for the pump tubing portion 1546 may also be provided. A more extensive fixture may be used such as vacuum molded tray to hold the pump tubing portion 1546 as well as the our tube portions 1536, 1516, 1524, 1528, 1546 and the short term filter 1510 could also be provided so that loading is simplified.

FIG. 24 illustrates a preferred configuration for the batch filtration and storage device 1600 consistent with the embodiments described above. A unitary cabinet 1601 is provided with utility connections in back (not shown) for water supply and draining, and AC electrical feed. A drawer 1630 holds the batch bag 1444. tubes may be fed out of the drawer 1630 and directly behind the user interface door 1640. The tubes that connect to the treatment device, positioned on top of a table 1612 surface, may be fed through a notch 1641 to the treatment device. An example of a treatment device 1660 sitting on the table surface 1612 is shown in FIG. 25. The LTF module 1624, and also shown in FIG. 26, slides into a corresponding space within the cabinet 1601. A compartment 1626 can be opened (this may be done before inserting the LTF module 1624) and connectors 1632 on LTF module 1624 conveniently mated to connectors 1632 on the batch filtration and storage device 1600. The embodiment of FIG. 24 has a separate pump portion as indicated at 1602. The UV/pump module 1300 (e.g., FIG. 19A) may be located in a horizontal configuration as indicated at 1616 and slidable out of the cabinet. A door 1610 allows the majority of the units internals to be concealed during operation and a port 1608 provides access to the control panel 1604 built into the user interface door. An additional door 1622 covers the LTF module 1624. Wheels 1618 may be provided to permit the unit to moved around.

An optional replaceable primary pretreatment module 1635 is shown on the back of the batch filtration and storage device 1600 where it may be supported by any suitable means such as a shelf, brackets, hooks, Velcro, etc. Embodiments of the primary pretreatment module 1600 is shown in FIGS. 40 and 43.

Figure 40:
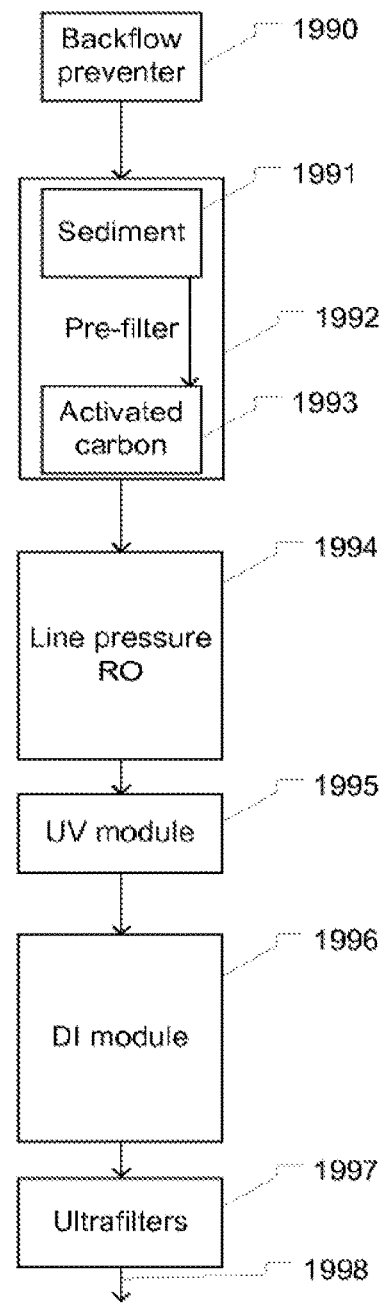
FIG. 40 shows a structure used for preparing ultrapure water and employing a line-pressure RO filter stage.

In the embodiment of FIG. 40, the reverse osmosis filter is positioned downstream of a pre-filter 1992, including sediment 1991 and activated carbon 1993 filter stages) and upstream of a UV module 1995, a DI module 1996, and ultrafilters 1997 to produce pure water at an outlet 1998. The components are described elsewhere in the instant specification so the details are not discussed again here. A backflow preventer 1990 is also optionally provided.

In the embodiment of FIG. 43, a reverse osmosis filter 2002 supplies water to the pretreatment filter 2004 such as that in pretreatment module 900 in FIG. 5. (The pretreatment module is generic to most of the embodiments described in the instant specification.) Alternatively, the reverse osmosis filter 2002 may receive water from the pretreatment module 2004 or the pretreatment module may be modified by moving the sediment filter ahead of the reverse osmosis filter 2002 and using the pump in the pretreatment module to pull water through the reverse osmosis filter 2002. The purpose of the reverse osmosis filter is to reduce the total volume of material in the water to a low level to reduce the filtration burden on the multi-batch disposable filter module represented at 2006 and consistent with the various embodiments herein (for example, with the module 910 in FIG. 8A). The reverse osmosis filter 2002 for this application is specially configured to work with normal household line water pressure and flow rates. Thus, it has a lower rejection fraction than the reverse osmosis filters normally used for water purification in renal replacement therapy application. The following are the features that characterize a preferred embodiment of the reverse osmosis filter 2002:

1. Operable at line pressure, a typical range being 10-100 psi. Therefore no additional pump is required for operation.
2. Less than 95% rejection fraction and a low recovery rate. Preferably, a rejection fraction of less than 90% combined with a recovery rate of at least 30% and preferably 50% characterize the operation of the filter 2002. These may be achieved by using a high porosity filter membrane and/or large surface area, such as by plumbing multiple filter modules 2020 in parallel via a header 2018 as shown in FIG. 44. This arrangement also provides a shallow packing arrangement which is preferably conveniently added to the batch filtration and storage device 1600 without adding significant additional floor space required by the batch filtration and storage device 1600.
3. Preferably, the reverse osmosis filter 2002 is sized to have a capacity for about 1 year of use. This corresponds to about 10,000 l. of product water.

The packing of the components of the LTF module 1680 according to an embodiment thereof, is illustrated in FIG. 26. The carbon/KDF module 1007 SAC/SBA cartridges 1002A-1002C and the mixed bed DI module 1031 described with reference to FIG. 8A are arranged in flat array as indicated at 1624. The various resistivity sensors 1684 and the ultrafilters 1682 and air filters 1688 (corresponding to 1035A and B and 1047 in FIG. 8A) are also arranged in the same plane. Connectors and lines fit into the compartment area 1626.

Figure 27:
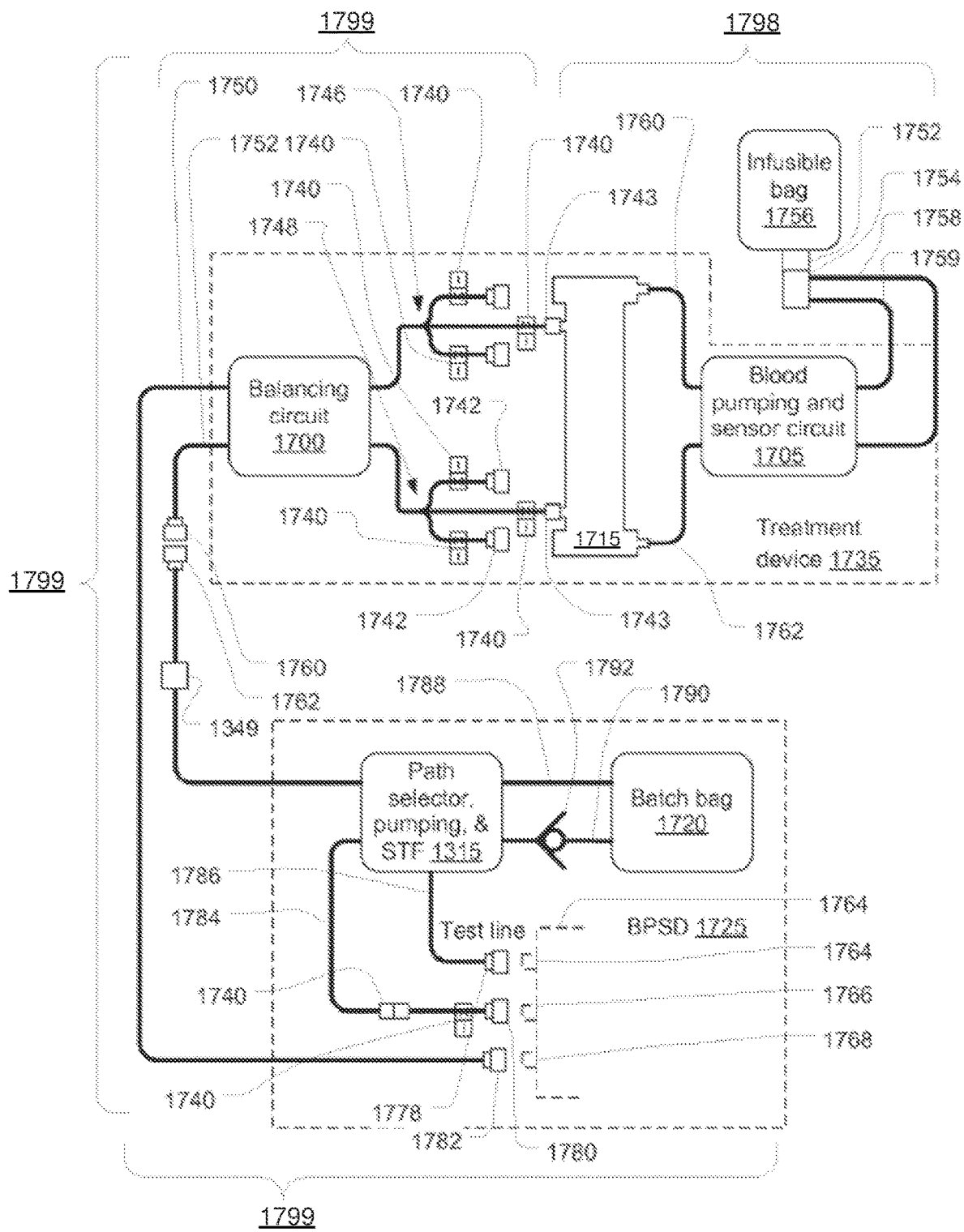
FIG. 27 is a circuit diagram illustrating features of a treatment fluid preparation and storage device according to an embodiment of the invention.

Referring to FIG. 27, a fluid circuit configuration for the treatment device allows for separate blood and dialysate circuits in a dialysis embodiment. Since the treatment fluid batch can be retained and stored for a period of days, it may be convenient to provide a fluid circuit that is retained for the same period, necessitating the exchange of only the blood portion of the circuit. This may simplify set up, reduce the risk associated with improperly installed components, and reduce cost somewhat. Here, the treatment device is indicated at 1735 and the Batch preparation and storage device at 1725. The batch bag is indicated at 1720. The check valve 1792 that provides the head pressure to feed the treatment device 1735 from below the treatment device 1735, as illustrated in FIG. 25, and feed line 1788 are also shown. The path selector circuit portion 1315 is described above and may be according to any of the embodiments or others.

Other lines 1786, 1784, and connectors 1740, 1780, 1782, 1762, and 1778 and the lines connecting them to the path selector circuit portion 1315 may be pre-connected to a balancing circuit 1700 that forms part of the treatment device 1735. Respective mating connectors 1764, 1766, and 1768 on the batch preparation and storage device 1725 may be provided such as indicated in Fig. FIG. 24 at 1632. The balancing circuit 1700 may be a volumetric balancing circuit as described in U.S. Pat. No. 6,638,478 which is hereby incorporated by reference as if fully set forth in its entirety herein. A blood filter circuit portion includes a filter (e.g. a dialyzer) 1715, blood lines 1760 and blood pumping and sensor circuit 1705, venous and arterial lines 1758 and 1759 and possibly other components. The venous and arterial lines 1758 and 1759 are shown connected to an infusible fluid bag 1756 for priming of the blood circuit which may be done with an infusible fluid delivered in the infusible fluid bag 1756. A double connector 1754, 1752 may be provided to allow fluid to be circulated through the infusible fluid bag 1756 allowing gases to settle out.

Note that the batch preparation and storage device may provide fluid for priming the blood circuit by pushing treatment fluid through the blood circuit filter 1715 into the blood circuit 1705 and into the infusible bag 1756. In this case, the infusible bag may be provided as part of the blood circuit 1705 and preattached as illustrated. Note also that it is contemplated that a patient access would be connected in some appropriate fashion after priming is completed by disconnecting the connectors indicated figuratively at 1752 and 1754.

A multiple connector 1746 may be provided, which is the same as, and used in the same manner as that connected at the junction 1402 in FIG. 22 and described with reference to that figure. For each treatment, the blood filter portion 1798 is replaced after the treatment is completed. The non-reopenable connector 1740 of the used connector among those indicated at 1746 and those indicated at 1748 is closed and the blood filter portion 1798 disconnected by disconnecting the connectors 1743 of the filter 1715. However, the treatment fluid portion 1799 can remain in place.

Figure 28:
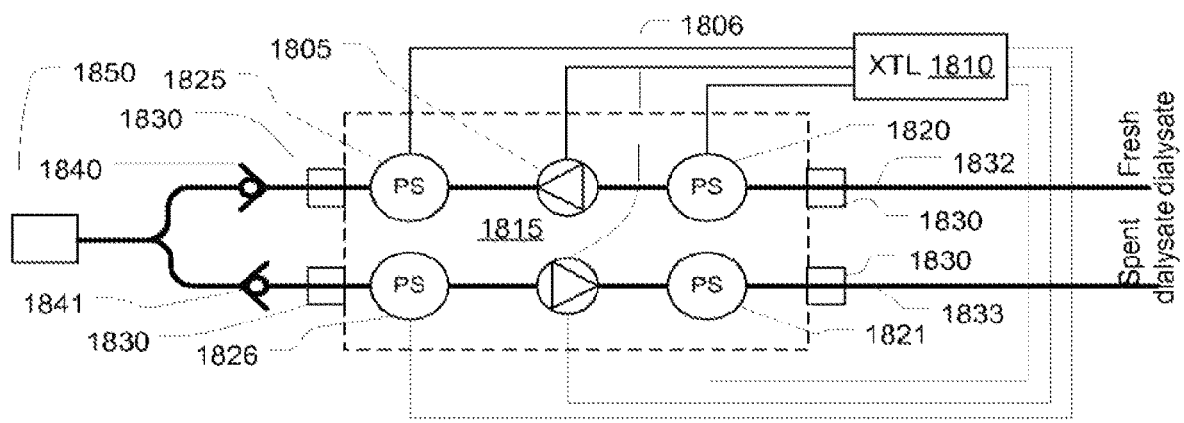
FIG. 28 is a diagram of a compact peritoneal dialysis cycler.

Referring to FIG. 28, a peritoneal dialysis device is shown. One feature of the convenient design of the batch preparation and storage device embodiments of FIGS. 22 and 25 is that they permit convenient connection to a variety of different kinds of treatment equipment. For example, instead of a full hemodialysis treatment and circuit as described with reference to FIG. 27, the batch preparation and storage device 1600 may be employed with a peritoneal dialysis cycler, an embodiment of which is illustrated in FIG. 28. The fresh and spent dialysate lines 1832 and 1833 may be connected to the batch preparation and storage device (any embodiment) as, for example, the corresponding lines 1372 and 1362, respectively, of the embodiment of FIG. 19A. Pumps 1805 and 1806 may be controlled by a controller 1810 using feedback control based on inlet and outlet pressure sensor readings from pressure sensors 1820, 1825, 1821 and 1826, respectively. In addition, precise inlet and outlet pressure readings combined with a calibration curve for each pump may allow the precise determination of total volume of fluid transferred to and from the patient. Using such a calibration curve approach may permit such a peritoneal dialysis cycler to use a compact unit using a peristaltic pump while providing high precision in metering dialysate for treatment.

The Peritoneal Dialysis Device

As is known, peritoneal dialysis can only be used up to a point in time after which the peritoneum cannot be used effectively for treatment. After this happens, patients must switch to normal dialysis, for example using an extracorporeal treatment system. However, for many patients, peritoneal dialysis is preferred and such patients may wish to use peritoneal dialysis for a period of time, and later switch to normal dialysis. Another alternative is for patients to use both peritoneal and normal dialysis at different times, giving them flexibility and potentially extending the term over which the peritoneum can be used for treatment. In such cases, as described below, convenient switching between the types of treatment machines may be facilitated with a batch preparation and storage device as described herein.

A peritoneal cycler according to the design of FIG. 28 (or other designs) may be configured to rest on a table top. The design of the batch preparation and storage device of FIG. 25 permits such a peritoneal cycler to be used until extracorporeal blood treatment is indicated at which point, the peritoneal cycler can be exchanged for an extracorporeal blood treatment device such as shown in FIG. 25. No change is required in the batch preparation and storage device 1600.

Note that the embodiments of FIGS. 19A through 28 are contemplated as being able to employ the data carrier and data carrier reader devices, described above with reference to earlier figures, for enforcing the expiration of replaceable components such as the LTF modules, ST filter and fluid circuit modules, etc. of the foregoing embodiments or the treatment circuits. In addition, the same data carrier devices may are contemplated for use in preventing re-use of previously used replaceable components.

The controller for the batch preparation storage and treatment devices above may provide a treatment scheduler that takes into account the permitted storage term of the batch and the time the batch is created or proposed to be created. Such a scheduler may accept as inputs, the times during which the patient wishes to perform treatment and the scheduler may, in response, calculate and display the window of time during which the batch should be prepared for it to be ready during those treatment times and still be available at the last treatment time. This calculation may take into account the time it takes to prepare a batch, the length of time before the batch expires, estimates of how long it takes a patient to set up a treatment and allowances for pausing treatments and other information. Alternatively, the scheduler may accept a time when a batch is proposed to be prepared and then output proposed treatment times, taking into account the type of treatment (daily or longer intervals), the intensity of treatment, size of batch, etc. The schedule may retain the schedule and make it available on a wireless device, providing reminders, etc. for the various tasks to be timely performed according to entered schedules. In a preferred embodiment, the scheduler is provided by a server application accessible through the web. The scheduler, may be a local application, a server application, or split between a server and a thin client application (the client application running on the treatment controller). The application may actually control the system to begin the preparation of the batch at a scheduled time. In the latter case, the batch container and circuit may be pre-connected to the batch preparation and storage device and so that the system can then automatically start the preparation at a scheduled time. Still further, if any problems are encountered, the scheduler system may alert the patient or other responsible person of the problem so that ameliorative actions may be taken.

Figure 29A:
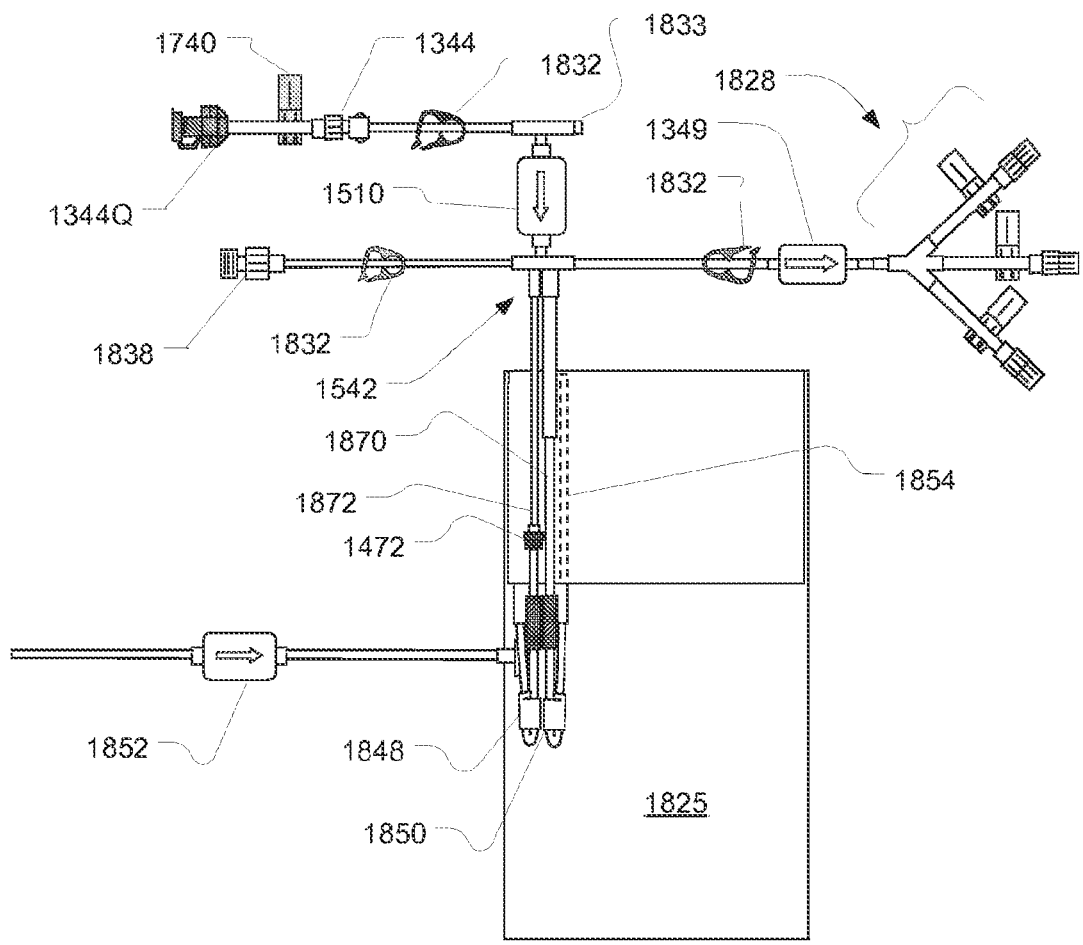
FIG. 29A shows an embodiment of a batch container and connectors which is consistent with the embodiment of FIGS. 22 and 23, for example.

FIG. 29A shows an embodiment of a batch container and connectors which is consistent with the embodiment of FIGS. 22 and 23, for example. All of the components of the batch container consumable device shown in FIG. 29A are preferably preconnected and delivered as a sealed unitary consumable component. Branching connectors 1828 are the same as, and used in the same manner as that connected at the junction 1402 in FIG. 22 and described with reference to that figure. Connectors 1742A, 1742B, and 1742C and non-reopening clamps 1740 are as described with reference to FIG. 22 and are used for connecting a batch container 1825 to a treatment device. A 1.2 micron filter 1349, as described with reference to FIG. 19A, provides a final redundant layer of protection against contamination in fluid extracted from the batch container 1825. Various clamps 1832 may be provided. The ST filter 1510 provides the functionality described with reference to FIG. 23 and other figures. The connector 1344 was described with reference to FIG. 22 as was non-reopening clamp 1740 and connector 1344Q (also described with reference to FIG. 21B). Connector 1838 is for connection to a drain.

The two lines 1870 and 1871 correspond to lines 1462 and 1460, respectively, shown in FIG. 22. The cracking valve 1472 was described above as was junction 1542. A concentrate fill line 1852 is provided to add concentrate to the batch container 1825. A premeasured quantity of concentrate may be added prior to packaging and delivery of the disposable of FIG. 29A or it may be added prior to treatment. Alternatively, a dry solute may be prepackaged in the container 1825. The embodiment of FIG. 29A is suggestive of a liquid concentrate.

Figure 29B:
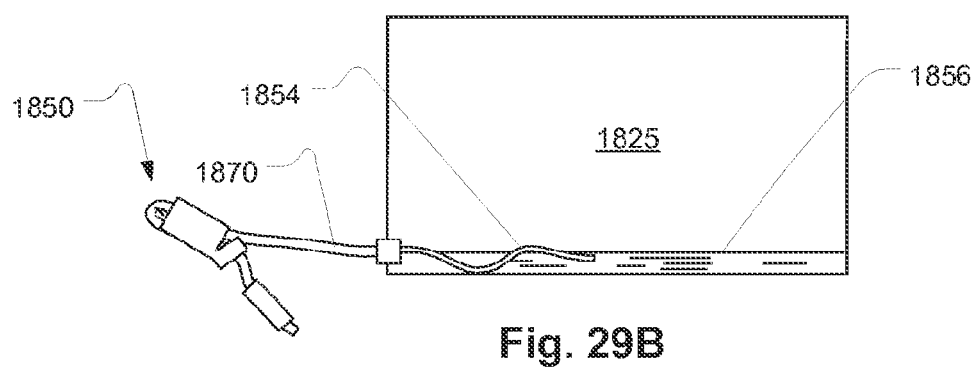
FIG. 29B shows another view of a portion of the batch container of FIGS. 29A and 29B.

The two lines 1870 and 1872 are clamped by clamps 1848 and 1850 to prevent any water from entering the batch container before preparation is to begin. The clamps that may be used are described in more detail below. Both lines 1870 and 1872 are connected to the batch container 1825 as shown in FIG. 22. Referring now also to FIG. 29B, the line 1870 may be connected to a dangling tube 1854 contained within the batch container. Liquid concentrate 1856 is shown pooled at the bottom of the container 1825. The dangling tube 1854 may be used for filling the container such that it whips around inside the container 1825 in the manner of a loose firehose, thereby stirring the water with the concentrate and promoting mixing. Alternatively, or in addition, the concentrate may be drawn into a preconnected container (which may be connected at 1833, though not shown here but configured similarly to container 1404 shown in FIG. 22) from the end of the dangling tube 1854 so that it can be mixed with water and pumped back into the container 1825. In either case, at some point after a quantity of purified water has been pumped into the container 1825, a recirculation process may be performed to thoroughly mix the concentrate and drawing fluid from the dangling tube may help to ensure that concentrate is drawn from the container and injected into the container through the other tube 1871. The dangling tube helps to ensure the most concentrated fluid is drawn off, because it would tend to pool at the bottom, and also helps to separate the inlet and outlet ports to prevent short circuiting during the recirculation process. Preferably, the dangling tube 1854 has a length of at least 10 cm.

Referring now to FIGS. 30A-30C, a tubing clamp device 1803 that may be used with the batch container of FIGS. 29A and 19B and other embodiments described above is an approximately tubular element with a slit 1808 formed partly across it dividing the device 1803 into a clamping portion 1802 and a leash portion 1807. FIG. 30B shows a detail of tubing clamp device 1803 of FIG. 30A. FIG. 30C shows a detail of a sliding collar 1804 of the tubing clamp device of FIG. 30A. The sliding collar 1804 is a close-fitting tubular element that can move along the tube, but is held in place by friction. The sliding collar, in the present and other embodiments, is preferably somewhat flexible and resilient so that it is not difficult to slide into place. The resilience of the tube will accommodate any persistent deformation in the tube shape and gradually force such deformations to relax, restoring patency of the tubing lumen.

To seal the tube 1800, the tube 1800 is run through the center 1807 of the leash portion 1807, and the center 1805 of the clamping portion 1802 and then bent 180° to form a fold 1806. Then the return leg 1810 of the tube 1800 is run back into the center 1805 of the clamp portion 1802 and through the slit 1808. The clamp portion 1802 holds a tube 1800 in a folded configuration, as indicated by fold portion 1806 sealing the tube 1800 until the clamp portion is removed.

To unseal the tube 1800, the return leg 1810 is pulled out of the clamp portion 1802 so that the fold is released as shown in FIG. 31A. The leash holds the clamp portion 1802 onto the tube 1800 so that it can be re-sued if desired. Then the sliding collar 1804 is slid over the previously-folded portion 1806 as shown in FIG. 31B, thereby rounding the tube 1800 at the previously-folded portion 1806 removing a deformation caused by folding. In this way, the tubing clamp device 1803 can be used for a long period of time to seal a tube 1800 while the sliding collar 1804 can restore the tube to full patency by rounding its cross-section.

Although the clamp portion 1802 has the leash portion 1807 in the foregoing embodiment, the leash portion 1807 is not essential and is omitted in another embodiment which is not pictured. In a preferred embodiment, the clamp portion 1802 and the leash portion 1807 are made simply by cutting a notch 1808 in a piece of suitably sized tubing. In an application such as that of FIGS. 29A and 29B, one end 1812 of the tube 1800 is connected to the batch container and the other end 1810 is connected to the junction 1542. The sliding collar 1804, preconnected to the tube, may also be fashioned from a suitably sized piece of tubing, whose inner diameter is approximately the same as the outer diameter of tube 1800.

Although the tubing clamp device 1803 and sliding collar 1804 illustrated are tubular elements, they could also have different shapes, for example, they could flat portions along their cross-sections and sill serve the described function. In addition, they need not be completely closed (i.e., form a fully circle in cross-section). For example, they could have C-shaped cross-sections enabling them to be snapped onto (or off of) the tubing 1800 rather than slid from an end thereof.

Referring to FIG. 32, a clamping device 1803A with a clamping portion 1802A includes a sliding collar 1804A attached to it for form a single unit. In an embodiment, the sliding collar 1804A is attached to the clamping device 1803A by a tape 1809, which is bonded to both the sliding collar 1804A and the clamping portion 1802A. In this case, the sliding collar 1804A keeps the clamping portion 1802A connected to the tube 1800 so that the leash portion of the earlier embodiment is not needed. Note in alternative embodiments, the connection device used is something other than a tape, for example, the sliding collar 1804A and clamping portion 1802A may be integral. As in the other embodiments, one or both the sliding collar 1804A and clamping portion 1802A, in an alternative variation, have C-shaped cross-sections rather than circular. FIG. 31A shows a first stage in the process of opening the clamping device of FIG. 30A. The clamp portion 1802 is pulled off the crimped portion 1806 and left on the tube 1800. FIG. 31B shows a second stage in the process of opening the clamping device of FIG. 30A. In this stage, the sliding collar 1804 is pulled over the folded portion 1806, thereby uncrimping it. Since the sliding collar's 1804 inner diameter is close to the outer diameter of the tube 1800, the any crimp left in the tube 1800 is completely "ironed" out by squeezing the tube 1800 crimped portion 1806 allowing fluid to flow freely. In this way, a tube can be clamped indefinitely without a problem arising from a fold imprint on the tubing 1800.

Referring now to FIGS. 33A and 33B in an alternative embodiment of a sealing device, a known type of tubing clamp 1862 is used to seal a tube 1866 by pinching it between two clamping edges 1867. The tubing clamp 1862 can remain in a closed state indefinitely, keeping the tubing 1866 sealed. When the tubing 1866 is to be unsealed, the tubing clamp 1862 is released and a sliding collar 1864 is moved over the crimped portion 1862 rounding the tubing 1866 and thereby restoring full patency to the tubing 1866 by smoothing any deformation memorized by the tubing attending the relaxation of stress caused by the crimping. Again, the sliding collar 1864 is preferably close-fitting so that it irons out any deformations in the crimped portion 1868 of the tubing.

Referring now to FIGS. 34A to 34E, another tube sealing device has a channel 1872, preferably or shape-memory alloy. such as Nitinol. or spring steel or any other suitable material which is able to retain a shape memory and return the shape without significant stress relaxation after bending. FIG. 34A is a cross-section view and FIG. 34B is a side view. In the embodiment of FIGS. 34A to 34E, the channel 1872 is U-shaped, as shown in the cross-section of FIG. 34A, so that it fits snugly about the tubing 1874 to be sealed. Bands 1886 of tape or heat shrink tubing are made to hold the ends of the channel 1872 and help to engage the tube 1874 frictionally so that the position of the tube 1874 relative to the channel 1872 remains substantially fixed. The resulting structure with bands is shown in FIG. 34C from the side. To seal the tube 1874, the channel 1872 and tube 1874 are folded as shown from the side in FIG. 34D so that a fold 1878 forms. The fold 1878 seals the tube. A band 1876 maintains the folded state of the channel 1872 and tube 1874, thereby maintaining the seal. The band 1876 may be a plastic or paper tape or a heat shrink tube or any other suitable device to hold the fold. The bands 1886 and 1876 may be replaced, in alternative embodiments, with any suitable retaining element or substance such as spring clip or adhesive.

To unseal the tube 1874, the band 1876 is removed, torn, broken, or cut to release the channel, which then returns to its U-shaped state thereby causing the sides of the channel 1872A and 1872B to urge the tube 1874 back into a rounded condition by countering the distortion caused by folding the tube 1874. That is, the sides 1872A and 1872B spring back inwardly toward each other as the channel recovers to its relatively relaxed state shown in FIG. 34C. As the sides 1872A and 1872B spring back, they press against protrusions naturally raised by the folding of the tube 1874. In an alternative embodiment, a channel 1890 has a C-shaped cross section rather than a U-shaped cross-section, which is capable of better-restoring the rounded shape of the tube 1874 because it wraps around a larger fraction of the tube 1874.

The band 1876, may be suitable to reveal tampering. The band may be attached such that it must be torn to be removed. For example, it may be tightly wrapped and fragile (e.g., of paper) or adhesively bonded to the channel 1872 such that when the tubing 1874 is unfolded, the band must be torn or otherwise disrupted in a way that unfolding is thereby revealed. For example, in FIG. 34E, halves of the band 1876A and 1876B have torn edges 1876C and 1876D caused by unfolding the tube 1874. This reveals that the seal of the tube 1874 has been compromised.

The foregoing devices may be used to clamp tubes where tubing is to be pre-connected without permitting the flow of materials therethrough. The device may used as a replacement for frangible connectors, for example, or may be used to pre-connect bags to tubing sets which otherwise would need to be "spiked" in order to provide for flow into the tubing set.

Figure 35:
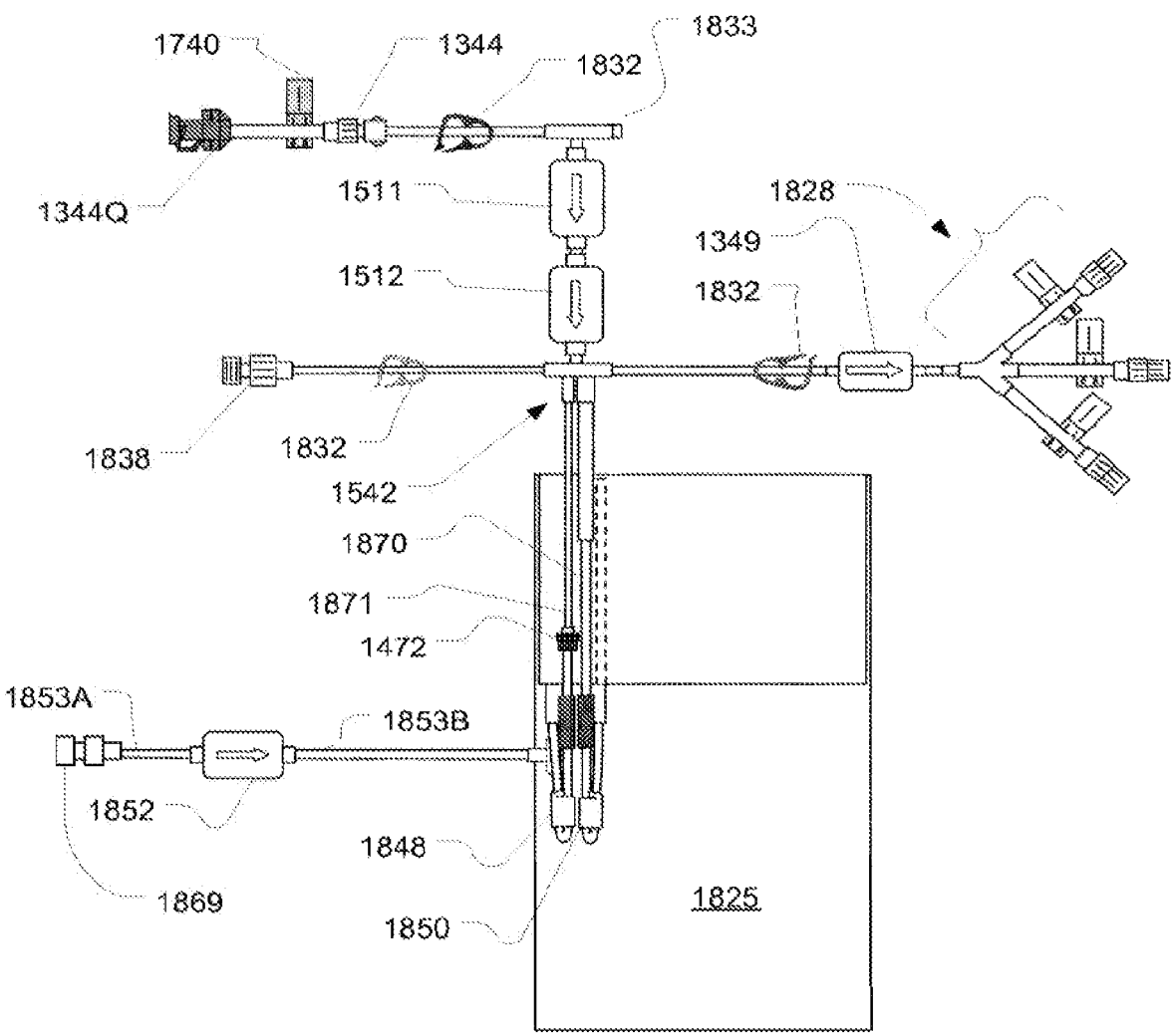
FIG. 35 shows a batch container and connectors which is consistent with the embodiments of FIGS. 22 and 23.

Referring to FIG. 35, an embodiment of a batch container and connectors which is consistent with the embodiments of FIGS. 22 and 23, for example, and with that of FIG. 29A, in particular. The embodiment of FIG. 35 differs from that of FIG. 29A in that the ST filter 1510 is replaced by two redundant ST filters 1511 and 1512 connected in series. The structure of two filters connected in series provides separate membranes with a significant physical separation distance. The separation distance is preferably at least as great as a minimum distance over which a colony is capable of growing through the membrane of the first filter 1511 and covering the distance to the second membrane of the second filter 1512 so as to contaminate the contents of the second container 1825. This can be established experimentally. In a preferred embodiment, the distance between membranes is at least a half centimeter.

By preventing break-through of contaminants in this way, a pressure test of the single ST filter such as filter 1510 of FIG. 29A, to ensure that filtering competence was not compromised during use, can be avoided. In addition, if one filter fails, the other filter provides a backup so there can be a greatly reduced risk of any contamination of the batch container 1825 contents, for example as a result of touch contamination which can occur when connections are made. The filters 1511 and 1512 protect against touch contamination redundantly, drastically reducing the odds of contamination. The filters 1511 and 1512 are preferably 0.2 micron porosity, single use filters.

Figure 36:
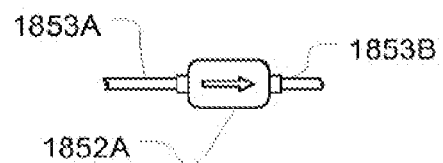
FIG. 36 shows a filter that can be used in the embodiment of FIG. 35.

In an alternative embodiment, the filter 1852, used for pre-filling the batch container 1825, for example with medicament concentrate, is pressure tested after filling the batch container 1825 through lines 1853A and 1853B. In an alternative embodiment, the filter 1852 is preferably replaced with an ultrafilter 1852A, shown in FIG. 36. Ultrafilters, as used here, are filters which are capable of filtering endotoxins. Examples of ultrafilters are the filters used as dialyzers. As an example, the ultrafilter 1852A has a pore size of less than 0.1 micron. Preferably, the ultrafilter 1853 is pre-attached to the batch container 1825 before filling with concentrate and the filter and batch container, as well as all connected components, are sterilized as a sealed unit. Once removed from the sterilization process, for example autoclave or gamma radiation sterilization, the interior of the batch container 1825 is isolated from contaminants in the outside environment, even when connectors are opened to allow concentrate to flow into the batch container 1825. Preferably, the pre-filling line 1853A has a pre-sealed connector. Preferably, also, the entire configuration of FIG. 35 is pre-sterilized as a unit and provides a single use disposable.

Referring to FIG. 37, an apparatus allows multiple batch containers, such as batch container 1825 to be pre-filled with medicament concentrate. The apparatus includes an ultrafilter 1911 illustrated here, in a preferred embodiment, in the shape of a typical dialyzer. The large capacity of the ultrafilter 1911 is such that concentrate for multiple batch containers 1825 can be filled using a single ultrafilter 1911.

Figure 39:
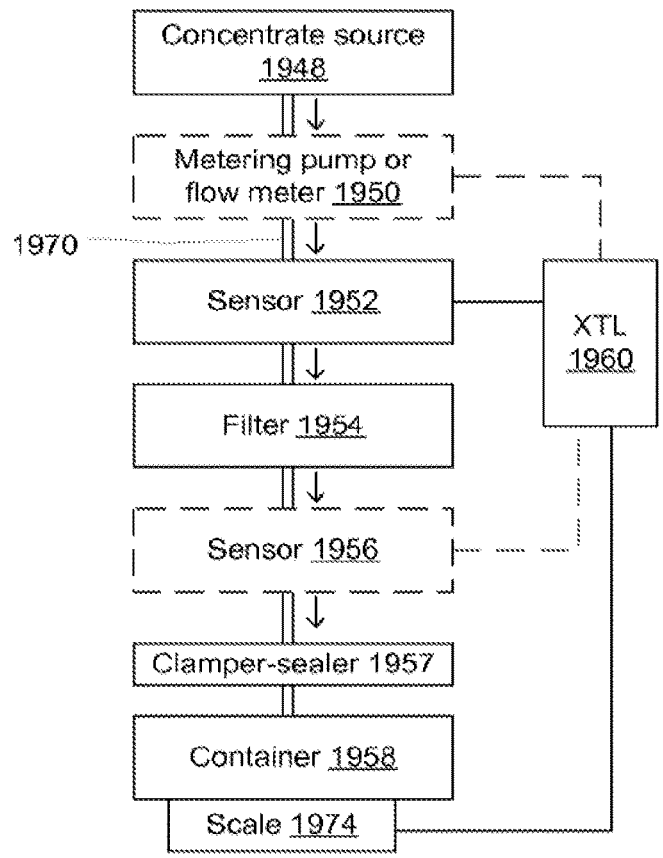
FIG. 39 shows an apparatus for pre-filling batch containers with medicament concentrate.

An embodiment of a concentrate metering system for pre-filling medicament concentrate according to the embodiments described herein is shown in FIG. 39. A concentrate source 1948 contains concentrate which is pumped by a metering pump or pump/flow meter combination 1950. The latter may apply a signal indicating the flow rate for control by a controller 1960. A sensor 1952 can be provided to measure a quality of the concentrate, such as conductivity. A filter 1954 is preferably provided and is preferably a sterilizing antipyrogenic filter with a very small porosity that blocks contaminants such as bacteria or pyrogenic particles. Another sensor 1956 may be provided or the sensor 1952 may be located downstream of the filter 1954 as indicated at 1956. A clamper/sealer 1957 is used as described in the instant specification in connection with various embodiments to seal the batch containers. The medicament flows into a batch container 1958 which may be weighed on a scale 1974 depending on the method embodiment.

In a preferred configuration, the ultrafilter 1911 is fitted with manifolds 1903 providing multiple connections 1901 to which batch containers 1927 (See FIGS. 38A and 38B below) can be attached for simultaneous filling with concentrate. Because the typical configuration of a dialyzer has two ports 1906A and 1906B two manifolds 1903 are shown. Altogether, twelve connectors 1909 extend from the two manfolds 1903. Each connector 1909 (only two of the twelve are labeled) is connectable to a batch container (not shown in this figure, but preferably configured as described elsewhere in the present application according to any of the included embodiments). FIG. 38A shows both manifolds 1903 schematically as a single manifold 1929. The manifold 1929 has multiple connectors 1925, for example locking luer-type connectors, which are pre-connected to fill lines 1935 of batch containers 1927. Each batch container 1927 has an outlet line 1933 with a connector 1931 which is sealed.

Figure 41:
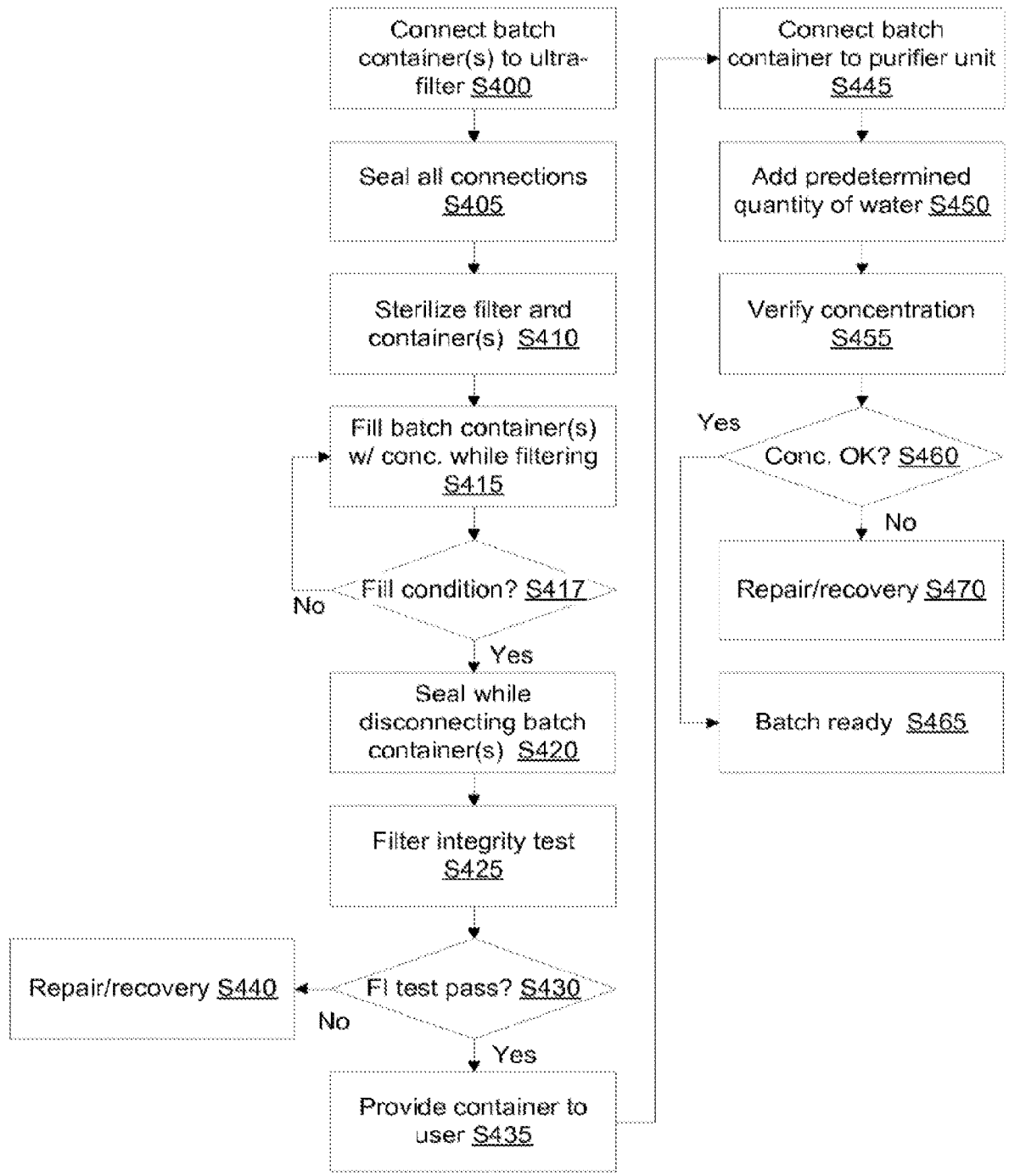
FIGS. 41 and 42 illustrate processes for pre-filling batch containers with concentrate according to respective embodiments.

Referring now also to FIG. 41, in a method of use as shown in the configuration of FIG. 38A, N batch containers 1927 are preconnected to a single filter (not shown in FIG. 38A) by the manifold 1929 in step S400. All connections are sealed in step S405. The resulting configuration is such that the interiors of all the batch containers 1927 are sealed against any intrusion of contaminants. The next step in the method of filling the batch containers 1927 with medicament concentrate, the entire set of batch containers 1927, with associated tubing and connectors and manifold 1929, is sterilized S410 (any suitable method, e.g., steam or gamma sterilization, for example) as a single unit. In step S415 the batch containers 1927 are then be filled by passing concentrate into the filter 1929 through input lines 1907 and passing the concentrate through the filter 1929. Since the filter 1929 is an ultrafilter any contamination of the batch containers 1927 is prevented. Once a predefined quantity of concentrate is added to the batch containers 1927, as determined by a fill condition in step S417, each container is disconnected and simultaneously sealed (step S420). FIG. 38B shows a disconnected batch container 1936 which has been thermally or ultrasonically sealed and detached as suggested by the pinched fill line 1937 which corresponds to the fill line 1935 before sealing and detachment. The output line 1933 with a sealed connector remains as before. A filter integrity test S425 is done on the filter 1911 to ensure that its membrane remained intact during filling. Filter membrane tests can be done by measuring an input pressure decay vs. time profile following the forcing of fluid at a specified rate and comparing to a predicted profile for an intact membrane. Alternatively, a steady state flow can be established and the pressure drop across the membrane can be measure. If the filter fails the pressure test, the filled batch containers 1927 can be either repaired or, more preferably, discarded.

Figure 42:
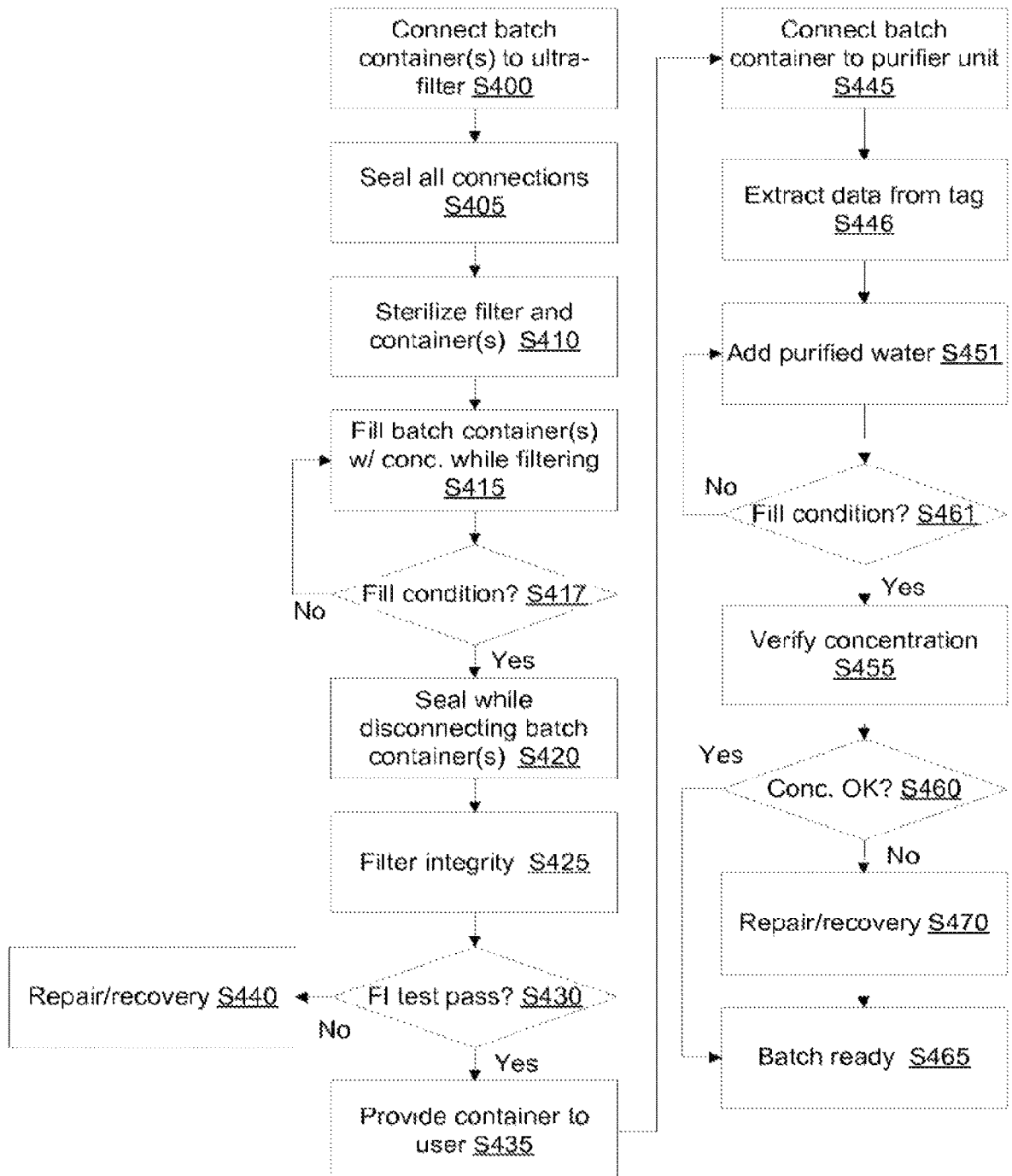

Various different methods can be used for determining if the batch containers are completely filled as in step S417. As indicated, in many of the foregoing embodiments, a batch container can be pre-filled with concentrate which is later diluted to form a medicament to be used for treatment. For example, the batch containers 450 (FIG. 2A), 1 (FIG. 4), 915 (FIG. 5) 100 (FIGS. 9A, 9B), 1317 (FIG. 19A), 1444 (FIG. 22) 1720 (FIG. 27), 1825 (FIG. 29A) could be pre-filled and delivered by the manufacturer as a sterile sealed unit with a predetermined quantity of concentrate. Preferably, the quantity of concentrate is either precisely controlled so that a predetermined quantity of concentrate can be diluted at the treatment site by metering a predetermined quantity of water into the bag or it may be preferable for the manufacturer to prepare concentrate with a variable concentration of solute and to control other parameters to ensure a proper concentration at the treatment site. This may be provided, preferably, in the following ways, referring to FIGS. 41 and 42, respectively, where cited.

1. Prepare concentrate. Meter a predetermined quantity into the batch container while measuring the actual concentration using a conductivity sensor. Calculate an amount of water needed to dilute the concentrate to a level such that a predetermined quantity of water added at the treatment site will result in a predetermined final medicament concentration. Seal the container to form the sealed consumable unit with pre-packaged concentrate. Attach the batch container to a pure water filling device. S445. The pure water filling device (which may be a purification plant as described in the present application), located at treatment site or elsewhere, dilutes the concentrate of an attached batch container with a predetermined quantity of water S450 which quantity is determined by a metering pump in the water purification device. Suitable embodiments of a water purification device are described in the present specification. Preferably, the final concentration is verified. S455. If the concentration is unsuitable S460, a recovery procedure, such as further dilution or restart of the procedure may be invoked. S470. If the concentration is valid, the batch is ready S465.

2. Prepare concentrate. Meter the concentrate into the batch container while measuring concentration and simultaneously integrating the concentration multiplied by the volume to computationally accrue the total mass of solute at a given time. Stop metering concentrate into the batch container when the total mass calculated reaches a specified quantity. Seal the container to form the sealed consumable unit with pre-packaged concentrate. The purified water filling device dilutes with a predetermined quantity of water at the treatment site. In discrete time, the procedure is Stop filling when $\Sigma C_m = (Mv_d + V_N) \cdot C_t / v_d$ where $C_m$ is measured concentration at time step
M is number of time steps at time considered for halting fill
$v_d$ is incremental volume per time step
$V_N$ is nominal volume to fill at DPM
$C_t$ is target concentration of dialysate
Attach the batch container to a pure water filling device. S445. The pure water filling device (which may be a purification plant as described in the present application), located at treatment site or elsewhere, dilutes the concentrate of an attached batch container with a predetermined quantity of water S450 which quantity is determined by a metering pump in the water purification device. Suitable embodiments of a water purification device are described in the present specification. Preferably, the final concentration is verified. S455. If the concentration is unsuitable S460, a recovery procedure, such as further dilution or restart of the procedure may be invoked. S470. If the concentration is valid, the batch is ready S465.

Prepare concentrate. Measure the concentration of concentrate in a large container used for filling multiple batch containers at a preparation facility. Determine how much concentrate should be placed in the batch containers such that a predetermined quantity of water will dilute it to optimal level for treatment responsively to the concentration measurement. Meter the determined quantity of concentrate into the batch containers. Seal the batch containers to form the sealed consumable unit with pre-packaged concentrate. Attach the batch container to a pure water filling device. S445. The pure water filling device (which may be a purification plant as described in the present application), located at treatment site or elsewhere, dilutes the concentrate of an attached batch container with a predetermined quantity of water S450 which quantity is determined by a metering pump in the water purification device. Suitable embodiments of a water purification device are described in the present specification. Preferably, the final concentration is verified. S455. If the concentration is unsuitable S460, a recovery procedure, such as further dilution or restart of the procedure may be invoked. S470. If the concentration is valid, the batch is ready S465. Prepare concentrate. Measure the concentration of the concentrate. Meter a predetermined determined quantity of concentrate into the batch containers. Program a data carrier on the batch container to indicate to the pure water filling device how much water should be added to the batch container to dilute the predetermined quantity of concentrate at the treatment site to achieve an optimal level for treatment. The present application describes a data carrier on the batch container and used to program a water purification device. The same type of device may be used to transmit data for filling batch containers by any pure water filling device and such is contemplated presently. Seal the batch container to form the sealed consumable unit with pre-packaged concentrate. Attach the batch container to a pure water filling device, which may be a purification device. S445. The pure water filling device extracts data from the data carrier. S446. The pure water filling device, located at treatment site or elsewhere, dilutes the concentrate of the attached batch container with a predetermined quantity of water S451 which quantity is determined by a metering pump in the water purification device and responsively to the data obtained from the data carrier. The filling continues until the fill condition is satisfied S461. Suitable embodiments of a water purification device are described in the present specification. Preferably, the final concentration is verified. S455. If the concentration is unsuitable S460, a recovery procedure, such as further dilution or restart of the procedure may be invoked. S470. If the concentration is valid, the batch is ready S465.

3. Meter a predetermined quantity into the batch container while measuring the actual concentration using a conductivity sensor. Calculate an amount of water needed to dilute the concentrate to a final medicament concentration by the water filling device at the treatment location. Program the batch container data carrier to indicate to the water filling device how much water should be added to the batch container to dilute the predetermined quantity of concentrate at the treatment site to achieve an optimal level for treatment. Seal the container to form the sealed consumable unit with pre-packaged concentrate. Attach the batch container to a pure water filling device, which may be a purification device. S445. The pure water filling device extracts data from the data carrier. S446. The pure water filling device, located at treatment site or elsewhere, dilutes the concentrate of the attached batch container with a predetermined quantity of water S451 which quantity is determined by a metering pump in the water purification device and responsively to the data obtained from the data carrier. Suitable embodiments of a water purification device are described in the present specification. Preferably, the final concentration is verified. S455. If the concentration is unsuitable S460, a recovery procedure, such as further dilution or restart of the procedure may be invoked. S470. If the concentration is valid, the batch is ready S465.

4. Prepare concentrate. Meter the concentrate into the batch container while measuring concentration and simultaneously integrating the concentration to cumulate the total mass of solute as in option 2, above. After adding a predetermined quantity (volume, mass, etc.) to the batch container, program the batch container data carrier to indicate to the pure water filling device how much water should be added to the batch container to dilute the concentrate at the treatment site to achieve an optimal level for treatment. Seal the container to form the sealed consumable unit with pre-packaged concentrate. Attach the batch container to a pure water filling device, which may be a purification device. S445. The pure water filling device extracts data from the data carrier. S446. The pure water filling device, located at treatment site or elsewhere, dilutes the concentrate of the attached batch container with a predetermined quantity of water S451 which quantity is determined by a metering pump in the water purification device and responsively to the data obtained from the data carrier. Suitable embodiments of a water purification device are described in the present specification. Preferably, the final concentration is verified. S455. If the concentration is unsuitable S460, a recovery procedure, such as further dilution or restart of the procedure may be invoked. S470. If the concentration is valid, the batch is ready S465.

5. Prepare concentrate. Dilute the concentrate with water using the nominal dilution factor and determine the conductivity. After adding a predetermined quantity to the batch container, program the batch container data carrier to indicate to the pure water filling device how much water should be added to the batch container to dilute the predetermined quantity of concentrate at the treatment site to achieve an optimal level for treatment. Seal the container to form the sealed consumable unit with pre-packaged concentrate. Attach the batch container to a pure water filling device, which may be a purification device. S445. The pure water filling device extracts data from the data carrier. S446. The pure water filling device, located at treatment site or elsewhere, dilutes the concentrate of the attached batch container with a predetermined quantity of water S451 which quantity is determined by a metering pump in the water purification device and responsively to the data obtained from the data carrier. Suitable embodiments of a water purification device are described in the present specification. Preferably, the final concentration is verified. S455. If the concentration is unsuitable S460, a recovery procedure, such as further dilution or restart of the procedure may be invoked. S470. If the concentration is valid, the batch is ready S465.

Note that while the above examples assume that a certain amount of concentrate is added to the batch containers which are then diluted in a second step to prepare medicament, the steps can be broken up in variations of the above embodiments. For example, concentrate could be added and diluted partly at the manufacturing site. The water filling device at the treatment location could then further dilute to obtain the final concentration. Also, while in the above examples, a data carrier was used to carry the fill volume information, this information could be correlated with a serial number or other unique identifier on the data carrier and transmitted to a networked filling device from a database according to known techniques.

Note that although in the above embodiments, the treatment regimen emphasized may have been daily treatment with moderate clearance, it should be clear that the batch preparation and treatment device and other inventive embodiments described are consistent with other treatment regimens, such as long duration (8 hours, for example, at night-time with low flow rate).

Referring now to FIGS. 45 and 46, a water purification and dialysate preparation module (DPM) 2060 consistent with various foregoing embodiments has a metering pump 2042 and a dialysate fluid reservoir (DFR) 2008 (also referred to in the present disclosure as a batch container) is connected to peritoneal dialysis cycler 2010. The latter is used for pumping dialysate into a patient to perform peritoneal dialysis (PD). In PD, it is important to control the quantity of dialysate pumped into the peritoneal cavity and the quantity removed in order to provide effective treatment, as is known. For sterility reasons, it is preferably to use a peristaltic type of pump 2030 and 2032 transporting fluids into the body. This allows hermetically sealed and disposable components, only, to come in contact with the dialysate that injected in the peritoneal cavity and reduces the risk of contamination. Peristaltic pumps are not very useful as precise metering pumps because of the compliance and imperfect relationship between pump shaft displacement (or rate) versus pumped fluid displacement (or flow rate). This is due to the compliance of the tubing, backflow, and the effects of pressure differences across the pump as well as other factors.

The DPM 2060 contains a high precision metering pump 2042 which can be used, in conjunction with pressure sensors 2044, to calibrate the peristaltic pumps 2030 to a sufficient accuracy that the peristaltic pumps 2030 can be used to pump and quantify the amount of dialysate transported into and out of the patient. During a first phase, water is purified by connecting a U-turn connector 2038 the patient access connection lines 2038 and 2040 which causes water purified by the DPM 2060 to be pumped through the PD cycler 2010 and into the DFR 2008. During this phase, which is shown in FIG. 45, the peristaltic pumps 2030 and 2032 are run while a controller 2045 monitors the pressure from pressure transducers 2044 and controls and monitors the shaft speeds of the peristaltic pumps 2030 and 2032. The controller 2045 may be configured to vary the shaft speeds of the peristalitic pumps 2030 and 2032 and/or the metering pump 2042 speed to fill out a calibration table defining pressure differences and shaft speeds versus flow rate (which is provided by the metering pump 2042 since the latter, or a controller thereof (which may be the same as controller 2045 or a different one that can communicate with controller 205) can indicate the actual flow rate. After creating a lookup table of shaft speed (SP) and pressure difference (ΔP) versus indicated flow (indicated by the metering pump and/or controller thereof), the lookup table can be used to control the process of PD treatment.

For PD treatment, an access device 2046, such as a needle, is attached to the patient access connection lines 2038 and 2040. The access device 2046 is connected to the peritoneal access of the patient. Then the primary connection lines 2035, which flow out of the water filtering system 2009 and into the PDC 2010 and from the PDC 2010 and into the DFR 2008, as shown in FIG. 45, are reconnected such that the PDC can draw dialysate from the DFR 2008 and dispose of spent dialysate as shown in FIG. 46. Then the PDC 2010 is run under control of the controller 2045 to treat a patient and using the calibrated lookup table for determining the fluid quantities infused into the patient and drawn out of the patient. Although the PDC shown has two peristaltic pumps with respective axes of rotation, in alternative embodiments, two pumps may share a common axis.

Although the foregoing inventions have, for the purposes of clarity and understanding, been described in some detail by way of illustration and example, it will be obvious that certain changes and modifications may be practiced that will still fall within the scope of the appended claims. For example, the devices and methods of each embodiment can be combined with or used in any of the other embodiments. For another example, the air vents described can be of any suitable description and need not be membrane type air vents at all, although these are preferred.

While the present invention has been disclosed with reference to certain embodiments, numerous modification, alterations, and changes to the described embodiments are possible without departing from the sphere and scope of the present invention, as defined in the appended claims. Accordingly, it is intended that the present invention not be limited to the described embodiments, but that it has full scope defined by the language of the following claims, and equivalents thereof.

The invention claimed is:

1. A system for filling multiple a plurality of containers, the system comprising:
   a plurality of manifolds, each manifold having a manifold inlet and multiple manifold outlets;
   a filter including a filter inlet port and multiple filter outlet ports, each of the multiple filter outlet ports being pre-attached to a respective manifold of the plurality of the manifolds through the manifold inlet of the respective manifold, and each of the multiple manifold outlets of the respective manifold being pre-attached to a respective container of the plurality of the containers by a respective filling line of each container of the plurality of the containers;
   the plurality of the containers, each container of the plurality of the containers having an interior, each of the respective filling lines being connected to a respective tive interior; and
   the respective filling lines, wherein all of the respective filling lines are fluidly sealed to the filter outlet ports, to manifold inlets, to the manifold outlets, and to the containers of the plurality of the containers, such that the interiors of the plurality of the containers are isolated from an external environment except the filter inlet port, via the filter, forming a combined interior volume which is sterile, an interior volume of the plurality of the manifolds being included in said combined interior volume.

2. The system according to claim 1, further comprising:
a sterilizer that is configured to sterilize the filter and the combined interior volume together and concurrently.

3. The system according to claim 2, further comprising:
a combined sealing and cutting mechanism that simultaneously cuts and seals each of the respective filling lines to isolate the plurality of containers after filling.

4. The system according to claim 1, further comprising:
a concentrated medicament;
a metering pump or a flow meter; and
a controller that controls the metering pump or the flow meter to convey a predefined quantity of the concentrated medicament through the filter to each container of the plurality of containers.

5. The system according to claim 4, further comprising:
a data carrier affixed to at least one of the plurality of containers, the data carrier storing data indicating properties of the concentrated medicament that has been injected into the container.

6. The system according to claim 5, further comprising:
at least one sensor configured to measure a concentration level of the concentrated medicament filled into a particular one of the plurality of containers, wherein the controller records the measured concentration level or a value derived therefrom in the data carrier on the particular one of the plurality of containers.

7. The system according to claim 4, further comprising:
a sensor configured to measure a fill condition and provide an output to the controller indicating the fill condition of one or more of said plurality of containers.

8. The system according to claim 7, wherein the sensor includes a scale measuring weight of at least one of the plurality of containers.

9. The system according to claim 1, further comprising:
a combined sealing and cutting mechanism that simultaneously cuts and seals the respective filling lines to isolate each of the plurality of containers after filling.

10. The system according to claim 1, wherein
the multiple filter outlet ports are two filter outlet ports.

11. The system according to claim 1, wherein
the filter includes the inlet filter port and a second filter inlet port.

12. The system according to claim 1, wherein
the filter has a cylindrical shape.

13. The system according to claim 12, wherein
the filter has two filter inlet ports and two filter outlet ports.

* * * * *